(12) United States Patent
Wei et al.

(10) Patent No.: US 8,521,292 B2
(45) Date of Patent: Aug. 27, 2013

(54) INCONTINENCE THERAPY OBJECTIFICATION

(75) Inventors: Xuan Wei, Plymouth, MN (US); Eric H. Bonde, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 156 days.

(21) Appl. No.: 12/909,625

(22) Filed: Oct. 21, 2010

(65) Prior Publication Data
US 2011/0118805 A1    May 19, 2011

Related U.S. Application Data

(63) Continuation-in-part of application No. PCT/US2010/030559, filed on Apr. 9, 2010.

(60) Provisional application No. 61/172,584, filed on Apr. 24, 2009, provisional application No. 61/183,019, filed on Jun. 1, 2009.

(51) Int. Cl.
*A61N 1/36*    (2006.01)

(52) U.S. Cl.
USPC .......................................... 607/41

(58) Field of Classification Search
USPC ................................... 607/40, 41
See application file for complete search history.

(56) References Cited

U.S. PATENT DOCUMENTS

| | | | |
|---|---|---|---|
| 4,607,639 A | 8/1986 | Tanagho et al. | |
| 4,739,764 A | 4/1988 | Lue et al. | |
| 6,266,557 B1 | 7/2001 | Roe et al. | |
| 6,449,512 B1 * | 9/2002 | Boveja | 607/41 |
| 6,652,449 B1 | 11/2003 | Gross et al. | |
| 6,735,474 B1 | 5/2004 | Loeb et al. | |
| 6,907,293 B2 | 6/2005 | Grill et al. | |
| 6,941,171 B2 | 9/2005 | Mann et al. | |
| 6,990,376 B2 | 1/2006 | Tanagho et al. | |
| 7,047,078 B2 | 5/2006 | Boggs, II et al. | |
| 7,276,057 B2 | 10/2007 | Gerber | |
| 7,280,867 B2 | 10/2007 | Frei et al. | |
| 7,489,970 B2 | 2/2009 | Lee et al. | |
| 7,505,815 B2 | 3/2009 | Lee et al. | |
| 7,548,786 B2 | 6/2009 | Lee et al. | |
| 2003/0100930 A1 | 5/2003 | Cohen et al. | |
| 2004/0199218 A1 * | 10/2004 | Lee et al. | 607/48 |

(Continued)

FOREIGN PATENT DOCUMENTS

| | | |
|---|---|---|
| WO | WO 01/54767 A1 | 8/2001 |
| WO | WO 2004/093978 A1 | 11/2004 |
| WO | WO 2010/123704 A2 | 10/2010 |

*Primary Examiner* — Carl H Layno
*Assistant Examiner* — Erin Piateski
(74) *Attorney, Agent, or Firm* — Shumaker & Sieffert, P.A.

(57) ABSTRACT

Techniques for managing urinary or fecal incontinence include delivering a first type of therapy to generate a first physiological response and, upon detecting a trigger event, delivering a second type of therapy to generate a second physiological response. The first type of therapy can be delivered on a substantially regular basis, while the second type of therapy is delivered as needed to provide an additional boost of therapy. The trigger event for activating the delivery of the second type of therapy may include input from a sensor that indicates a bladder condition, patient activity level or patient posture, or patient input. In some examples, the therapy is stimulation therapy. In some examples, objective incontinence information is generated based upon the trigger events. The system and/or user may then use this objective incontinence information to adjust therapy or select new therapy programs for improved efficacy.

35 Claims, 25 Drawing Sheets

(56) References Cited

U.S. PATENT DOCUMENTS

| | | | |
|---|---|---|---|
| 2005/0060005 A1 | 3/2005 | Boggs, II et al. | |
| 2005/0261746 A1 | 11/2005 | Gross et al. | |
| 2006/0020297 A1* | 1/2006 | Gerber et al. | 607/39 |
| 2006/0190046 A9 | 8/2006 | Gerber | |
| 2006/0190047 A1* | 8/2006 | Gerber et al. | 607/41 |
| 2006/0190048 A1* | 8/2006 | Gerber | 607/41 |
| 2006/0190049 A1* | 8/2006 | Gerber et al. | 607/41 |
| 2006/0195152 A1* | 8/2006 | Gerber | 607/40 |
| 2006/0247723 A1 | 11/2006 | Gerber et al. | |
| 2006/0293719 A1* | 12/2006 | Naghavi | 607/41 |
| 2007/0027494 A1 | 2/2007 | Gerber | |
| 2007/0027495 A1* | 2/2007 | Gerber | 607/41 |
| 2007/0100387 A1* | 5/2007 | Gerber | 607/41 |
| 2007/0100388 A1* | 5/2007 | Gerber | 607/41 |
| 2007/0293906 A1* | 12/2007 | Cowan et al. | 607/41 |
| 2008/0300650 A1* | 12/2008 | Gerber et al. | 607/41 |
| 2009/0036946 A1* | 2/2009 | Cohen et al. | 607/41 |
| 2009/0138061 A1* | 5/2009 | Stephens et al. | 607/41 |
| 2009/0222058 A1* | 9/2009 | Craggs | 607/41 |
| 2009/0306460 A1* | 12/2009 | Stephens et al. | 600/30 |
| 2010/0094372 A1* | 4/2010 | Grill et al. | 607/39 |

* cited by examiner

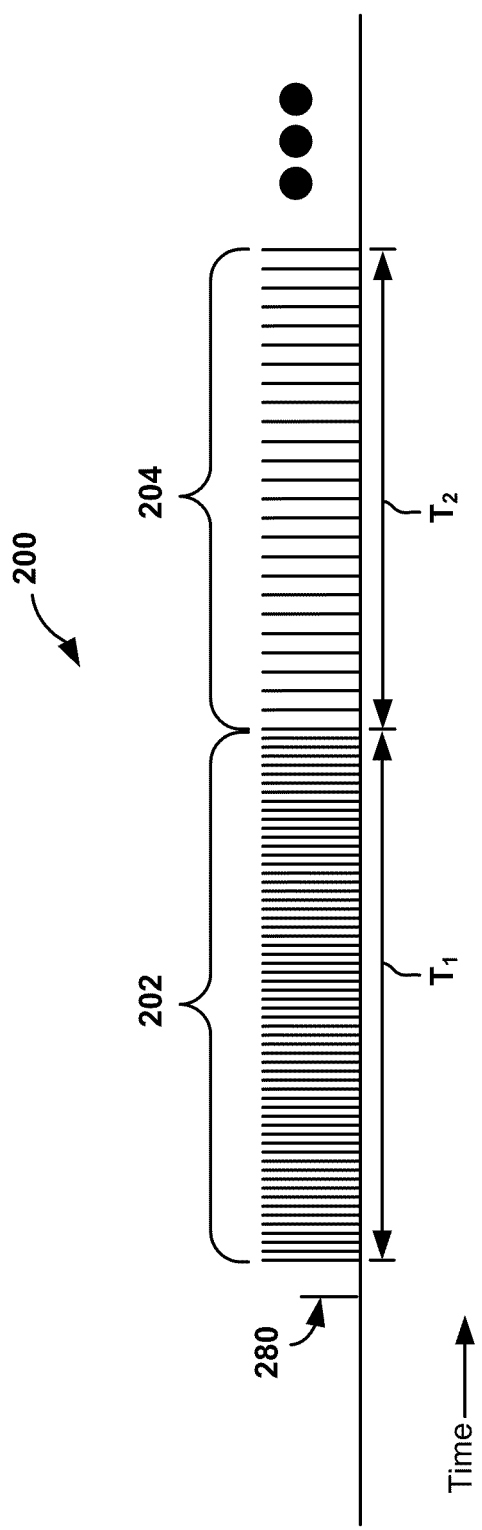

INCONTINENCE THERAPY OBJECTIFICATION

This application is a continuation-in-part of Patent Cooperation Treaty (PCT) Application No. PCT/US2010/030559, entitled "INCONTINENCE THERAPY," and filed on Apr. 9, 2010, which claims the benefit of U.S. Provisional Application No. 61/172,584, entitled "INCONTINENCE THERAPY," and filed on Apr. 24, 2009; and U.S. Provisional Application No. 61/183,019, entitled "INCONTINENCE THERAPY" and filed on Jun. 1, 2009. PCT Application No. PCT/US2010/030559 designates the United States. The entire content of PCT Application No. PCT/US2010/030559, U.S. Provisional Application No. 61/172,584, and U.S. Provisional Application No. 61/183,019 is incorporated herein by reference.

TECHNICAL FIELD

The disclosure relates to implantable medical devices and, more particularly, medical devices for the treatment of urinary or fecal incontinence.

BACKGROUND

Urinary incontinence, or an inability to control urinary function, is a common problem afflicting people of all ages, genders, and races. Various muscles, nerves, organs and conduits within the pelvic floor cooperate to collect, store and release urine. A variety of disorders may compromise urinary tract performance, and contribute to incontinence. Many of the disorders may be associated with aging, injury or illness.

In some cases, urinary incontinence can be attributed to improper sphincter function, either in the internal urinary sphincter or external urinary sphincter. For example, aging can often result in weakened sphincter muscles, which causes incontinence. Some patients may also suffer from nerve disorders that prevent proper triggering and operation of the bladder, sphincter muscles or nerve disorders that lead to overactive bladder activities. Nerves running though the pelvic floor stimulate contractility in the sphincter. An improper communication between the nervous system and the urinary sphincter can result in urinary incontinence.

SUMMARY

Techniques for managing urinary or fecal incontinence are described. According to one example, an implantable medical device (IMD) delivers first stimulation therapy to generate a first physiological response that helps prevent the occurrence of an involuntary voiding event and a second stimulation therapy to generate a second physiological response that helps prevent the occurrence of an involuntary voiding event. The first and second physiological responses are different, and in some examples, involve the activation of different muscles.

The IMD delivers the first stimulation therapy on a regular basis, e.g., to reduce bladder contractions, and, when triggered, delivers the second stimulation therapy, e.g., to promote closure of a urinary or anal sphincter. The IMD delivers the second stimulation therapy upon the detection of a patient parameter indicative of a high probability that an involuntary voiding event will occur or based on patient input. The second stimulation therapy provides a safeguard in addition to the primary incontinence therapy (i.e., the first stimulation therapy) against the occurrence of an involuntary voiding event. Thus, the second stimulation therapy provides an increased protection against the occurrence of involuntary voiding events when needed or desired.

Objective incontinence information may be generated based upon trigger events (e.g., the activation and/or delivery of the second stimulation therapy), e.g., to evaluate the patient condition or therapy efficacy. Because a trigger event occurs when there is a relatively high probability that an involuntary voiding event may occur, e.g., as perceived by a patient and/or based on one or more sensed physiological parameters, the trigger event may be used as objective information about the patient condition or efficacy of incontinence therapy. For example, information generated based on the trigger events may indicate occurrences of patient voiding, bladder or intestine contractions, duration of bladder or intestine contractions, occurrences of urgency and/or bladder or intestine overactivity, and/or bladder or intestine capacity. In some examples, the objective incontinence information may be displayed on an external programmer in one or more different formats, e.g., raw data, graphical displays or textual displays.

In one aspect, the disclosure is directed to a method comprising delivering, with a medical device, a first electrical stimulation therapy to a patient to generate a first physiological effect, receiving input from the patient or a sensor while the medical device is delivering the first electrical stimulation therapy, and delivering, with a second medical device, a second electrical stimulation therapy to the patient to generate a second physiological effect that is different than the first physiological effect based on the input from the patient or the sensor, wherein the first and second electrical stimulation therapies are configured to manage one of urinary incontinence or fecal incontinence. The first and second electrical stimulation therapies can be delivered at substantially the same time or at different times, which do not overlap.

In another aspect, the disclosure is directed to a method comprising controlling, with a processor, a medical device to deliver a first electrical stimulation therapy to a patient to generate a first physiological effect, receiving input from the patient or a sensor, and controlling, with the processor, the medical device to deliver a second electrical stimulation therapy to the patient to generate a second physiological effect that is different than the first physiological effect based on the input from the patient or the sensor, wherein the first and second electrical stimulation therapies are configured to manage one of urinary incontinence or fecal incontinence.

In another aspect, the disclosure is directed to a medical system comprising a therapy delivery module that generates and delivers a first electrical stimulation therapy to a patient to generate a first physiological effect and a second electrical stimulation therapy to the patient to generate a second physiological effect that is different than the first physiological effect, and a processor that controls the therapy delivery module to deliver the second stimulation therapy based on received input, wherein the first and second electrical stimulation therapies are configured to manage one of urinary incontinence or fecal incontinence.

In another aspect, the disclosure is directed to a medical system comprising means for delivering a first electrical stimulation therapy to a patient to generate a first physiological effect, means for receiving input from the patient or a sensor, and means for delivering a second electrical stimulation therapy to the patient to generate a second physiological effect that is different than the first physiological effect based on the input from the patient or the sensor, wherein the first and second electrical stimulation therapies are configured to manage one of urinary incontinence or fecal incontinence.

In another aspect, the disclosure is directed to a computer-readable medium containing instructions. The instructions cause a programmable processor to control a therapy delivery module (e.g., of a medical device) to deliver a first electrical stimulation therapy to a patient to generate a first physiological effect and deliver a second electrical stimulation therapy to the patient to generate a second physiological effect that is different than the first physiological effect based on received input (e.g., patient input or input from a sensor indicative of patient activity, posture or bladder condition). The first and second electrical stimulation therapies are configured to manage one of urinary incontinence or fecal incontinence.

In another aspect, the disclosure is directed to an article of manufacture comprising a computer-readable storage medium comprising instructions. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein.

In another aspect, the disclosure is directed to a method comprising, with a processor, generating incontinence information based upon at least one trigger event, wherein a second incontinence stimulation therapy is delivered to a patient to generate a second physiological effect based upon the at least one trigger event after beginning delivery of a first incontinence stimulation therapy to generate a first physiological effect that is different than the second physiological effect, wherein the first and second incontinence stimulation therapies are configured to manage at least one of urinary incontinence or fecal incontinence, and presenting the incontinence information to a user.

In another aspect, the disclosure is directed to a system that includes a configured to generate incontinence information based upon the at least one trigger event, wherein a second stimulation therapy is delivered to a patient to generate a second physiological effect based upon the at least one trigger event after beginning delivery of a first stimulation therapy to generate a first physiological effect that different than the second physiological effect, and the first and second stimulation therapies are configured to manage at least one of urinary incontinence or fecal incontinence, and a user interface that presents the incontinence information to a user.

In another aspect, the disclosure is directed to a system that includes means for generating incontinence information based upon at least one trigger event, wherein a second stimulation therapy is delivered to a patient to generate a second physiological effect based upon the at least one trigger event after beginning delivery of a first stimulation therapy to generate a first physiological effect that is different than the second physiological effect, wherein the first and second stimulation therapies are configured to manage at least one of urinary incontinence or fecal incontinence, and means for presenting the incontinence information to a user.

In another aspect, the disclosure is directed to a computer-readable medium comprising one or more instructions that cause a processor of a computing device to generate incontinence information based upon at least one trigger event, wherein a second stimulation therapy is delivered to a patient to generate a second physiological effect based upon the at least one trigger event after beginning delivery of a first stimulation therapy to generate a first physiological effect that is different than the second physiological effect, wherein the first and second stimulation therapies are configured to manage at least one of urinary incontinence or fecal incontinence, and present the incontinence information to a user. The computer-readable medium may be non-transitory.

The details of one or more aspects of the disclosure are set forth in the accompanying drawings and the description below. Other features, objects, and advantages of the examples of the disclosure will be apparent from the description and drawings, and from the claims.

BRIEF DESCRIPTION OF DRAWINGS

FIG. 15 illustrates an example prestimulus that is delivered prior to the second stimulation therapy.

DETAILED DESCRIPTION

Figure 1:
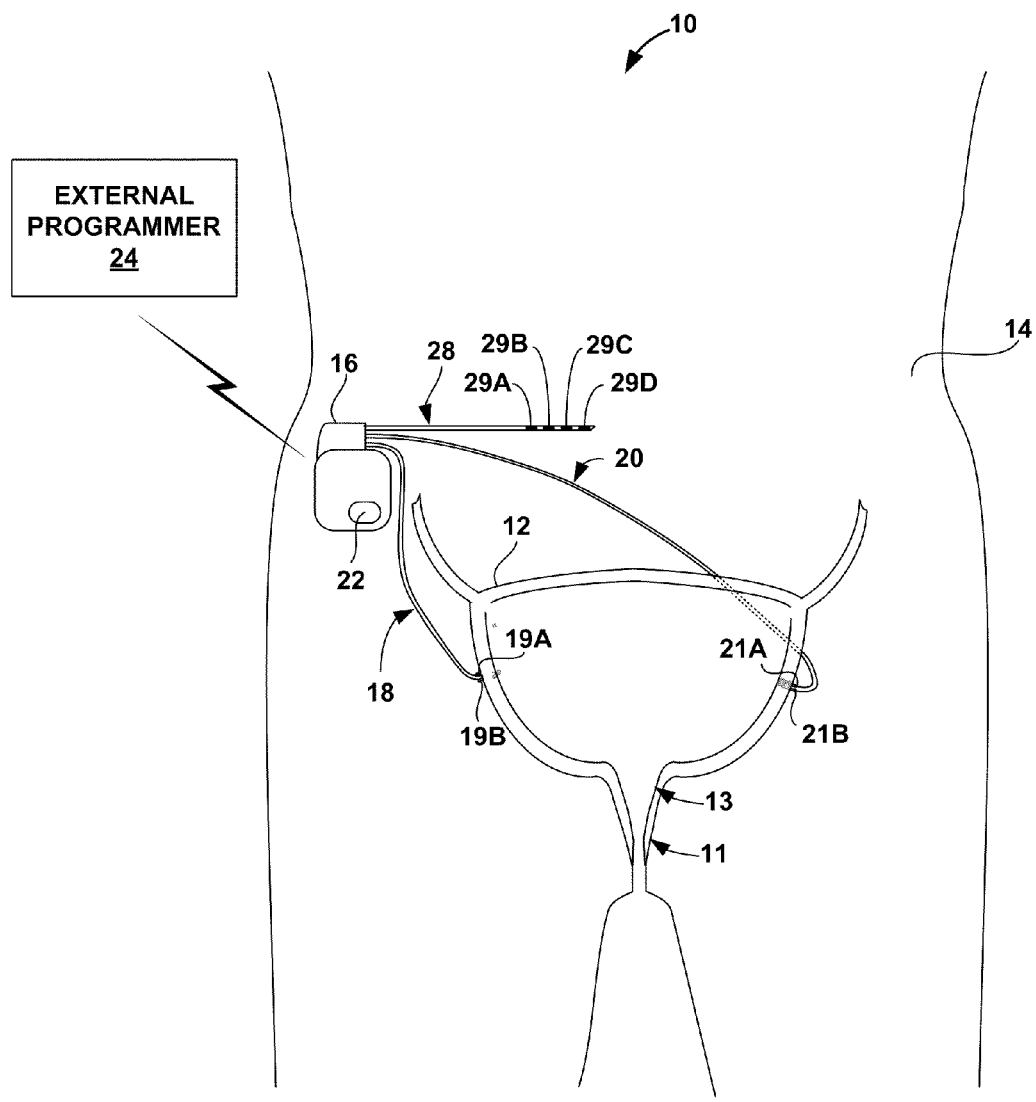
FIG. 1 is a conceptual diagram illustrating an example therapy system that delivers a first stimulation therapy to a patient and, when triggered, a second stimulation therapy to manage urinary incontinence.

Urinary incontinence refers to a condition of involuntary loss of urine, and may include urge urinary incontinence, stress incontinence, or both stress and urge incontinence, which may be referred to as mixed urinary incontinence. As used in this disclosure, the term "urinary incontinence" includes disorders in which urination occurs when not desired, such as stress or urge incontinence, and disorders in which urination does not occur as desired, such as urinary retention disorder. Stress or urge incontinence may also be referred to as overactive bladder or as leading to overactive bladder activities. Although therapies for treating urinary incontinence, such as electrical stimulation to the bladder for fluid retention, are effective, involuntary events may still occur.

One type of therapy for treating urinary incontinence includes delivery of electrical stimulation. For example, delivery of electrical stimulation from an implantable medical device to nerves in the pelvic floor, such as the sacral nerve, pudendal nerve, dorsal genital nerve, or branches of any of the aforementioned nerves may provide an effective therapy for urinary incontinence. Electrical stimulation of the sacral nerve may modulate afferent nerve activities to restore urinary function. In addition, electrical stimulation of the nerves innervating pelvic floor muscles may strengthen pelvic floor muscle and promote urinary continence.

Techniques described in this disclosure include delivering a first electrical stimulation therapy to a patient to generate a first physiological effect to manage urinary or fecal incontinence and, when triggered, delivering a second electrical stimulation therapy to generate a second physiological effect that further helps to prevent an occurrence of an involuntary urinary or fecal voiding event. The second stimulation therapy may, therefore, provide an additional safeguard against the occurrence of an involuntary voiding event in situations in which the involuntary voiding event may be likely to occur. In some cases, only the second stimulation therapy is delivered to the patient to manage urinary or fecal incontinence.

The first stimulation therapy, which may also be referred to as a base stimulation therapy, may be a chronic (e.g., non-temporary) therapy delivered to the patient to control urinary or fecal incontinence. In general, the first electrical stimulation therapy is delivered on a substantially regular basis to manage patient incontinence. In some examples, the first electrical stimulation is delivered to a patient in an open loop, i.e., without the use of an external feedback mechanism such as a sensor. However, in some cases, a sensor signal or patient input may be used to adjust the stimulation parameters of the first stimulation therapy.

The second electrical stimulation therapy may be referred to as a temporary stimulation therapy because the second electrical stimulation therapy is delivered for a predetermined period of time (e.g., a duration of time), rather than on a regular basis. In some examples, the predetermined period of time may be controlled by the patient. In addition, the second stimulation therapy may be referred to as functional electrical stimulation because the second electrical stimulation therapy results in a movement of muscles of the patient that provides a specific functional result. For example, the second stimulation therapy may generate a contraction of the urinary or anal sphincter of a patient. The second stimulation therapy may also be referred to as "boost" therapy because of the additional "boost" of therapy compared to the first stimulation therapy provided by the second electrical stimulation. In examples described herein, the second stimulation therapy is delivered to the patient in a closed loop manner because the initiation of the delivery of the second stimulation therapy is dependent upon an occurrence of a trigger event, as described in further detail below.

In some examples, an implantable medical device (IMD) delivers the first and second stimulation according to different sets of stimulation parameters and/or to different target tissue sites within the patient. However, in some examples, the first and second stimulation therapies are delivered to the same nerve (e.g., the sacral or pudendal nerve).

In some examples, the IMD may deliver the first stimulation therapy to a sacral nerve to improve pelvic floor muscle tone or to an afferent fiber of the sacral or pudendal nerves to inhibit bladder contractions, e.g., to relax the bladder. In addition, in some examples, the first stimulation therapy helps close or maintain internal urinary sphincter closure or urethral tone. The IMD may deliver the second stimulation therapy to a hypogastric nerve, a pudendal nerve, a dorsal penile nerve in a male patient, a dorsal clitoral nerve in a female patient, or to the external urinary sphincter or any combination thereof to promote contraction of the internal urinary sphincter, or promote external urinary sphincter closure or periurethral muscle contraction. In some examples, the second stimulation therapy may be viewed as a short-term boost to the effectiveness of the first stimulation therapy.

The second stimulation therapy may be triggered when a patient condition indicative of an imminent involuntary voiding event or an increase in a possibility that the involuntary voiding event will occur is detected. The patient condition may be, for example, a bladder contraction. The bladder contraction may be detected via any suitable sensing mechanism or under the control of the patient. For example, the IMD may detect bladder contraction based on bladder impedance, bladder pressure, pudendal or sacral afferent nerve signals, external urinary sphincter or anal sphincter electromyogram (EMG), motion sensor signals (e.g., accelerometer signals), or any combination thereof. Instead of or in addition to a bladder contraction, the patient condition may be an abnormal detrusor muscle activity.

In other examples, the trigger event for activating the delivery of the second stimulation therapy may be patient input. In some examples described herein, the patient may use a medical device programmer or another input mechanism to trigger the IMD to deliver the second stimulation therapy, e.g., when the patient perceives an imminent voiding event or undertakes an activity that may increase a possibility that an involuntary voiding event will occur. In the case of stress incontinence, for example, the patient may request a boost of therapy when the patient undertakes a relatively rigorous physical activity such as running or lifting. In some examples, the patient may also use the programmer to manually abort the delivery of the second stimulation therapy. In such examples, the IMD may wirelessly communicate with the programmer to alert that patient of prospective delivery of the second electrical stimulation. In additional examples, the patient may use the programmer to inhibit second electrical stimulation therapy during voluntary voiding events.

Other techniques described in this disclosure include generating objective incontinence information based on trigger event data (e.g., the occurrence of the trigger event, the time of a trigger event, a therapy program implemented by the IMD when a trigger event occurred, and the like), and presenting the objective incontinence information to a user. The objective incontinence information generated based on trigger event data may be useful for, for example, evaluating a patient condition (e.g., the disease progression), evaluating and/or adjusting stimulation therapy efficacy, selecting a therapy program from a plurality of therapy programs, and the like. The trigger event data generated with the systems described herein that deliver first and second stimulation therapies provides robust information from which various parameters of the patient incontinence condition and voiding event information can be determined. For example, the occurrence of trigger events may generally be indicative of at least one of the occurrence and frequency of voluntary voiding events, occurrences and frequency of urgency and/or detrusor overactivity, bladder contraction durations, severity of a particular urgency event, or bladder capacity. As described below, these types of information can be generated based on the occurrence and timing of trigger events.

As examples, the time between trigger events may be used to determine the frequency of sense of urgency and/or detrusor overactivity, the duration of each trigger event (e.g., when the trigger event is a prolonged request for the second stimulation therapy program or "boost") may be used to identify the duration of each contraction, and the time between voiding and a trigger event may be used to determine a bladder capacity. This objective incontinence information regarding the patient's condition may be useful for monitoring the progress of the patient incontinence, evaluate the efficacy of the incontinence therapy, and/or adjust stimulation therapy.

The trigger event data may be used to generate objective incontinence information about the patient. Some patients maintain a voiding diary that tracks various voiding parameters, such as when the patient felt a urgency event, when the patient felt an imminent voiding event, when the patient undertook an activity that increased a possibility that a voiding event will occur, and the like. While the voiding diary maintained by a patient may be useful, such a voiding diary may be problematic with some patients because the diary relies on the patient's subjective perception, e.g., of his or her bladder health, as well as relies on the patient to remember to record the voiding information for later analysis by a clinician and to be thorough. In contrast to these voiding diaries that rely on the maintenance of a manual diary by the patient, the trigger event data described herein is used to generate incontinence information (e.g., the times at which the patient perceives an imminent involuntary voiding event, undertakes an activity that increases the possibility of an involuntary voiding event, the bladder capacity of the patient, the severity of an urgency event perceived by the patient, and the like) that is both relatively thorough and consistent, as well as objective because the incontinence information is generated based on factual data (actual occurrences of trigger events) and does not rely on the personal feelings, interpretations, or prejudice of the patient.

In some examples, the objective incontinence information is displayed on a user interface of an external programmer or other display device. This information may be displayed in different formats, e.g., graphical, numerical, or textual, which can be selected by the user or automatically determined based on the type of requested information. For example, the objective incontinence information may be displayed as a bar graph of the number of trigger event clusters per day. Each detection of a trigger event may not necessarily be associated with a separate occurrence of an imminent incontinence event or an incontinence event. Instead, some trigger events may be a segment of a common incontinence event (imminent, actual or otherwise) and, in some examples, these trigger events can be clustered together. The concept of clustering is described in commonly assigned U.S. Pat. No. 7,280,867 to Frei et al., which is entitled "CLUSTERING OF RECORDED PATIENT NEUROLOGICAL ACTIVITY TO DETERMINE LENGTH OF A NEUROLOGICAL EVENT" and issued on Oct. 9, 2007. U.S. Pat. No. 7,280,867 to Frei et al. is incorporated herein by reference in its entirety.

Trigger events may also be associated with a time of day, e.g., day or night, when the patient is sleeping or awake, a type of patient activity, or other physiological conditions. In this manner, the objective incontinence information may be a source of information with which a user (e.g., a clinician or physician) may use diagnose the patient's incontinence and/or determine for effective methods of treatment.

In addition, in some examples, the objective incontinence information may used to adjust the first stimulation therapy, e.g., the chronic therapy. For example, two or more therapy programs may be evaluated by the patient for efficacy. When the IMD delivers therapy to the patient according to a particular therapy program, any trigger events occurring during use of the specific therapy program are associated with that active therapy program in a memory (e.g., of the IMD and/or a programmer or another computing device). After the system associates trigger events with each therapy program, objective incontinence information is generated based on the trigger events and associated therapy programs, and the objective incontinence information may be presented to the user. In one example, the user interface may present suggested therapy programs based upon the number or frequency of trigger events for each therapy program. In another example, the system may automatically select the therapy program with the fewest or least frequent associated trigger events. If the trigger event number and/or frequency do not decrease after using the newly selected therapy program, the system may automatically select another therapy program. In this manner, the system may use the objective incontinence information to select efficacious stimulation therapy.

Although the techniques are primarily described in this disclosure for managing urinary incontinence, the techniques may also be applied to manage fecal incontinence. In fecal incontinence examples, the IMD delivers the second stimulation therapy when patient input is received, when a patient parameter indicative of an imminent fecal incontinence event is detected or when a patient parameter indicative of an increased probability of an occurrence of a fecal incontinence event is detected (e.g., an increased patient activity level). The patient parameter may include, for example, contraction of the anal sphincter, patient activity level or patient posture state. The IMD may use any suitable sensing mechanism to detect contraction of the anal sphincter, such as a pressure sensor or an EMG sensor.

FIG. 1 is a conceptual diagram illustrating an example therapy system 10 that delivers a first electrical stimulation therapy to generate a first physiological response of patient 14 to manage a urinary continence disorder of patient 14, and, when triggered, a second electrical stimulation therapy to generate a second physiological response of patient 14. The delivery of the second stimulation therapy provides improved protection against the occurrence of involuntary voiding events. Therapy system 10 provides the first and second therapies to generate respective physiological responses in the form of electrical stimulation. In other examples, therapy system 10 may be configured to provide at least one of the first or second therapies to mange urinary incontinence by delivering a therapeutic agent to patient 14.

Therapy system 10 includes an implantable medical device (IMD) 16, which is coupled to leads 18, 20, and 28, sensor 22, and external programmer 24. IMD 16 generally operates as a therapy device that delivers electrical stimulation to, for example, a pelvic floor nerve, a pelvic floor muscle, the urinary sphincter, the anal sphincter, or other pelvic floor targets. Pelvic floor nerves include peripheral nerves such as sacral nerves, pudendal nerves and associated branches, and dorsal genital nerves. IMD 16 provides electrical stimulation therapy to patient 14 by generating and delivering a programmable electrical stimulation signal (e.g., in the form of electrical pulses) to a target therapy site by lead 28 and, more particularly, via electrodes 29A-29D (collectively referred to as "electrodes 29") disposed proximate to a distal end of lead 28.

IMD 16 delivers the first stimulation therapy periodically over an extended period of time, e.g., chronic stimulation, and automatically delivers the second stimulation therapy within that period of time and in response to a trigger event. The second stimulation therapy is delivered for a predetermined duration of time, referred to herein as a therapy period. In other examples, IMD 16 delivers the second stimulation therapy for a period of time controlled by the patient. The first and second stimulation therapies may be delivered at substantially the same time, during overlapping time slots, or in different time slots, such that IMD 16 only delivers one type of stimulation therapy at a time. In examples in which IMD 16 delivers one type of stimulation therapy at a time, IMD 16 may deliver the first stimulation therapy, and, when triggered, deactivate delivery of the first stimulation therapy and activate delivery of the second stimulation therapy. After the second stimulation therapy period, IMD 16 may revert back to delivering the first stimulation therapy until another trigger event for activating the delivery of the second stimulation therapy is detected.

A trigger event for activating the delivery of the second stimulation therapy may be detected based on sensor or patient input. As one example, IMD 16 may sense a bladder contraction that triggers IMD 16 to deliver the second stimulation therapy. As another example, patient 14 may use external programmer 24 to provide input that causes IMD 16 to deliver the second stimulation therapy. In this way, patient 14 may control delivery of the second stimulation therapy.

IMD 16 delivers a first stimulation therapy and a second stimulation therapy to patient 14 to generate different physiological responses. For example, the first stimulation therapy may generate an afferent response by the patient, whereas the second stimulation therapy generates an efferent response. In some examples, IMD 16 delivers the first stimulation therapy to a sacral nerve of patient 14 to generate an afferent response that relaxes bladder 12, e.g., by minimizing bladder contractions. In some examples, the delivery of the first stimulation therapy by IMD 16 results in the closure or maintains the closure of internal urinary sphincter 13 at the neck of bladder 12. In the example shown in FIG. 1, IMD 16 generates and delivers a first stimulation therapy and a second stimulation therapy to patient 14 according to different sets of stimulation parameters.

In addition, in some examples, IMD 16 delivers the second stimulation therapy to promote contraction of the internal urinary sphincter 13 and external urinary sphincter 11 or periurethral muscles (not shown). In some cases, it is undesirable for the external urinary sphincter or periurethral muscles to always remain closed, i.e., during the delivery of the chronic, first stimulation therapy. However, sphincter closure may help prevent the involuntary leakage of urine from bladder 12. Thus, the short-term closure of sphincter provided by the second stimulation therapy may help prevent the occurrence of involuntary voiding events during the occurrence of acute bladder contractions. In the example shown in FIG. 1, IMD 16 generates and delivers a first stimulation therapy and a second stimulation therapy to patient 14 according to different sets of stimulation parameters.

In the example of FIG. 1, IMD 16 delivers both the first and second stimulation therapies to patient 14 via electrodes 29 on lead 28. The target therapy site for the first and second stimulation therapies may be the same in some examples, such as the different fibers of the same nerve. In other examples, the target stimulation site for the first and second stimulation therapies may be different. For example, IMD 16 may deliver the first stimulation therapy to a sacral nerve of patient 14 to relax bladder 12 and deliver the second stimulation therapy to a hypogastric nerve to contract the internal urinary sphincter and external urinary sphincter or periurethral muscles, a pudendal nerve, a dorsal penile nerve in a male patient or a dorsal clitoral nerve in a female patient to contract the external urinary sphincter, periurethral muscles, the internal urinary sphincter, or any combination thereof. In other examples, IMD 16 may deliver the first stimulation therapy to a hypogastric nerve of patient 14 to close or maintain internal urinary sphincter closure or urethral tone.

IMD 16 may be surgically implanted in patient 14 at any suitable location within patient 14, such as near the pelvis. The implantation site may be a subcutaneous location in the side of the lower abdomen or the side of the lower back or upper buttocks. IMD 16 has a biocompatible housing, which may be formed from titanium, stainless steel, a liquid crystal polymer, or the like. The proximal ends of leads 18, 20, and 28 are both electrically and mechanically coupled to IMD 16 either directly or indirectly, e.g., via a respective lead extension. Electrical conductors disposed within the lead bodies of leads 18, 20, and 28 electrically connect sense electrodes (not shown) and stimulation electrodes, such as electrodes 29, to a therapy delivery module (e.g., a stimulation generator) within IMD 16. In the example of FIG. 1, leads 18 and 20 carry electrodes 19A, 19B (collective referred to as "electrodes 19") and electrodes 21A, 21B (collectively referred to as "electrodes 21"), respectively. As described in further detail below, electrodes 19 and 21 may be positioned for sensing an impedance of bladder 12, which may decrease as the volume of urine within bladder 12 increases.

One or more medical leads, e.g., leads 18, 20, and 28, may be connected to IMD 16 and surgically or percutaneously tunneled to place one or more electrodes carried by a distal end of the respective lead at a desired pelvic nerve or muscle site, i.e., one of the previously listed target therapy sites such as a sacral or pudendal nerve. For example, lead 28 may be positioned such that electrodes 29 deliver a first type of stimulation therapy to a sacral or pudendal nerve to relax bladder 12 and deliver the second type of stimulation therapy to hypogastric nerve, a pudendal nerve, a dorsal penile/clitoral nerve, the urinary sphincter, or any combination thereof to a promote closure of a urinary sphincter of patient 14. In FIG. 1, leads 18 and 20 are placed proximate to an exterior surface of the wall of bladder 12 at first and second locations, respectively. Electrodes 29 of the common lead 28 may deliver stimulation to the same or different nerves. In other examples of therapy system 10, IMD 16 may be coupled to more than one lead that includes electrodes for delivery of electrical stimulation to different stimulation sites within patient 14, e.g., to target different nerves.

In the example shown in FIG. 1, leads 18, 20, 28 are cylindrical. Electrodes 19, 20, 29 of leads 18, 20, 28, respectively, may be ring electrodes, segmented electrodes or partial ring electrodes. Segmented and partial ring electrodes each extend along an arc less than 360 degrees (e.g., 90-120 degrees) around the outer perimeter of the respective lead 18, 20, 28. In examples, one or more of leads 18, 20, 28 may be, at least in part, paddle-shaped (i.e., a "paddle" lead). In some examples, segmented electrodes 29 of lead 28 may be useful for targeting different fibers of the same or different nerves to generate different physiological effects for the first and second stimulation therapies. As described in further detail below, segmented electrodes may be useful for delivering relatively high frequency stimulation (e.g., about 66 Hertz) and relatively low frequency stimulation (e.g., about 15 Hertz) to activate both fast twitch muscles and low twitch muscles substantially simultaneously or at alternating time slots.

In some examples, one or more of electrodes 19, 20, 29 may be cuff electrodes that are configured to extend at least partially around a nerve (e.g., extend axially around an outer surface of a nerve). Delivering stimulation via one or more cuff electrodes and/or segmented electrodes may help achieve a more uniform electrical field or activation field distribution relative to the nerve, which may help minimize discomfort to patient 14 that results from the delivery of the first and/or second stimulation therapies. An electrical field represents the areas of a patient anatomical region that will be covered by an electrical field during delivery of stimulation therapy to tissue within patient 14. The electrical field may define the volume of tissue that is affected when the electrodes 19, 20, 29 are activated. An activation field represents the neurons that will be activated by the electrical field in the neural tissue proximate to the activated electrodes.

In some cases, patient 14 may perceive the delivery of the second stimulation therapy because of the increased intensity (e.g., increased amplitude and/or frequency) compared to the first stimulation therapy. The increased intensity of the second stimulation therapy may result in a change in an electrical field and/or activation field that is generated via the stimulation therapy compared to the delivery of the first stimulation therapy. Delivering the first and/or second stimulation therapies via cuff and/or segmented electrodes to achieve a more uniform electrical field or activation field distribution may help decrease changes in the intensity of therapy delivery perceived by patient 14.

The illustrated numbers and configurations of leads 18, 20, and 28 and electrodes carried by leads 18, 20, and 28 are merely exemplary. Other configurations, i.e., number and position of leads and electrodes are possible. For example, in other examples, IMD 16 may be coupled to additional leads or lead segments having one or more electrodes positioned at different locations in the pelvic region of patient 14. The additional leads may be used for delivering first or second stimulation therapies to respective stimulation sites within patient 14 or for monitoring physiological parameters of patient 14. As an example, in an example in which the target therapy sites for the first and second stimulation therapies are different, IMD 16 may be coupled to two or more leads, e.g., for bilateral or multi-lateral stimulation.

As previously indicated, IMD 16 generates and delivers a first electrical stimulation therapy to a patient to generate a first physiological effect to manage urinary or fecal incontinence and, when triggered, a second electrical stimulation therapy to provide an additional boost of therapy that generates a second physiological effect to help further manage urinary or fecal incontinence. IMD 16 controls the delivery of the second electrical stimulation therapy based on input received from patient 14 or a sensor that generates a signal indicative of a parameter of patient 14 relating to urinary incontinence, e.g., relating to a bladder condition, or fecal incontinence. As one example, IMD 16 may deliver the second stimulation therapy in response to detecting bladder contraction based on bladder impedance, bladder pressure, pudendal or sacral afferent nerve signals, a urinary sphincter EMG, or any combination thereof. As another example, IMD 16 may deliver the second stimulation therapy in response to detecting a patient activity level or patient posture state, with a sensor, which is indicative of an increased probability of an occurrence of an involuntary voiding event.

In some examples, IMD 16 may deliver the second stimulation therapy in response to receiving patient input. In this way, patient 14 may use external programmer 24 to trigger IMD 16 to deliver the second stimulation therapy. Patient 14 may initiate the delivery of the second stimulation therapy for many reasons. In some cases, patient 14 may be afflicted with urge incontinence, and upon perceiving an urge to void, patient 14 may provide input that causes IMD 16 to deliver the second stimulation therapy. The second stimulation therapy provides an additional "boost" of stimulation that helps prevent the leakage of urine from bladder 12, e.g., by contracting internal urinary sphincter 13 and the external urinary sphincter 11. In this way, therapy system 10 provides patient 14 with direct control of the incontinence therapy.

IMD 16 delivers both the first and second stimulation therapies via electrodes 29 on lead 28. In the example shown in FIG. 1, IMD 16 delivers the second stimulation therapy to generate the second physiological response when contraction of bladder 12 exceeding a particular threshold is detected. In the illustrated example of FIG. 1, IMD 16 determines an impedance through bladder 12, which varies as a function of the contraction of bladder 12, via electrodes 19 and 21 on leads 18 and 20, respectively. In the example shown in FIG. 1, IMD 16 determines bladder impedance using a four-wire (or Kelvin) measurement technique. In other examples, IMD 16 may measure bladder impedance using a two-wire sensing arrangement. In either case, IMD 16 may transmit an electrical measurement signal, such as a current, through bladder 12 via leads 18 and 20, and determine bladder impedance based on the transmitted electrical signal.

In the example four-wire arrangement shown in FIG. 1, electrodes 19A and 21A and electrodes 19B and 21B, may be located substantially opposite each other relative to the center of bladder 12. For example electrodes 19A and 21A may be placed on opposing sides of bladder 12, either anterior and posterior or left and right. In FIG. 1, electrodes 19 and 21 are shown placed proximate to an exterior surface of the wall of bladder 12. In some examples, electrodes 18 and 21 may be sutured or otherwise affixed to the bladder wall. In other examples, electrodes 19 and 21 may be implanted within the bladder wall. To measure the impedance of bladder 12, IMD 16 may source an electrical signal, such as current, to electrode 19A via lead 18, while electrode 21A via lead 20 sinks the electrical signal. IMD 16 may then determine the voltage between electrode 19B and electrode 21B via leads 18 and 20, respectively. IMD 16 determines the impedance of bladder 12 using a known value of the electrical signal sourced the determined voltage.

In the example of FIG. 1, IMD 16 also includes a sensor 22 for detecting changes in the contraction of bladder 12. Sensor 22 may be, for example, a pressure sensor for detecting changes in bladder pressure, electrodes for sensing pudendal or sacral afferent nerve signals, or electrodes for sensing urinary sphincter EMG signals (or anal sphincter EMG signals in examples in which therapy system 10 provides therapy to manage fecal incontinence), or any combination thereof. In examples in which sensor 22 is a pressure sensor, the pressure sensor may be a remote sensor that wireless transmits signals to IMD 16 or may be carried on one of leads 18, 20, or 28 or an additional lead coupled to IMD 16. In examples in which sensor 22 is one or more electrodes for sensing afferent nerve signals, the sense electrodes may be carried on one of leads 18, 20, or 28 or an additional lead coupled to IMD 16. In examples in which sensor 22 is one or more sense electrodes for generating a urinary sphincter EMG, the sense electrodes may be carried on one of leads 18, 20, or 28 or additional leads coupled to IMD 16. In any case, IMD 16 may deliver control the timing of the delivery of the second stimulation therapy based on input received from sensor 22.

In other examples, sensor 22 may comprise a patient motion sensor that generates a signal indicative of patient activity level or posture state. In some examples, IMD 16 controls the delivery of the second stimulation therapy to patient 14 upon detecting a patient activity level exceeding a particular threshold based on the signal from the motion sensor. The patient activity level that is greater than or equal to a threshold (which may be stored in a memory of IMD 16) may indicate that there is an increase in the probability that an incontinence event will occur, and, therefore, the additional boost of stimulation therapy provided by the second stimulation therapy is desirable. In this way, the second stimulation therapy provided by IMD 16 and the second physiological effect provided by the second stimulation therapy (e.g., the contraction of external urinary sphincter 11) may be useful for reacting to the circumstances that may affect patient incontinence and provide an additional layer of therapy to help prevent the occurrence of an involuntary voiding event.

In other examples, IMD 16 controls the delivery of the second stimulation therapy to patient 14 upon detecting a posture state associated with a high probability of an occurrence of an incontinence event based on the signal from the motion sensor. For example, patient 14 may be more prone to an incontinence event when patient 14 is in an upright posture state compared to a lying down posture state. IMD 16 may, for example, store a plurality of motion sensor signals and associate the signals with particular patient posture states using any suitable technique. IMD 16 may flag some of the posture states as being posture states for which additional therapy to help prevent the occurrence of an incontinence event is desirable.

System 10 may also include an external programmer 24, as shown in FIG. 1. In some examples, programmer 24 may be a wearable communication device, with boost function (e.g., activation of the second stimulation therapy) integrated into a key fob or a wrist watch, handheld computing device, computer workstation, or networked computing device. Programmer 24 may include a user interface that receives input from a user (e.g., patient 14, a patient caretaker or a clinician). The user interface may include, for example, a dedicated "boost button" to receive and confirm therapy delivery according to the second stimulation therapy, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display. It should be noted that the user may also interact with programmer 24 and/or ICD 16 remotely via a networked computing device.

Patient 14 may interact with programmer 24 to control IMD 16 to deliver the second stimulation therapy, to manually abort the delivery of the second stimulation therapy by IMD 16 while IMD 16 is delivery the therapy or is about to deliver the therapy, or to inhibit the delivery of the second stimulation therapy by IMD 16, e.g., during voluntary voiding events. Patient 14 may, for example, use a keypad or touch screen of programmer 24 to cause IMD 16 to deliver the second stimulation therapy, such as when patient 14 senses that a leaking episode may be imminent. In this way, patient 14 may use programmer 24 to control the delivery of the second stimulation therapy "on demand," e.g., when an extra boost of the stimulation therapy is desirable.

In some examples, patient 14 may interact with IMD 16 (e.g., via programmer 24 or directly via IMD 16) to control IMD 16 to deliver the second stimulation therapy, manually abort the delivery of the second stimulation therapy, or inhibit the delivery of the second stimulation therapy. In such examples, a motion sensor can be integrated into or on a housing of IMD 16, whereby the motion sensor generates a signal that is indicative of patient 14 tapping IMD 16 through the skin. The number, rate, or pattern of taps may be associated with the different programming capabilities, and IMD 16 may identify the tapping by patient 14 to determine when patient input is received. In this way, patient 14 may be able to directly control delivery of therapy in the event that programmer 24 is not within reach of patient 14.

In some examples, programmer 24 may provide a notification to patient 14 when the second stimulation therapy is being delivered or notify patient 14 of the prospective delivery of the second stimulation therapy to allow patient 14 to manually abort the second stimulation therapy. In such examples, programmer 24 may display a visible message, emit an audible alert signal or provide a somatosensory alert (e.g., by controlling a housing of programmer 24 to vibrate). After generating the notification, programmer 24 may wait for input from patient 14 prior to delivering the second stimulation therapy. Patient 14 may enter input that either confirms delivery of the second stimulation therapy is permitted or desirable, or manually aborts the prospective delivery of the second stimulation therapy. In the event that no input is received within a particular range of time, programmer 24 may wirelessly transmit a signal that indicates the absence of patient input to IMD 16. IMD 16 may then elect to deliver or not to deliver the second stimulation therapy based on the programming of IMD 16.

Patient 14 may also interact with programmer 24 to inhibit the delivery of the second stimulation therapy during voluntary voiding events. That is, patient 14 may use programmer 24 to enter input that indicates the patient will be voiding voluntarily. When IMD 16 receives the input from programmer 24, IMD 16 may suspend delivery the second stimulation therapy for a predetermined period of time, e.g., two minutes, to allow the patient to voluntarily void.

A user, such as a physician, technician, surgeon, electrophysiologist, or other clinician, may also interact with programmer 24 or another separate programmer (not shown), such as a clinician programmer to communicate with IMD 16. Such a user may interact with a programmer to retrieve physiological or diagnostic information from IMD 16. The user may also interact with a programmer to program IMD 16, e.g., select values for the stimulation parameter values with which IMD 16 generates and delivers stimulation and/or the other operational parameters of IMD 16. For example, the user may use a programmer to retrieve information from IMD 16 regarding the contraction of bladder 12 and voiding events. As another example, the user may use a programmer to retrieve information from IMD 16 regarding the performance or integrity of IMD 16 or other components of system 10, such as leads 18, 20, and 28, or a power source of IMD 16. In some examples, this information may be presented to the user as an alert if a system condition that may affect the efficacy of therapy is detected.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

IMD 16 does not deliver the second stimulation therapy to patient 14 on a predetermined, scheduled basis, but as needed. For example, IMD 16 can deliver the second stimulation therapy to patient 14 when a particular patient parameter (e.g., a physiological parameter, activity level or posture state) indicative of a high probability of an occurrence of an involuntary voiding event is detected or when patient input is received. In some examples, either IMD 16 or programmer 24 may track when IMD 16 delivers the second stimulation therapy to patient 14. Frequent delivery of the second stimulation therapy may be undesirable because, for example, muscle fatigue may result. Frequent delivery of the second stimulation therapy may indicate that, as another example, bladder 12 is full.

In some examples, programmer 24 may provide a notification to patient 14 when the second stimulation therapy is triggered too frequently. The notification may be triggered based on any suitable criteria, which may be determined by a clinician or automatically programmed into IMD 16 or programmer 24. For example, in the event that the second stimulation therapy is triggered five times within five minutes, programmer 24 may provide a notification to patient 14 indicating the same. This may allow patient 14 to proceed to a bathroom before a leaking episode occurs. The notification provided by programmer 24 may also direct patient 14 to voluntarily void.

Figure 2:
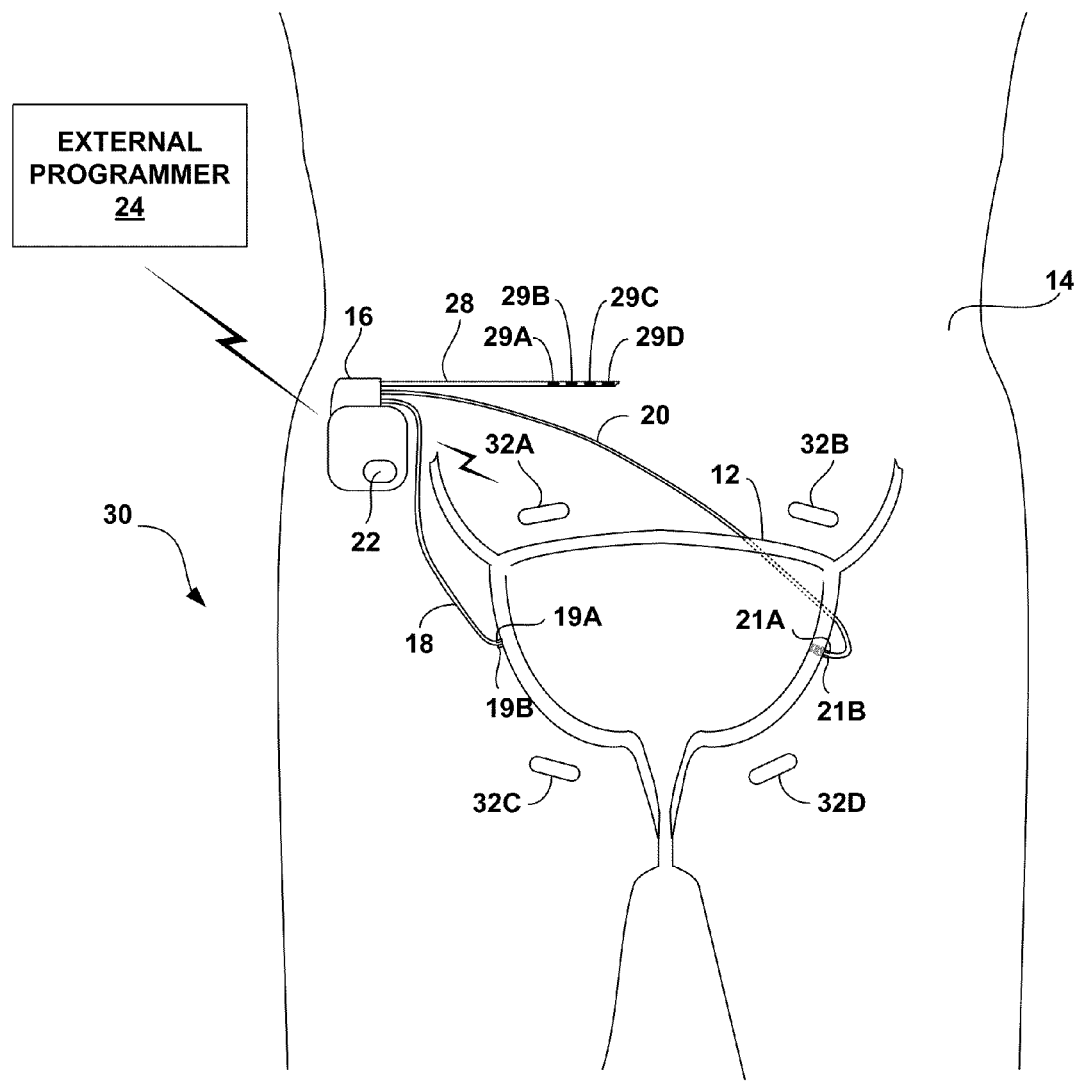
FIG. 2 is a conceptual diagram illustrating another example therapy system that delivers a first stimulation therapy and, when triggered, a second stimulation therapy to a patient to manage urinary incontinence.

FIG. 2 is conceptual diagram illustrating another example therapy system 30 that delivers a first stimulation therapy to provide a first physiological response to manage a urinary incontinence condition of patient 14, and a second stimulation therapy to provide a second, different physiological response to manage the urinary incontinence condition of patient 14. Therapy system 30 includes a distributed array of electrical stimulators, referred to herein as microstimulators 32A-32D (collectively referred to as "microstimulators 32"), in addition to IMD 16, leads 18, 20, and 28, sensor 22, and programmer 24. Microstimulators 32 are configured to generate and deliver electrical stimulation therapy to patient 14 vie one or more electrodes. Microstimulators 32 have a smaller size than IMD 16, and are typically leadless.

IMD 16 may deliver one or both of the first or second electrical stimulation therapies to patient 14 via microstimulators 32. For example, IMD 16 may communicate wirelessly with microstimulators 32 via wireless telemetry to control delivery of the first and/or second stimulation therapies via microstimulators 32. In the example of FIG. 2, microstimulators 32 are implanted at different target stimulation sites. For example, microstimulators 32A and 32B may be positioned to stimulate a different set of nerves than microstimulators 32C and 324D. As an example, microstimulators 32A and 32B may target sacral nerves, while microstimulators 32C and 32D target the pudendal nerve. In other examples, microstimulators 32 may be implanted at various locations within the pelvic floor region, e.g., at different positions in proximity to the sacrum to target different nerves within the pelvic region. The illustrated number and configuration of microstimulators 32 is merely exemplary. Other configurations, i.e., number and position of microstimulators, are possible.

Systems 10 and 30 shown in FIGS. 1 and 2, respectively, are merely examples of therapy systems that may provide a first stimulation therapy to provide a first physiological response to manage urinary or fecal incontinence, and a second stimulation therapy to provide a second, different physiological response to complement and "boost" the first stimulation therapy. Systems with other configurations of leads, electrodes, and sensors are possible. Additionally, in other examples, a system may include more than one IMD. For example, a system may include an IMD coupled to one or more leads for delivering the first stimulation therapy and another IMD coupled to one or more leads for delivering the second stimulation therapy.

Figure 3:
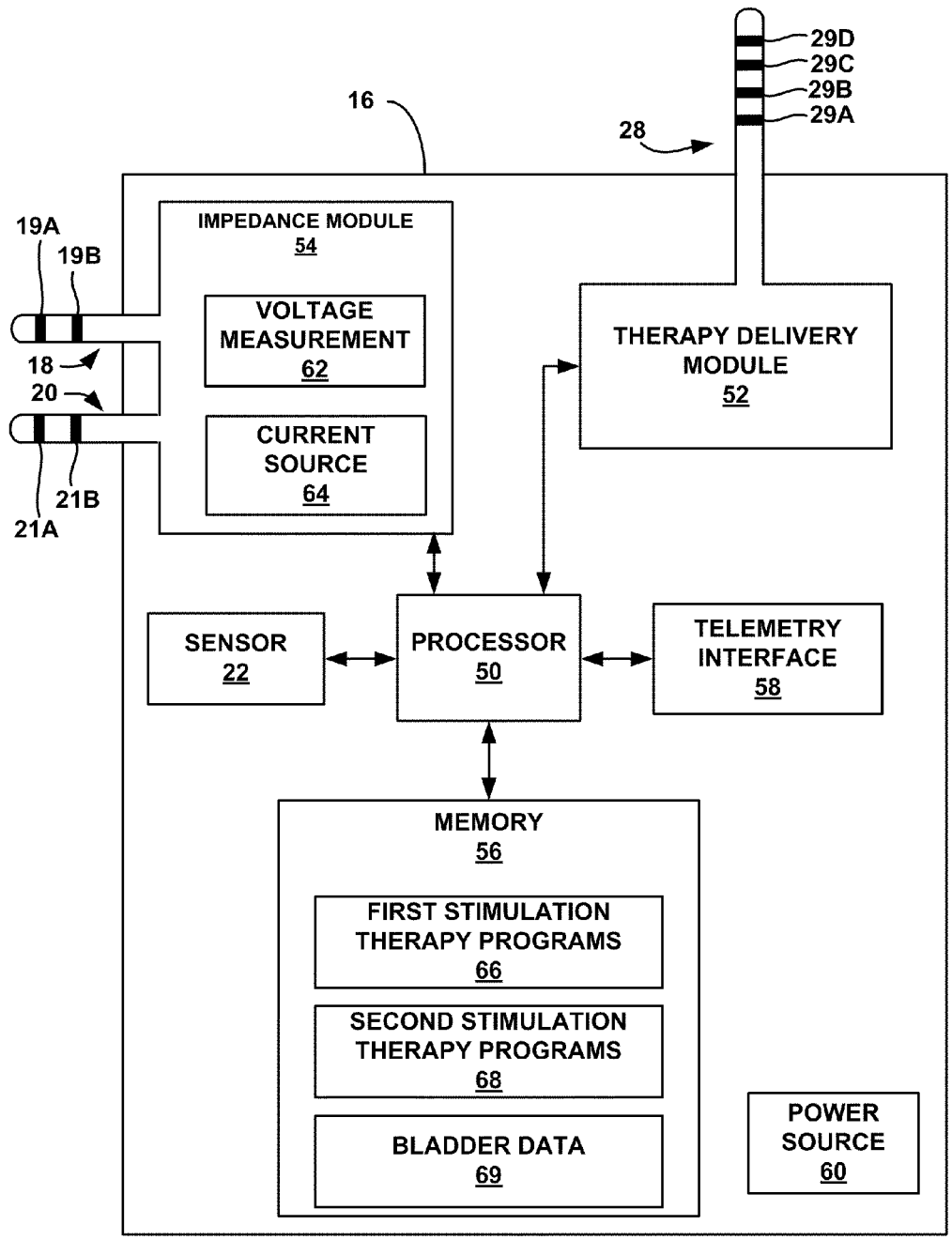
FIG. 3 is a block diagram illustrating an example configuration of the implantable medical device (IMD) of the systems shown in FIGS. 1 and 2.

FIG. 3 is a block diagram illustrating example components of IMD 16. In the example of FIG. 3, IMD 16 includes sensor 22, processor 50, therapy delivery module 52, impedance module 54, memory 56, telemetry module 58, and power source 60. Memory 56 stores first stimulation therapy programs 66 and second stimulation therapy programs 68 that specify stimulation parameters for the first and second stimulation therapies, respectively. Memory 56 also stores bladder data 69, which processor 50 may use for controlling the timing of the delivery of the second stimulation therapy. For example, bladder data 69 may include threshold values for one or more of bladder impedance, bladder pressure, sacral or pudendal afferent nerve signals, and external urinary sphincter or anal sphincter EMG templates.

Generally, therapy delivery module 52 generates and delivers therapy under the control of processor 50. In particular, processor 50 controls therapy delivery module 52 by accessing memory 56 to selectively accessing and loading first and second stimulation therapy programs 66, 68 to therapy delivery module 52. For example, in operation, processor 50 may access memory 56 to load one of first stimulation therapy programs 66 to therapy delivery module 52 and, when triggered, access memory 56 to load one of the second stimulation therapy programs 68 to therapy delivery module 52. Consistent with the techniques described in this disclosure, processor 50 may load one of second stimulation therapy programs 68 to therapy delivery module 52 based on input received from impedance module 54, sensor 22, or an indication of patient input received from another device and transmitted to IMD 16 via telemetry module 58.

By way of example, processor 50 may access memory 56 to load one of first stimulation therapy programs 66 to therapy module 52 for delivering the first stimulation therapy to patient 14. A clinician or patient 14 may select a particular one of first stimulation therapy programs 66 from a list using a programming device, such as programmer 24 or a clinician programmer. Processor 50 may receive the selection via telemetry module 58. Therapy delivery module 52 delivers the first stimulation therapy to patient 14 according to the selected program for an extended period of time, such as hours, days, weeks, or until patient 14 or a clinician manually stops or changes the program. The first stimulation therapy program 66 may define a schedule or an "on cycle" and "off cycle" duration for the first stimulation therapy, such that a stimulation signal is not continuously delivered to patient 14, but periodically delivered in accordance with predetermined parameters for the first stimulation therapy.

Upon detecting a condition in which the second stimulation therapy is desirable to help prevent the occurrence of an incontinence event, such as in response to detecting bladder contraction or receiving patient input, processor 50 accesses memory 56 to load one of second stimulation therapy programs 68 to therapy delivery module 52. Therapy delivery module 52 delivers the second stimulation therapy according to the selected program. In some examples, therapy module 52 delivers the second stimulation therapy for a predetermined therapy period, the duration of which may be stored in memory 56. The therapy period may be, for example, approximately 10 seconds to approximately 50 seconds, although other therapy periods are contemplated. That is, therapy delivery module 52 may deliver therapy according to second stimulation therapy programs 68 via bursts of stimulation for a duration of approximately 10 seconds to approximately 60 seconds and subsequently reverts to delivering therapy according to one of first stimulation therapy programs 66.

In some examples, therapy module 52 delivers the second stimulation therapy for a period of time controlled by the patient. In such examples, the patient may interact with programmer 24 to control the delivery time. As an example, IMD 16 may deliver the second stimulation therapy as long as the patient presses a "boost" button on a keypad or touch screen of programmer 24. In operation, processor 50 receives the patient input via telemetry module 58 and controls therapy delivery module 52 to deliver therapy according to the received input.

In other examples, such as examples in which IMD 16 delivers the second stimulation therapy based on a sensed patient condition, therapy module 52 delivers the second stimulation therapy until the condition is no longer detected. For example, IMD 16 may deliver the second stimulation therapy in response to detecting a bladder impedance greater than or equal to a predetermined threshold and continue delivering the second stimulation therapy until the bladder impedance is less than the predetermined threshold. If the second stimulation therapy is delivered for more than one consecutive therapy, IMD 16 may separate the consecutive therapy periods by at least a predetermined minimum inter-therapy interval. In some examples, the minimum inter-therapy interval is about 10 seconds, although other intervals are contemplated.

In some examples, IMD 16 delivers the second stimulation therapy at substantially the same time as the first stimulation therapy, such that the first and second physiological effects from the first and second stimulation therapy, respectively, overlap. In other examples, the first and second stimulation therapies are not delivered at the same time, such that IMD 16 only delivers one type of therapy at a time. The alternating therapies may be implemented if, for example, IMD 16 delivers the first and second stimulation therapies with a common set of electrodes. In the latter technique, when the second stimulation therapy has been delivered, IMD 16 may revert back to delivering the first stimulation therapy according to a first stimulation therapy program 66 selected from memory 56.

Therapy module 52 delivers therapy, i.e., electrical stimulation, according to stimulation parameters, such as voltage or current amplitude, pulse rate (frequency), and pulse width specified by therapy programs, such as first stimulation therapy programs 66 and second stimulation therapy programs 68. In some examples, therapy delivery module 52 delivers therapy in the form of electrical pulses. In other examples, therapy delivery module 52 delivers electrical stimulation in the form of continuous waveforms.

In some examples, the stimulation parameters for the first stimulation programs 66 may be selected to relax bladder 12 (FIG. 1) or close or maintain internal urinary sphincter closure or urethral tone. An example range of stimulation parameters for the first stimulation therapy that are likely to be effective in treating incontinence, e.g., when applied to the sacral or pudendal nerves, are as follows:

1. Frequency: between approximately 0.5 Hz and approximately 500 Hz, such as between approximately 10 Hz and approximately 250 Hz, or between approximately 10 Hz and approximately 25 Hz.

2. Amplitude: between approximately 0.1 volts and approximately 50 volts, such as between approximately 0.5 volts and approximately 20 volts, or between approximately 1 volt and approximately 10 volts.

3. Pulse Width: between approximately 10 microseconds ($\mu$s) and approximately 5000 $\mu$s, such as between approximately 100 $\mu$s and approximately 1000 $\mu$s, or between approximately 180 $\mu$s and approximately 450 $\mu$s.

The stimulation parameters for second stimulation therapy programs 68 are generally different than those for first stimulation therapy programs 66. Stimulation parameters for second stimulation therapy programs 68 may be selected to maximize closure of one or more of internal urinary sphincter, external urinary sphincter, and periurethral muscles. Stimulation parameters for second stimulation therapy programs 68 may also be selected to minimize muscle fatigue. Muscle fatigue may occur when the force-generating ability of a muscle decreases as a result of the electrical stimulation.

An example range of stimulation pulse parameters for the second stimulation therapy are as follows:

1. Frequency: between approximately 15 Hz to approximately 30 Hz to activate slow-twitch muscles to minimize muscle fatigue while providing some sphincter closure, and between approximately 30 Hz and approximately 66 Hz to activate fast-twitch muscles, which may maximize sphincter closure.

2. Amplitude: approximately 2-8 times rheobase (e.g., approximately 2-4 times rheobase) for the target nerve or muscle (e.g., the sphincter muscle), such as about 0.5 volts to about 50 volts, or about 0.5 volts to about 10 volts, or about 4 volts to about 8 volts. Rheobase is the minimal electric current of infinite duration that results in an action potential or muscle twitch.

3. Pulse Width: between about 10 microseconds ($\mu$s) and about 5,000 $\mu$s, such as between about 100 $\mu$s and approximately 1,000 $\mu$s.

As previously indicated, IMD 16 may deliver the second stimulation therapy for duration of time referred to as a therapy period. In some examples, the therapy period has a duration of about 10 seconds to about 50 seconds, although other therapy period durations are contemplated. In some examples, the therapy period duration is controlled by patient 14 through programmer 24, and may have a maximum period limit of about 3 minutes, although other maximum therapy periods for the second stimulation therapy is contemplated.

At least one of second stimulation therapy programs 68 may include more than one set of stimulation parameters. In such examples, one set of stimulation parameters may be designed to activate fast-twitch muscle fibers in order to maximize closure of the urinary sphincter and/or periurethral muscles, and another set of stimulation parameters may be designed to activate slow-twitch muscle fibers in order to maintain closure of the urinary sphincter and/or periurethral muscles while minimizing muscle fatigue. The fast-twitch and slow-twitch muscle fibers may be selectively activated by activating specific nerve fibers with the same electrodes of a common lead, or different electrodes of a common lead (e.g., segmented electrodes specifically selected to target particular nerve fibers) or electrodes of separate leads or microstimulators.

As an example, in accordance with one of the second stimulation therapy programs 68, IMD 16 may generate and deliver stimulation pulses having a relatively high frequency (e.g., about 66 Hz) for the first five seconds of the therapy interval to activate fast-twitch muscle fibers, and subsequently generate and deliver stimulation pulses at a lower relative frequency (e.g., 30 Hz) for the following 10 seconds to activate slow-twitch muscle fibers. An example stimulation signal that IMD 16 may generate and deliver as part of the second stimulation therapy is described with respect to in FIG. 11.

In some examples, the portion of the second stimulation therapy that activates the fast twitch muscles is delivered for a shorter duration of time than the portion of the second stimulation therapy that activates the slow twitch muscles. This may help minimize muscle fatigue by providing the fast twitch muscles with a longer recovery time. It has been found that some fast twitch muscles require a longer time to recover, e.g., to regain contraction force, following the delivery of stimulation, than slow twitch muscles. Muscles may be recovered when the contraction force under stimulation is close or substantially equal to the contraction force under the same stimulation intensity while there is no fatigue e.g., when the muscles are stimulated a first time after a relatively long time of rest in which no stimulation was delivered. If the muscle is stimulated again with the same therapy parameter values, and the contraction force is the same, then the muscle may be considered to have recovered from the previous delivery of stimulation.

In some examples, processor 50 may control the timing of the second stimulation therapy relative to the first stimulation therapy in a manner that minimizes muscle fatigue. For example, processor 50 may utilize an inter-therapy interval to prevent the second stimulation therapy from being delivered so frequently that the pelvic muscles fatigue and render second stimulation therapy less effective or even ineffective. The inter-therapy interval is a predetermined amount of time, e.g., 10 seconds, following a delivery of a therapy period of the second stimulation therapy during which IMD 16 cannot deliver a subsequent therapy period of the second stimulation therapy. In this way, in some examples, the second stimulation therapy cannot be triggered within a minimal inter-therapy interval following previously delivered second stimulation therapy to prevent muscle fatigue. Thus, if the second stimulation therapy is triggered within the inter-therapy interval (e.g., based on a sensed patient parameter or patient input) processor 50 of IMD 16 may control therapy delivery module 52 to generate and deliver the second stimulation therapy only after the inter-therapy interval has lapsed. Alternatively, processor 50 may ignore sensor input (e.g., input from impedance module 54) or patient input received via telemetry module 58 for the duration of the inter-therapy interval. An example of the application of the inter-therapy interval is provided in FIG. 12.

In some examples, processor 50 may adjust a second stimulation therapy program 68 for one or more consecutive therapy periods to configure the second stimulation therapy to minimize muscle fatigue. In this way, IMD 16 may provide second stimulation therapy that is delivered in an adaptive fashion. In some examples, processor 50 may implement an inter-therapy interval, but rather than abstaining from delivery of the second stimulation therapy when the second stimulation therapy is triggered within an inter-therapy interval, processor 50 controls therapy delivery module 52 to generate and deliver stimulation according to an adjusted second stimulation therapy.

As one example, if second stimulation therapy is triggered within the inter-therapy interval following the delivery of a previous second stimulation therapy, the adaptive stimulation program may decrease the duration of fast-twitch muscle stimulation defined by the previously-implemented second stimulation therapy program by a first time increment (e.g., five seconds) and increase the duration of slow-twitch muscle stimulation by the same or different time increment. As another example, for each second stimulation therapy triggered within an inter-therapy interval, the adaptive stimulation program may replace the first five second of fast-twitch muscle stimulation by five second of slow-twitch muscle stimulation compared to the previously delivered the second stimulation therapy signal. Example adaptive stimulation signals that may be delivered as part of the second stimulation therapy are described below with respect to FIGS. 13A-13C and 14A-14C.

In other examples, second stimulation therapy programs 68 may define the simultaneous delivery of stimulation at multiple frequencies. As an example, a stored second stimulation therapy program 68 may define segmented electrodes to simultaneously deliver higher frequency (e.g., 66 Hz) stimulation to fascicles responsible for fast muscles, such as the Iliococcygeus muscle and the pubococcygeus muscle, and lower frequency stimulation (e.g., 30 Hz) to fascicles responsible for slow muscles, such as the soleus muscle.

In the example of FIG. 3, therapy delivery module 52 drives a single lead 28. Specifically, therapy delivery module 52 delivers electrical stimulation to tissue of patient 14 via selected electrodes 29A-29D carried by lead 28. A proximal end of lead 28 extends from the housing of IMD 16 and a distal end of lead 28 extends to target therapy sites within the pelvic floor, such as tissue sites proximate a sacral nerve, a pudendal nerve, a hypogastric nerve, a urinary sphincter, or any combination thereof. In other examples, therapy delivery module 52 may deliver electrical stimulation with electrodes on more than one lead and each of the leads may carry one or more electrodes. The leads may be configured as an axial leads with ring electrodes and/or paddle leads with electrode pads arranged in a two-dimensional array. The electrodes may operate in a bipolar or multi-polar configuration with other electrodes, or may operate in a unipolar configuration referenced to an electrode carried by the device housing or "can" of IMD 16. In yet other examples, such as system 30 shown in FIG. 2 that includes microstimulators 32, processor 50 may act as a "master" module that controls microstimulators to deliver stimulation at target therapy sites. In other examples, however, one of microstimulators 32 may act as a master module or microstimulators 32 may be self-controlled.

In some examples, processor 50 controls therapy module 52 to deliver the second stimulation therapy to patient 14 based on signals received from impedance module 54, sensor 22, or patient input received via telemetry module 58. In the example shown in FIG. 3, processor 50 monitors bladder impedance to detect bladder contraction based on signals received from impedance module 54. For example, processor 50 may determine an impedance value based on signals received from impedance module 54 and compare the determined impedance value to a threshold impedance value stored in memory 56 as bladder data 69. When the determined impedance value is less than the threshold value stored in bladder data 69, processor 50 detects bladder contraction and loads one of second stimulation therapy programs 68 in therapy module 52, and therapy module 52 generates and delivers the second stimulation therapy to patient 14 to generate a physiological response that helps prevent an incontinence event. As previously indicated, the physiological response generated by the delivery of the second stimulation therapy differs from the physiological response generated by the delivery of the first stimulation therapy to provide an additional layer of incontinence prevention.

In the example of FIG. 3, impedance module 54 includes voltage measurement circuitry 62 and current source 64, and may include an oscillator (not shown) or the like for producing an alternating signal, as is known. In some examples, as described above with respect to FIG. 1, impedance module 54 may use a four-wire, or Kelvin, arrangement. As an example, processor 50 may periodically control current source 64 to, for example, source an electrical current signal through electrode 19A and sink the electrical current signal through electrode 21A. In some examples, for collection of impedance measurements, current source 64 may deliver electrical current signals that do not deliver stimulation therapy to bladder 12, e.g., sub-threshold signals, due to, for example, the amplitudes or widths of such signals and/or the timing of delivery of such signals. Impedance module 54 may also include a switching module (not shown) for selectively coupling electrodes 19A, 19B, 21A, and 21B to current source 64 and voltage measurement circuitry 62. Voltage measurement circuitry 62 may measure the voltage between electrodes 19B and 21B. Voltage measurement circuitry 62 may include sample and hold circuitry or other suitable circuitry for measuring voltage amplitudes. Processor 50 determines an impedance value from the measure voltage values received from voltage measurement circuitry 52.

As previously described, sensor 22 may be a pressure sensor for detecting changes in bladder pressure, electrodes for sensing pudendal or sacral afferent nerve signals, or electrodes for sensing external urinary sphincter EMG signals (or anal sphincter signals in examples in which IMD 16 provides fecal incontinence therapy), or any combination thereof. Alternatively, sensor 22 may be a motion sensor, such as a two-axis accelerometer, three-axis accelerometer, one or more gyroscopes, pressure transducers, piezoelectric crystals, or other sensors that generate a signal that changes as patient activity level or posture state changes. Processor 50 may detect a patient condition indicative of a high probability of an incontinence event (e.g., bladder contraction or abnormal detrusor muscle activity) or other trigger events based on signals received from sensor 22 in addition to instead of impedance module 54. Sensor 22 may also be a motion sensor that is responsive to tapping (e.g., by patient 14) on skin superior to IMD 16 and, as previously described, processor 50 may control therapy module 52 to deliver second stimulation therapy, manually abort delivery of second stimulation therapy, or inhibit the delivery of second stimulation therapy, in response to detection of the patient tapping.

One type of bladder contraction detection algorithm indicates an occurrence of a bladder contraction for which delivery of the second stimulation therapy is desirable upon sensing of a signal that exhibits a certain characteristic, which may be a time domain characteristic (e.g., an amplitude) or a frequency domain characteristic (e.g., an energy level in one or more frequency bands). For example, the bladder contraction detection algorithm may indicate the occurrence of a bladder contraction for which delivery of the second stimulation therapy is desirable when the amplitude of the signal from sensor 22 meets a certain condition relative to a threshold (e.g., is greater than, equal to or less than the threshold). Another bladder contraction detection algorithm indicates the occurrence of a bladder contraction for which delivery of the second stimulation therapy is desirable if a sensed signal substantially correlates to a signal template, e.g., in terms of frequency, amplitude and/or spectral energy characteristics. IMD 16 may use known techniques to correlate a sensed signal with a template in order to detect the bladder contraction or detect the bladder contraction based on the frequency domain characteristics of a sensed signal. Other bladder contraction techniques may be used.

In examples in which sensor 22 includes a pressure sensor, processor 50 may determine a pressure value based on signals received from the pressure sensor and compare the determined pressure value to a threshold value stored in bladder data 69 to determine whether the contractions of bladder 12 are indicative of an imminent incontinence event. In examples in which sensor 22 includes an EMG sensor, processor 50 may generate an EMG from the received signals generated by sensor 22 (e.g., which may sense the muscle activity with one or more sensor positioned near the target muscle) and compare the EMG to templates stored as bladder data to determine whether the contractions of bladder 12 are indicative of an imminent incontinence event. Alternatively, processor 50 may compare previously collected EMGs to a current EMG to detect changes over time. The techniques for detecting bladder contractions may also be applied to detecting abnormal detrusor muscle activities.

As described above, in examples in which processor 50 monitors a patient condition indicative of bladder contraction, processor 50 may control therapy delivery module 52 to generate and deliver the second stimulation therapy to generate the second physiological response only if the bladder contraction is greater than a threshold level. The threshold level may indicate a bladder contraction intensity (e.g., strength or frequency) that is indicative of an imminent involuntary voiding event or a relatively high probably an involuntary voiding event will occur. In some cases, the bladder contraction may be indicative of a voluntary voiding event. Thus, in some examples, processor 50 can control therapy delivery module 52 to generate and deliver the second stimulation therapy if the bladder contraction is greater than first threshold level, but less than a second threshold level.

In examples in which sensor 22 includes a motion sensor, processor 50 may determine a patient activity level or posture state based on a signal generated by sensor 22. For example, processor 50 may determine a patient activity level by sampling the signal from sensor 22 and determining a number of activity counts during a sample period, where a plurality of activity levels are associated with respective activity counts. In one example, processor 50 compares the signal generated by sensor 22 to one or more amplitude thresholds stored within memory 56, and identifies each threshold crossing as an activity count.

Processor 50 may determine a patient posture state based on a signal from sensor 22 using any suitable technique. In one example, a posture state may be defined as a three-dimensional space (e.g., a posture cone or toroid), and whenever a posture state parameter value, e.g., a vector from a three-axis accelerometer of sensor 22 resides within a predefined space, processor 50 indicates that patient 14 is in the posture state associated with the predefined space.

Memory 56 may associate patient posture states or activity levels with the second stimulation therapy, such that when processor 50 detects a posture state or activity level associated with the second stimulation therapy, processor 50 controls therapy delivery module 52 to generate and deliver the second stimulation therapy to patient 14. Certain posture states or activity levels may be associated with a higher incidence of incontinence events. For example, patient 14 may have less control of the pelvic floor muscles when occupying an upright posture state or when patient 14 is in a highly active state (e.g., as indicated by a stored activity count or a threshold activity signal value). Thus, detection of these activity levels or posture states may be triggers for the delivery of the second stimulation therapy.

The threshold values (also referred to as threshold levels) or templates (e.g., indicating a signal indicative of an imminent voiding event) stored in memory 56 as bladder data 69 may be determined using any suitable technique. In some examples, the threshold values may be determined during implantation of IMD 16 or during a trial period in a clinician's office following the implant procedure. For example, a clinician may record impedance values during involuntary voiding events and use the recorded impedance values or values calculated based on the recorded values as threshold values. These threshold values may be adapted over time based on user input, e.g., via external programmer 24. As an example, patient 14 may indicate, via programmer 24, when an involuntary voiding event takes place. When the patient input is received, processor 50 may determine an impedance value during the event or immediately prior to the event based in signals received from impedance module 54. A new threshold value may be determined using this impedance value. For example, the threshold value stored as bladder data 69 may be a running average of impedance values measured during involuntary voiding events.

In some examples, IMD 16 includes impedance sensing module 54 and not sensor 22, while in other examples, IMD 16 includes sensor 22, but not impedance sensing module 54. Moreover, in some examples, sensor 22 and/or impedance sensing module 54 may be physically separate from IMD 16. Physically separate sensors may be useful in examples in which either sensor 22 and/or impedance sensing module 54 sense one or more physiological parameters at a location that is not accessible by IMD 16 or difficult to access by IMD 16.

Processor 50 may control therapy delivery module 52 to deliver the second stimulation therapy based on patient input received via telemetry module 58. Telemetry module 58 includes any suitable hardware, firmware, software or any combination thereof for communicating with another device, such as programmer 24 (FIG. 1). Under the control of processor 50, telemetry module 58 may receive downlink telemetry, e.g., patient input, from and send uplink telemetry, e.g., an alert, to programmer 24 with the aid of an antenna, which may be internal and/or external. Processor 50 may provide the data to be uplinked to programmer 24 and the control signals for the telemetry circuit within telemetry module 58, and receive data from telemetry module 58.

Generally, processor 50 controls telemetry module 58 to exchange information with medical device programmer 24. Processor 50 may transmit operational information and receive stimulation programs or stimulation parameter adjustments via telemetry module 58. Also, in some examples, IMD 16 may communicate with other implanted devices, such as stimulators, control devices, or sensors, via telemetry module 58.

As previously described, telemetry module 58 may receive an indication that patient 14 provided input indicative of an imminent voiding event or a desire for delivery of the "boost" of stimulation, e.g., the second stimulation therapy, from programmer 24. Upon receiving the patient input via telemetry module 58, processor 50 may control therapy delivery module 52 to generate and deliver the second stimulation therapy for a predetermined amount of time or until a particular patient condition is detected, to manually abort the second stimulation therapy, or inhibit the second stimulation therapy during voluntary voiding. Processor 50 monitors patient input received via telemetry module 58 and takes appropriate action. For example, telemetry module 58 may receive input from programmer 24 that indicates a specified one of second stimulation therapy programs 68 should be selected for delivery of the second stimulation therapy program. Upon receiving the input, processor 50 loads the specified one of second stimulation therapy programs 68 to therapy module 52.

In an example in which telemetry module 58 receives patient input that indicates the second stimulation therapy should be aborted, processor 50 may transmit a signal to programmer 24 via telemetry module 58 to notify patient 14 of the prospective delivery of the second stimulation therapy. The notification may be provided, for example, within less than a minute (e.g., a few seconds) prior to the delivery of the second stimulation therapy. This notification provides patient 14 with the opportunity to intervene if the second stimulation therapy is not deemed necessary by patient 14 or if patient 14 is voluntarily voiding and the second stimulation therapy may hinder the voluntary voiding attempt. Processor 50 may control therapy module 52 to revert back to delivering the first stimulation therapy if the patient manually aborts the delivery of the second stimulation therapy.

Upon receiving the notification of the prospective delivery of the second stimulation therapy, patient 14 may also provide active input that indicates IMD 16 can deliver the second stimulation therapy or patient 14 may merely not intervene to indicate IMD 16 should deliver the second stimulation therapy. Upon receiving the input confirming the second stimulation therapy or lack of input aborting the second stimulation therapy, processor 50 may load one of first stimulation therapy programs 66 to therapy module 52.

In an example in which telemetry module 58 receives patient input indicating a voluntary voiding event, processor 50 may suspend delivery of the second stimulation therapy for a pre-determined period of time, e.g., 2 minutes. In response to receiving the input, processor 50 may ignore signals indicative of the patient parameter, such as impedance signals received from impedance module 54. Processor 50 may ignore these signals for a predetermined period of time, such as approximately two minutes. After two minutes has elapse, processor 50 may continue monitoring patient 14 to detect trigger events.

The processors described in this disclosure, such as processor 50 and processing circuitry in impedance module 54 and other modules, may be one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. In some examples, the processing circuitry of impedance module 54 that determines an impedance based on a measured voltage and/or current of a signal may be the same microprocessor, ASIC, DSP, or other digital logic circuitry that forms at least part of processor 50.

Memory 56 may also store instructions for execution by processor 50, in addition to first and second stimulation therapy programs 66, 68, and bladder data 69. Information related to measured impedance and determined posture may be recorded for long-term storage and retrieval by a user, or used by processor 50 for adjustment of stimulation parameters, such as amplitude, pulse width, and pulse rate. Memory

56 may include separate memories for storing instructions, electrical signal information, stimulation programs, and bladder data.

Memory 56 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. Memory 56 may store program instructions that, when executed by processor 50, cause IMD 16 to perform the functions ascribed to IMD 16 herein.

Power source 60 delivers operating power to the components of IMD 16. Power source 60 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever stimulation therapy is to occur.

Figure 4:
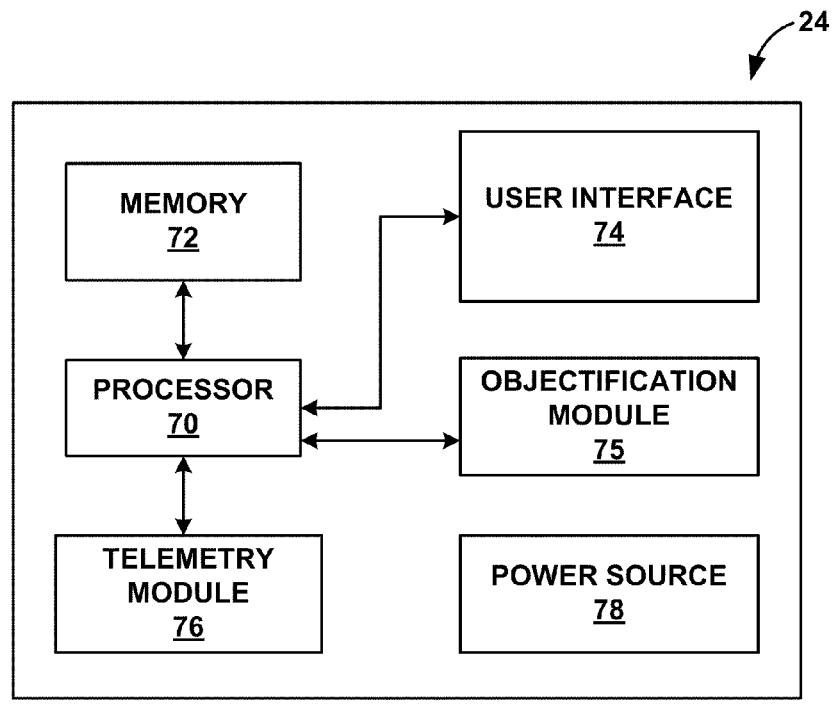
FIG. 4 is a block diagram illustrating an example configuration of the external programmer of the systems shown in FIGS. 1 and 2.

FIG. 4 is a block diagram illustrating example components of external programmer 24. While programmer 24 may generally be described as a hand-held computing device, the programmer may be a notebook computer, a cell phone, or a workstation, for example. As illustrated in FIG. 4, external programmer 24 may include a processor 70, memory 72, user interface 74, objectification module 75, telemetry module 76, and power source 78. Memory 72 may store program instructions that, when executed by processor 70, cause processor 70 and external programmer 24 to provide the functionality ascribed to external programmer 24 throughout this disclosure.

In some examples, memory 72 may further include program information, i.e., therapy programs defining the first type of stimulation therapy and therapy programs defining the second type of stimulation therapy similar to those stored in memory 56 of IMD 16. In other examples, memory 72 may also store two or more therapy programs to be evaluated by patient 14 for efficacy. The stimulation programs stored in memory 72 may be downloaded into memory 56 of IMD 16. Memory 72 may include any volatile, non-volatile, fixed, removable, magnetic, optical, or electrical media, such as RAM, ROM, CD-ROM, hard disk, removable magnetic disk, memory cards or sticks, NVRAM, EEPROM, flash memory, and the like. Processor 70 can take the form one or more microprocessors, DSPs, ASICs, FPGAs, programmable logic circuitry, or the like, and the functions attributed to processor 70 herein may be embodied as hardware, firmware, software or any combination thereof.

User interface 74 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processor 70 may present and receive information relating to stimulation therapy via user interface 74. For example, processor 70 may receive patient input via user interface 74. The input may be, for example, in the form of pressing a button on a keypad or selecting an icon from a touch screen.

Processor 70 may also present information to the patient in the form of alerts related to delivery of the second stimulation therapy to patient 14 or a caregiver, as will be described in more detail below, via user interface 74. Although not shown, external programmer 24 may additionally or alternatively include a data or network interface to another computing device, to facilitate communication with the other device, and presentation of information relating to first and second stimulation therapies via the other device.

Telemetry module 78 supports wireless communication between IMD 16 and external programmer 24 under the control of processor 70. Telemetry module 78 may also be configured to communicate with another computing device via wireless communication techniques, or direct communication through a wired connection. Telemetry module 78 may be substantially similar to telemetry module 58 described above, providing wireless communication via an RF or proximal inductive medium. In some examples, telemetry module 78 may include an antenna, which may take on a variety of forms, such as an internal or external antenna. An external antenna that is coupled to programmer 24 may correspond to a programming head that may be placed over IMD 16.

Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

IMD 16 and/or programmer 24 may control of the timing of the delivery of the first and second stimulation therapies that generate different physiological responses to manage urinary or fecal incontinence. If external programmer 24 controls the stimulation, programmer 24 may transmit therapy programs for implementation by IMD 16 to IMD 16 via telemetry module 78. A user (e.g., patient 14 or a clinician) may select the first and second stimulation therapy programs from a list provided via a display of user interface 74. Alternatively, external programmer 24 may transmit a signal to IMD 16 indicating that IMD 16 should execute locally stored programs or therapy routines. In such a manner, control over the electrical stimulation may be distributed between IMD 16 and external programmer 24, or may reside in either one alone.

In one example, patient 14 may control the stimulation therapy delivered by IMD 16 via external programmer 24. For example, patient 14 may initiate or terminate delivery of either the first or second stimulation therapies by IMD 16 via external programmer 24. For example, patient 14 may selectively control the delivery of the second stimulation therapy by IMD 16 through input entered via user interface 74. That is, IMD 16 may deliver second stimulation therapy based on patient input entered via user interface 74. In this way, patient 14 may use programmer 24 to deliver the second stimulation therapy "on demand," such as when patient 14 senses the onset of a leakage episode.

In another example, programmer 24 may present a notification indicative of the prospective delivery of the second stimulation therapy to patient 14 via user interface 74. As an example, prior to delivering the second stimulation therapy, processor 70 of programmer 24 may generate and present a notification that indicates the second stimulation therapy will be delivered within an indicated period of time. IMD 16 may provide an indication to programmer 24 via the respective telemetry modules 58, 76 that IMD 16 intends on delivering the second stimulation therapy. Programmer 24 may alert patient 14 by presenting a warning message on a display of user interface 74, emitting an audible alert, or generating a somatosensory alert (e.g., a vibrating housing). In such an example, programmer 24 may prompt patient 14 for input via a display of user interface 74. Patient 14 may enter input via user interface 74 that either confirms delivery of the second stimulation therapy or input for manually aborting the second stimulation therapy. In either case, the patient input is transmitted to IMD 16 via telemetry module 78.

As previously indicated, programmer 24 may provide a notification to patient 14 when the second stimulation therapy is triggered too frequently, which may indicate that bladder 12 (FIG. 1) is full. Processor 70 may implement any suitable criteria to generate the alert. Processor 70 may monitor the frequency of the delivery of the second stimulation therapy by IMD 16, e.g., by receiving input from IMD 16 indicating the times at which the second stimulation therapy is delivered to patient 14 or based on patient input received via user interface 74, where the patient input controls the delivery of the second stimulation therapy. For example, in the event that the second stimulation therapy is triggered five times within five minutes, processor 50 may generate a notification to patient 14 indicating the same. This may allow patient 14 to proceed to a bathroom before a leaking episode occurs. The notification provided by programmer 24 may also direct patient 14 to locate a restroom and voluntarily void.

Patient 14 may indicate an intent to void via user interface 74, and processor 70 may implement a blanking interval through communication of the indication to IMD 16 via telemetry module 78. For example, processor 70 may transmit a command signal to IMD 16 that indicates IMD 16 should temporarily suspend delivery of the second stimulation therapy. In some cases, this may permit voluntary voiding by patient 14. In some examples, the length of time for a voiding event may be determined by pressing and holding down a button of user interface 74 for the duration of a voiding event, pressing a button a first time to initiate voiding and a second time when voiding is complete, or based on a predetermined period of time following the indication of voluntary voiding provided by patient 14. In each case, programmer 24 causes IMD 16 to temporarily suspend the second stimulation therapy, and, in some cases, the first stimulation therapy, so that voluntary voiding is possible.

In other examples, IMD 16 may automatically determine when patient 14 is attempting to voluntary void, e.g., based on a voiding signature of an EMG signal indicative of bladder activity or based on bladder pressure or contraction. In such examples, IMD 16 may automatically suspend the delivery of either or both the first and second stimulation therapies to permit patient 14 to voluntary void. In some cases, suspension of stimulation by IMD 16 is not necessary to facilitate voiding, and stimulation may occur substantially simultaneously with the voluntary voiding. For example, the bladder volume will eventually increase to a level to trigger strong bladder contractions that prevails over the second stimulation therapy to allow voiding.

Objectification module 75 may generate objective incontinence information based upon trigger events that activate the delivery of the second stimulation therapy, e.g., patient conditions sensed by a sensor or a patient input activating a therapy "boost" to help prevent an occurrence of an incontinence event. Objectification module 75 may include one or more processors that process data, a portion of processor 70, an analog circuit, or even a software module used by processor 70 to generate objective incontinence information. Although objectification module 75 may store trigger events in some examples, in other examples, objectification module 75 may instead retrieve trigger events and other data from memory 72 when needed to generate objective incontinence information.

In the example shown in FIG. 4, under the control of processor 70, objectification module 75 retrieves trigger event data from memory 72 of programmer 24 or a memory of another device (e.g., IMD 16 or a remote database) and generates objective incontinence information based on the trigger event data. The trigger event data may include, for example, a value, flag, signal or the like that stored to indicate the occurrence of a trigger event, and, in some examples, the time the trigger event data was generated. As previously discussed, a sensor may automatically generate the trigger event based upon a sensed condition or the trigger event may be an input provided by a patient as a request for the second stimulation therapy. This trigger event may be a prolonged request for the second stimulation therapy in other examples, e.g., the user holds down an input for as long as necessary to avoid releasing urine. In this example, the trigger even itself may have a duration. In some examples, the patient input indicates an imminent involuntary voiding event (e.g., a patient state in which an involuntary voiding event is likely) or an occurrence of a situation in which a possibility of an involuntary voiding event will occur has increased (e.g., because of the activity or posture undertaken by the patient).

In some examples, the objective incontinence information may include information or data that is indicative of the patient's condition or efficacy of stimulation therapy. As one example, the objective incontinence information include trend, frequency, or number of trigger events or clusters of trigger events over time (e.g., per day, per week, per month, per year or for any other suitable time range). Each cluster may be associated with a voluntary voiding event. For example, shortly after a cluster of trigger events, there may be an emptying of bladder 12 (e.g., after a voluntary voiding event), followed by an absence of trigger events until bladder 12 is full or nearly full or patient 14 perceives bladder 12 to be full or nearly full. Thus, each cluster of trigger event may be associated with a respective voluntary voiding event. Tracking voluntary voiding events may be useful for evaluating the patient bladder health, as well as confirm that the voiding habits of patient 14 are not contributing to the incontinence. A trend in trigger events may also indicate a progression or other change of the patient condition. For example, an increase in frequency of trigger events over time may indicate that patient 14 perceives more frequency of urges, which in turn may indicate detrusor overactivity. The opposite may be suggested by a decrease in frequency of trigger events over time.

Another type of objective incontinence information may include the time durations between clusters of trigger events, which may indicate the frequency of sense of urgency or detrusor overactivity perceived by patient 14, which can be useful for monitoring the progression of the patient condition or otherwise monitoring or evaluating patient 14. The duration of time between a voluntary voiding event (e.g., determined based on patient 14 input and/or based on sensor input) and a first subsequent trigger event or cluster of trigger events can indicate bladder capacity of patient 14. The time durations between clusters of trigger events may be useful for monitoring parameters of bladder filling (e.g., voiding frequency, bladder capacity, and the like), which can be useful for monitoring changes in a patient condition. As noted above, trigger events may be generated when bladder 12 of patient 14 is full or nearly full or when patient 14 perceives bladder 12 to be full or nearly full. Thus, shortly after emptying bladder 12 (e.g., after a voluntary voiding event), there may be an absence of trigger events until bladder is full or nearly full or patient 14 perceives bladder 12 to be full or nearly full. The time duration between a voluntary voiding event and the first subsequent cluster may be useful for monitoring parameters of bladder filling (e.g., voiding frequency, bladder capacity, and the like), which may be useful for monitoring changes in a patient condition. The emptying of the bladder may be indicated by the patient through an external patient programmer and/or recorder or a tap on IMD 16 through a motion sensor (e.g., an accelerometer or a piezoelectric crystal). As a result, the time interval between a voluntary voiding event and a first subsequent cluster of trigger event may be indicative of the bladder capacity cycle of patient 14.

Another type of objective incontinence information may include time durations between individual trigger events in a cluster, which may indicate the severity of a particular urge event that is associated with the cluster. In some examples, such as examples in which patient 14 provides input to activate the second stimulation therapy, the trigger event may indicate an imminent involuntary voiding event as perceived by patient 14 or a situation in which a possibility of an involuntary voiding event will occur has increased (e.g., because of the activity or posture undertaken by patient 14). The number of trigger events associated with a common cluster can indicate, for example, the severity of the imminent involuntary voiding event, and, if patient 14 was experiencing urgency (e.g., a sudden and unstoppable need to urinate), the severity of the urgency event.

Objective incontinence information may also include a ranking of clusters of trigger events based upon a frequency of trigger events within each cluster. This ranking may indicate, for example, which clusters were more severe than others; severity may increase with the number of trigger events associated with a particular cluster. Another type of objective incontinence information includes a number or frequency of trigger events or clusters of trigger events associated with a therapy program, which can be useful for evaluating the therapy programs. For example, if the therapy programs were used by IMD 16 to generate and deliver the first stimulation therapy, the number or frequency of trigger events or clusters of trigger events associated with the therapy programs may indicate the efficacy of the therapy programs. In some cases, a greater number of trigger events or clusters of trigger events or the higher the frequency of trigger events or clusters of trigger events associated with a therapy program may indicate the therapy program is less efficacious than other therapy programs associated with a fewer number of trigger events or clusters of trigger events or a lower the frequency of trigger events or clusters of trigger events.

Another type of objective incontinence information may include a number or frequency of trigger events or clusters of trigger events associated with time of day (e.g., day or night). As discussed in greater detail below, this may be useful for diagnosing a patient condition (e.g., nocturia) and/or for selecting a therapy program for the first stimulation therapy delivered at different times of day. Objective incontinence information may also include a number or frequency trigger events or clusters of trigger events associated with at least one type of patient activity or posture state. As discussed in greater detail below, this type of objective incontinence information may be useful for distinguishing whether a particular urgency event or perceived imminent involuntary voiding event was attributable to stress or urge incontinence. In addition, objective incontinence information that associates a number or frequency trigger events or clusters of trigger events with a patient activity or posture state may be useful for formulating a therapy regimen for patient 14. If, for example, the objective incontinence information indicates that a greater number of clusters of trigger events are associated with a particular posture state, a clinician or a device may automatically adjust the first stimulation therapy to provide more efficacious therapy to patient 14 when that posture state is detected.

Objective incontinence information may also include a number or frequency of trigger events or clusters of trigger events associated with at least one physiological parameter of patient 14. The physiological parameter of patient 14 may indicate the actual physiological condition of patient 14 when the patient activated the second stimulation therapy or when the trigger event was detected by a sensor. In some examples, this may help a clinician identify which patient-perceived events are substantiated by the physiological data. As an example, if the patient provides an input request a boost of therapy, thereby resulting in a trigger event, the clinician may use programmer 24 or another device to view the one or more physiological parameters sensed when the trigger event occurred. If the physiological parameter indicates bladder 12 was not contracting (e.g., based on EMG data) and/or bladder 12 was not full (e.g., based on bladder impedance), the clinician may determine that the patient's perception of an imminent involuntary voiding event or urgency event is more severe than the actual event that occurred. As another example, if the physiological parameter indicates bladder 12 was contracting and/or bladder 12 was full at the time patient 14 provided input requesting a boost of therapy, the clinician may determine that patient 14 did in fact perceive a true incontinence event.

The objective incontinence information generated based on the trigger event data can include one or more of the types described above. Although not specifically specified, other combinations of trigger events over time, or in association with other data, are contemplated. As stated above, a trigger event may be an occurrence of a patient input requesting the delivery of the second stimulation therapy or generated based on a sensed physiological parameter of patient 14.

In general, objectification module 75 may recognize multiple trigger events as a cluster when the trigger events all occur within a predetermined amount of time. For example, the predetermined amount of time, or cluster window, may be set to 5 minutes. However, the cluster window may generally be set to any time duration between approximately 1 minute and 60 minutes. Alternatively, objectification module 75 may recognize multiple trigger events as a cluster when the trigger events occur within a predetermined interval of each other. For example, the predetermined interval may be set to 2 minutes, although other intervals may also be used. Therefore, the string of all trigger events with less than 2 minutes between each trigger event would be grouped as a single cluster of trigger events. Although this cluster interval may generally be set to any time between approximately 10 seconds and 30 minutes, the cluster interval may be set to any duration of time. In still other examples, objectification module 75 may subjectively group trigger events into clusters based upon their occurrence in time. In any case, a cluster may be used to indicate a single imminent voiding event or actual voiding event. Because patient 14 may provide an input requesting the second stimulation therapy multiple times before voiding occurs, a single cluster of those trigger events may be sufficient to indicate to a user when voiding likely occurred. In addition, determining the number and frequency of trigger events within each cluster may indicate the number and frequency of bladder contractions.

As discussed above, the data indicative of the occurrence of trigger events with which objectification module 75 generates objective incontinence information may be received from a variety of sources. For example, the trigger event data may be received from a sensor that indicates a bladder condition, e.g., electrodes 19 and 21 of FIG. 1, a pressure sensor, or ultrasound sensor. In addition or in other examples, the trigger event data may be received from an activity sensor that indicates a patient activity level or posture of patient 14, e.g., an accelerometer that detects an activity or posture of patient 14. Either of these sensors may be examples of sensor 22 described in FIG. 3. Additionally or alternatively, the trigger event data may be generated by processor 70 based on input received from a patient in the form of a patient input via user interface 74. A trigger event from the patient input may be an objective indication of when patient 14 perceives an imminent or actual voiding event. In this case, for example, the trigger event data generated based on patient input may be used to generate a voiding diary that tracks the occurrence of imminent or actual voiding diaries in addition to or instead of a patient diary or log of voiding events manually maintained by patient 14.

Objectification module 75 may also store instructions regarding the presentation form of the objective incontinence information. These instructions may specify parameters for presenting any data included in the objective incontinence information, including bar graphs, charts, scatter plots, lists, ranked lists, or even user preferences changed though using programmer 24. Processor 70 may then use these instructions to present the objective incontinence information to the user via user interface 74.

In addition to presenting objective data to the user via user interface 74, objectification module 75 may also guide the user through selection of therapy programs based on the objective incontinence information. For example, objectification module 75 may associate each trigger event with the therapy program used to define the first incontinence stimulation therapy when the trigger event is received. In this manner, the user may relatively easily identify which therapy program was used to provide therapy when patient 14 needed to request the second incontinence stimulation therapy. In some cases, therapy programs associated with a lower number of trigger events may generally be more effective at treating patient 14. In this way, the objective incontinence information generated based on trigger event data may be useful for evaluating a plurality of therapy programs and comparing the efficacy of therapy programs to each other.

Further, in some examples, objectification module 75 is configured to provide suggested therapy programs to the user based upon the objective incontinence information. As patient 14 evaluates multiple therapy programs provided by the clinician, e.g., during a trial stimulation session, trigger events and other collected data may be associated with the evaluated programs. Therefore, objectification module 75 or processor 70 may use the objective incontinence information to present a plurality of evaluated incontinence therapy programs to the user. With the aid of objectification module 75 (or processor 70), the presented therapy programs may be sorted, ordered, or ranked based on the objective incontinence information. For example, the plurality of evaluated therapy programs may be sorted, ordered or ranked according to the most efficacious therapy program as indicated by minimal associations with trigger events (e.g., individual trigger events or trigger event clusters). Because trigger events, particularly from patient input, may suggest that the first stimulation therapy is not adequate to treat patient 14, therapy programs that defined the first stimulation therapy and associated with fewer trigger events may be more efficacious for patient 14. After suggested therapy programs are presented to the user, user interface 74 may receive a therapy program selection from the user that selects an effective therapy program from the plurality of evaluated of therapy programs. The effective therapy program may then be used to define and deliver subsequent incontinence stimulation therapy.

In some examples, processor 70 may automatically select an incontinence therapy program from the plurality of evaluated incontinence therapy programs associated with trigger events or other objective incontinence information. For example, processor 70 may select the therapy program for the first stimulation therapy that is associated with the fewest number of trigger events (e.g., individual trigger events or trigger event clusters). As indicated above, the therapy program associated with the fewest number of trigger events may be the most efficacious for patient 14 relative to the other evaluated therapy programs. Processor 70 may then use the automatically selected effective therapy program to control IMD 16 define and deliver subsequent first stimulation therapy. In some examples, user interface 74 may notify the user of the automatically selected therapy program, and the user may select a different therapy program if desired. Automatically selecting a therapy program based upon the objective incontinence information may help refine stimulation therapy in an efficient manner and based on information specific to patient 14, while also reducing the amount of direct clinician input needed throughout the therapy for patient 14.

Although objectification module 75 has been described within programmer 24, other examples of system 10 may provide the function of objectification module 75 in other devices. For example, objectification module 75 may reside within IMD 16 to facilitate the distribution of objective incontinence information between multiple external programmers, e.g., a patient programmer and a clinician programmer. In other examples, objectification module 75 may be located in a different external computing device for analysis by a workstation, notebook computer, external server, cloud computing network, or other system. For complex analysis of the objective incontinence information, these alternative computing solutions may be beneficial to finding the most appropriate therapy for patient 14. Moreover, some or all functions described as being performed by objectification module 75 may also be performed by processor 70 or another processor of therapy system 10.

Power source 78 delivers operating power to the components of programmer 24. Power source 78 may include a battery and a power generation circuit to produce the operating power. In some examples, the battery may be rechargeable to allow extended operation. Recharging may be accomplished by electrically coupling power source 78 to a cradle or plug that is connected to an alternating current (AC) outlet. In addition or alternatively, recharging may be accomplished through proximal inductive interaction between an external charger and an inductive charging coil within programmer 24. In other examples, traditional batteries (e.g., nickel cadmium or lithium ion batteries) may be used. In addition, programmer 24 may be directly coupled to an alternating current outlet to power programmer 24. Power source 78 may include circuitry to monitor power remaining within a battery. In this manner, user interface 74 may provide a current battery level indicator or low battery level indicator when the battery needs to be replaced or recharged. In some cases, power source 78 may be capable of estimating the remaining time of operation using the current battery.

FIGS. 5-10 are flow diagrams illustrating example techniques to reduce the likelihood of incontinence events with a therapy system that generates and delivers first stimulation therapy that generates a first physiological response by patient 14 and a second stimulation therapy that generates a second physiological response. The first stimulation therapy may be delivered in as part of open loop therapy that does not use feedback from a sensor to trigger therapy delivery, while the second stimulation therapy is delivered as part of closed loop therapy that utilizes patient input or feedback from a sensor to trigger therapy delivery. The flow diagrams shown in FIGS. 5-10 include some of the same steps, which are like-numbered for ease of description. The example technique shown in FIGS. 6-10 may be viewed as specific examples of the technique shown in FIG. 5.

Figure 5:
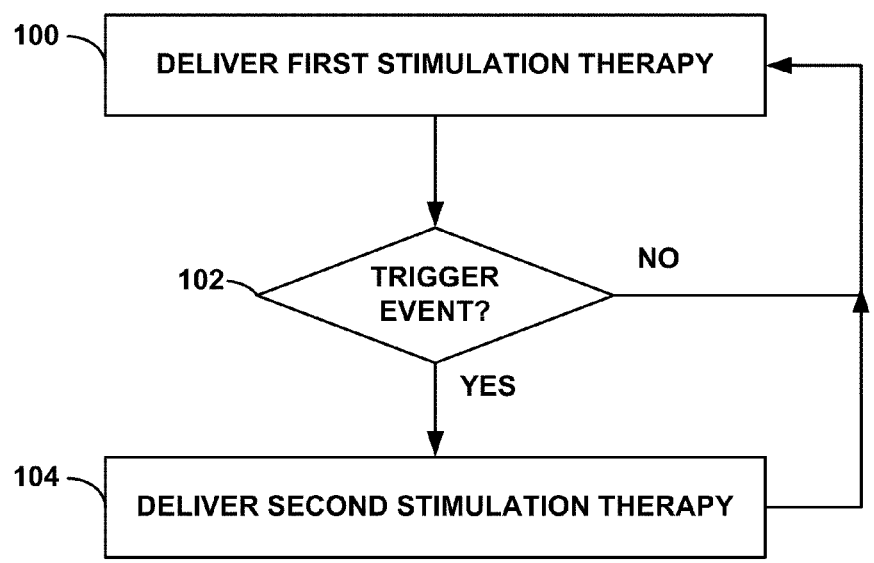
FIGS. 5-10 are flow diagrams illustrating example techniques of delivering first stimulation therapy and, when triggered, a second stimulation therapy to a patient to manage urinary incontinence.

FIG. 5 is a flow diagram illustrating an example technique for delivering first and second stimulation therapies to a patient to manage fecal or urinary incontinence. IMD 16 delivers first stimulation therapy to patient 14 (100). In some examples, IMD 16 initiates the delivery of the first stimulation therapy upon activation of chronic therapy delivery by the clinician. IMD 16 delivers the first stimulation therapy chronically, e.g., periodically for an extended period of time, such as hours, days, weeks, or, in examples in which the first and second stimulation therapies are not delivered simultaneously, until an event occurs that triggers delivery of the second stimulation therapy.

IMD 16 monitors a patient condition via a sensor to determine whether a trigger event is detected (102). Example trigger events may be detected include, but are not limited to, bladder contraction exceeding (e.g., greater than or equal to) a threshold level, abnormal detrusor muscle activities (e.g., as indicated by an EMG) patient activity level exceeding a threshold level, patient posture state, and patient input. As previously described, IMD 16 may monitor bladder impedance, bladder pressure, pudendal or sacral afferent nerve signals, a urinary sphincter EMG, or any combination thereof to detect changes in bladder contraction.

The steps of delivering the first stimulation therapy and monitoring the patient to detect a trigger event are illustrated in FIG. 5 as being sequential, but it should be understood that these steps may be performed simultaneously instead of sequentially. As an example, IMD 16 may deliver the first stimulation therapy to patient 14 for an extended period of time. During the extended period of time, IMD 16 may periodically monitor patient 14 to detect a trigger event. In some examples, IMD 16 may monitor patient 14 following delivery of a train of first stimulation therapy, e.g., in examples in which the first stimulation therapy is defined by a plurality of consecutive trains of stimulation separated by intervals of time. In other examples, IMD 16 may monitor patient 14 more frequently or less frequently. In yet other examples, IMD 16 may monitor patient 14 substantially continuously.

If IMD 16 does not detect a trigger event ("NO" branch of block 102), IMD 16 continues to deliver the first stimulation therapy (100). On the other hand, if IMD 16 detects a trigger event ("YES" branch of block 102), IMD 16 delivers the second stimulation therapy (104). The first and second stimulation therapies may be delivered substantially simultaneously or in an alternating manner (e.g., one type of stimulation is delivered at a time).

In some examples, IMD 16 delivers the second stimulation therapy for a predetermined period of time, e.g., about 10 seconds to about 50 seconds. The duration of the predetermined period of time may be selected such that an imminent involuntary voiding event is suppressed. As described in further detail below with reference to FIG. 9, in some examples, after the predetermined period of time, IMD 16 determines whether the patient condition that triggered the delivery of the second stimulation therapy is still present. For example, IMD 16 may determine whether the bladder contractions are still greater than or equal to a threshold value. If the patient condition that triggered the delivery of the second stimulation therapy is still present, IMD 16 may deliver the second stimulation therapy again for another predetermined period of time.

In other examples, IMD 16 delivers the second stimulation therapy for a period of time controlled by patient 14. For example, patient 14 may control the duration of the second stimulation therapy by interacting with programmer 24, e.g., by pressing a "boost" button on a keypad or a touch screen, or by interacting directly with IMD 16 (e.g., by tapping skin superior to the implanted IMD 16). A maximum therapy period for patient controlled stimulation may be approximately 3 minutes, although other time ranges are contemplated.

After completion of the delivery of the second stimulation therapy, IMD 16 reverts back to delivering the first stimulation therapy (100) and the technique shown in FIG. 5 are repeated as necessary. Thus, IMD 16 delivers the first stimulation therapy and, when triggered, delivers the second stimulation therapy for a limited duration of time (e.g., shorter in duration than the duration of time that the first stimulation therapy is delivered). That is, IMD 16 delivers chronic stimulation for an extended period of time via the first stimulation therapy, and, when necessary or desirable, delivers an additional boost of stimulation via the second stimulation therapy. The boost of stimulation is provided for a comparatively short period of time within the extended period of time during which the chronic therapy delivery is provided.

In this way, IMD 16 provides responsive stimulation to control urinary incontinence. Delivering the second stimulation therapy upon detection of a trigger event, rather than on a substantially regular basis, may help reduce muscle fatigue by limiting the amount of the second stimulation therapy provided to patient 14. In addition, implementing the second stimulation therapy only when needed may help conserve power of power source 60 of IMD 16. Conserving power may help elongate the useful life of IMD 16.

Figure 6:
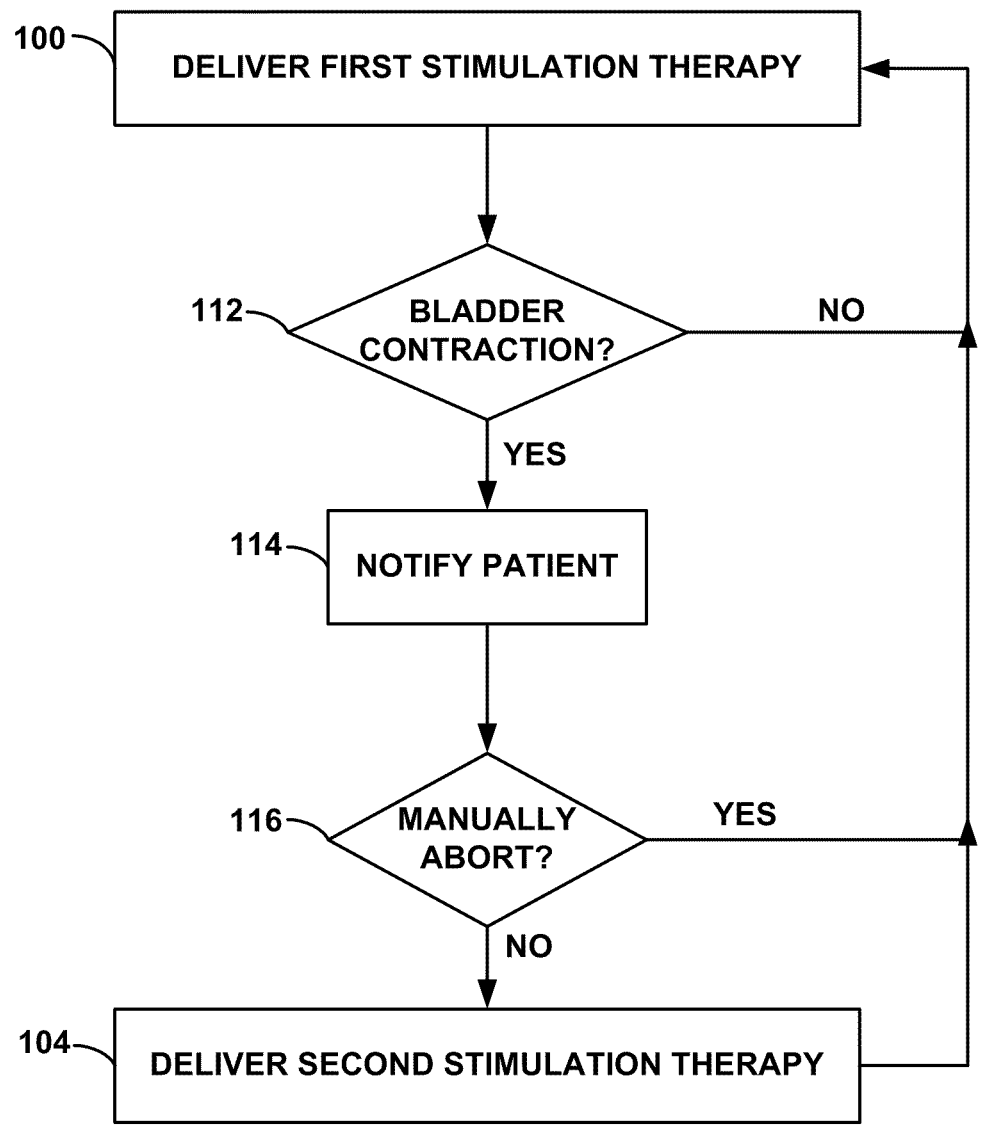

FIG. 6 is a flow diagram illustrating an example technique for delivering a first stimulation therapy to manage incontinence of patient 14 and, when triggered by sensed bladder contraction, delivering a second stimulation therapy to patient 14 to provide an additional mechanism resulting in a different physiological effect that further helps prevent an involuntary voiding event. The technique shown in FIG. 6 allows patient 14 to manually abort the delivery of the second stimulation therapy. In the description of FIG. 6, bladder contractions are referred to as the trigger event for activating the delivery of the second stimulation therapy. In other examples, the trigger event may be any suitable trigger event, such as the detection of patient input, a particular patient posture state, a patient activity level greater than threshold value, or detrusor muscle activities greater than or equal to a threshold value or substantially matching a template.

As with the technique shown in FIG. 5, processor 50 of IMD 16 controls therapy delivery module 52 to generate and deliver the first stimulation therapy to patient 14 (100). Processor 50 monitors a physiological parameter of patient 14 to detect bladder contraction (112). For example, processor 50 may monitor bladder impedance with the aid of signals generated by impedance module 54, or bladder pressure, pudendal or sacral afferent nerve signals, a urinary sphincter EMG, or any combination thereof with the aid of signals generated by sensor 22.

If processor 50 of IMD 16 does not detect bladder contractions that are greater than or equal to a threshold level ("NO" branch of block 112), IMD 16 continues to deliver the first stimulation therapy (100). On the other hand, if processor 50 determines that sensed bladder contractions are indicative of an imminent voiding event or at least an increased probability of an occurrence of an involuntary voiding event (e.g., as indicated by a bladder contraction greater than or equal to a threshold level) ("YES" branch of block 112), processor 50 generates a notification for patient 14 (114). The notification may indicate that bladder contraction indicative of an imminent involuntary voiding event has been detected. IMD 16 may alert patient 14 by, for example, wirelessly communicating with programmer 24 to cause programmer 24 to provide an alert. Programmer 24 may alert the patient by displaying a warning message within a display or emitting an alert sound. In other examples, IMD 16 may generate the patient notification by generating a somatosensory alert (e.g., by generating a notification that is felt by patient 14). For example, IMD 16 may cause an outer housing of IMD 16 to vibrate.

After notifying patient 14 (114), IMD 16 determines whether patient 14 has indicated that the second stimulation therapy should be aborted (116) prior to actually delivering the second stimulation therapy stimulation. In some examples, IMD 16 may determine if patient 14 wants to manually abort the delivery of the second stimulation therapy based on patient input. The patient input may be input entered via programmer 24. As an example, patient 14 may press a button on a keypad or select an icon using a touch screen to enter input. Programmer 24 wirelessly transmits the patient input to IMD 16. As another example, patient 14 may provide input by tapping the skin proximate IMD 16 in a predetermined pattern, such that IMD 16 detects the movement (e.g., via a signal generated by a motion sensor) and characterizes the movement as patient input.

When the patient input indicates that patient 14 wants to stop the delivery of the second stimulation therapy ("YES" branch of block 116), IMD 16 continues to deliver the first stimulation therapy (100). Patient 14 may want to abort the delivery of the second stimulation therapy, for example, during a voluntary voiding event. Permitting patient 14 to manually abort the delivery of second stimulation therapy may also allow patient 14 to prevent unwanted stimulation in the event that IMD 16 incorrectly detected the bladder contraction.

If processor 50 of IMD 16 determines that patient 14 does not want to manually abort the delivery of the second stimulation therapy ("NO" branch of block 116), IMD 16 delivers the second stimulation therapy for a therapy period, which may be predetermined (104). Processor 50 may automatically determine that patient 14 does not want to manually abort the delivery of the second stimulation therapy by receiving input from patient 14 indicating that the second stimulation therapy is desirable. In other examples, processor 50 automatically determines that patient 14 does not want to manually abort the delivery of the second stimulation therapy if patient 14 does not provide any input within a certain period of time following the patient notification. After IMD 16 delivers the second stimulation therapy for a therapy period (104), IMD 16 continues to deliver the first stimulation therapy (100).

Figure 7:
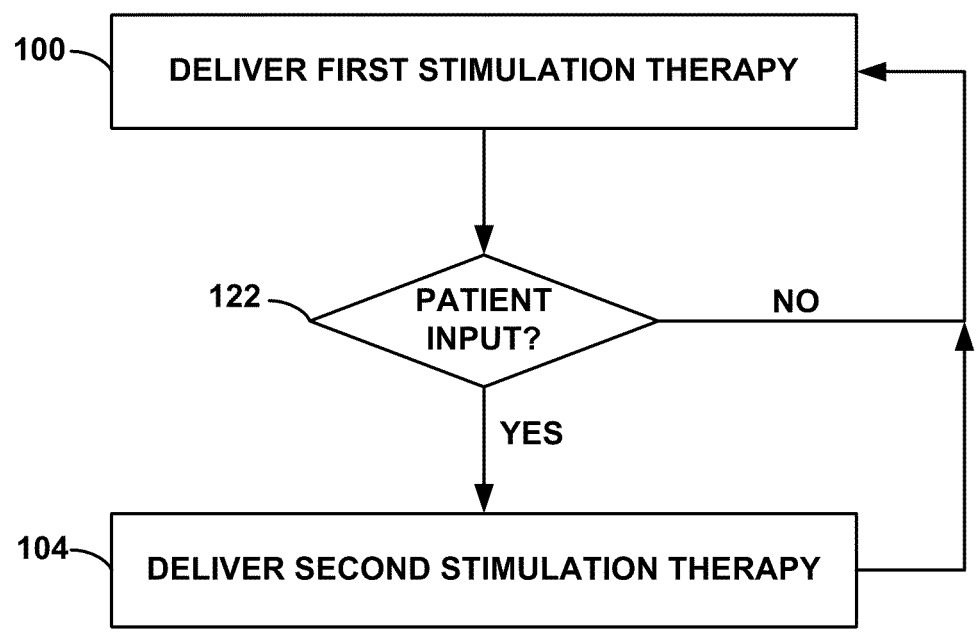

FIG. 7 is a flow diagram illustrating an example technique for delivering a stimulation therapy to patient 14 to manage urinary or fecal incontinence, where the technique includes delivering a first, primary electrical stimulation therapy and, upon receiving patient input, delivering a second stimulation therapy. The example technique shown in FIG. 7 is an example of the technique shown in FIG. 5. That is, the event that triggers the delivery of the second stimulation therapy in FIG. 7 is patient input.

In accordance with the technique shown in FIG. 7, IMD 16 delivers first stimulation therapy to patient 14 (100). Upon receiving patient input (122), processor 50 of IMD 16 controls therapy delivery module 52 to generate and deliver the second stimulation therapy to patient 14 to generate the second physiological response that helps prevent an involuntary voiding event. In some cases, processor 50 of IMD 16 upon receiving patient input to discontinue the delivery of the first stimulation therapy prior to the delivery of the second stimulation therapy, while in other examples the first and second stimulation therapies are delivered substantially simultaneously.

As previously indicated, patient 14 may provide the patient input via programmer 24, e.g., by activating a button on a keypad or select an icon using a touch screen of programmer 24. Programmer 24 wirelessly communicates the patient input to IMD 16. In other examples, patient 14 may provide input indicating the delivery of the second stimulation therapy is desirable via IMD 16. For example, IMD 16 may include a motion sensor that detects movement of IMD 16 and patient 14 may provide input by tapping the skin proximate IMD 16 in a predetermined pattern, such that IMD 16 detects the movement and characterizes the movement as patient input.

If IMD 16 does not receive patient input that activates the delivery of the second stimulation therapy ("NO" branch of block 122), IMD 16 continues to deliver the first stimulation therapy (100) and monitor for patient input.

Figure 8:
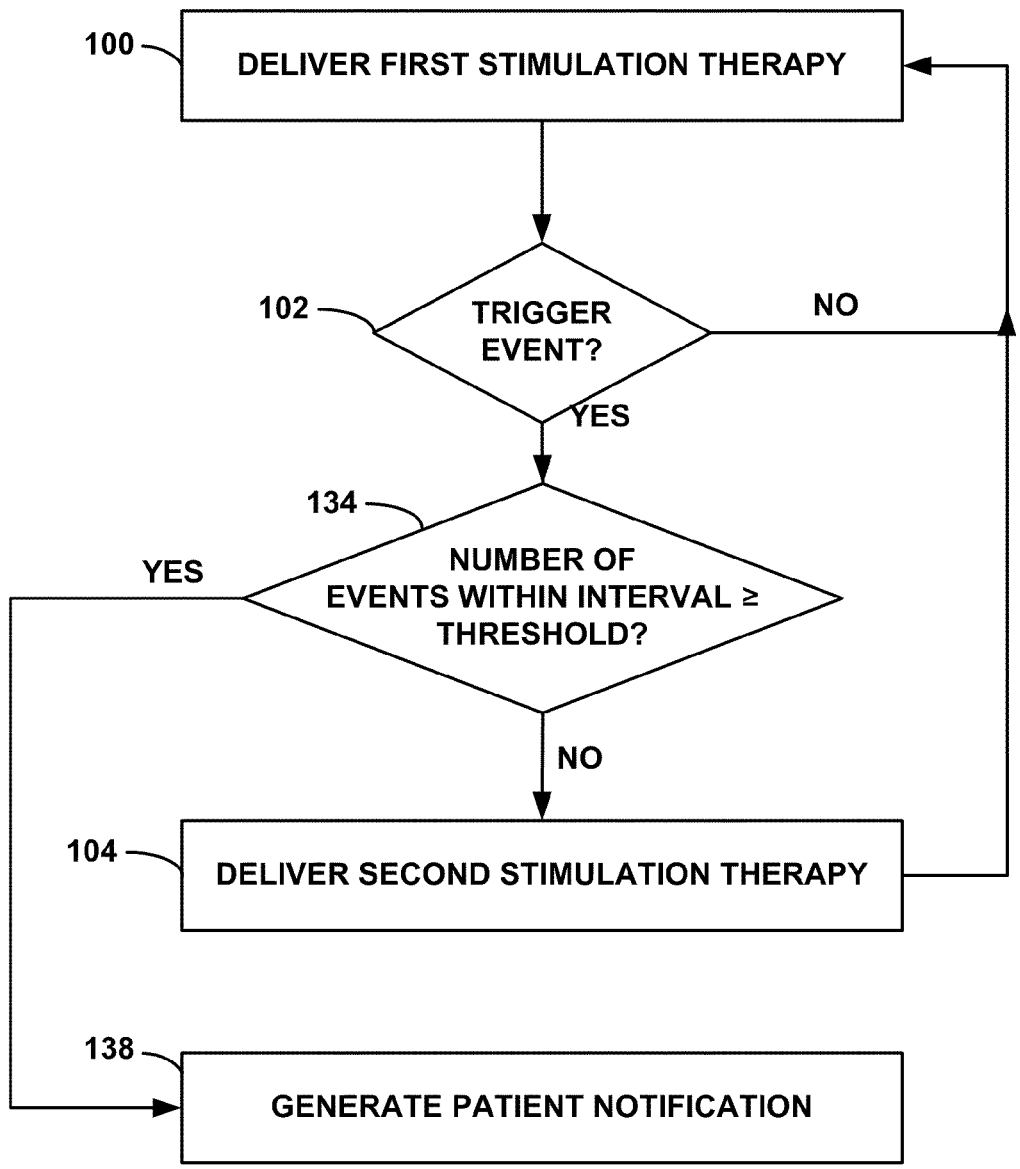

FIG. 8 is a flow diagram illustrating an example technique for controlling the delivery of the second stimulation therapy to patient 14, and notifying patient 14 when the second stimulation therapy is delivered too frequently. As with the techniques shown in FIGS. 5-7, IMD 16 first delivers a first stimulation therapy to patient 14 (100). In accordance with the previously described example methods, IMD 16 monitors a patient parameter (e.g., a physiological parameter, activity level or posture state) and/or patient input to detect a trigger event (102).

If IMD 16 does not detect a trigger event ("NO" branch of block 102), IMD 16 continues to deliver the first stimulation therapy (100). However, if IMD 16 detects a trigger event ("YES" branch of block 102), IMD 16 determines whether too many trigger events occurred within a predetermined interval (134). In the example shown in FIG. 8, processor 50 of IMD 16 compares the number of trigger events detected within the a predetermined interval to a threshold value, which may be stored in memory 56 (FIG. 3) of IMD 16.

If processor 50 determines that too many trigger events occurred within the predetermined interval of time ("YES" branch of block 134), processor 50 generates an alert to notify patient 14 that the trigger events that activate the delivery of the second stimulation therapy are occurring too frequently (138). Trigger events occurring at a frequency higher than a stored frequency may indicate that bladder 12 (FIG. 1) is full. Processor 50 (or processor 70 of programmer 24) may track the number of trigger events within the predetermined range of time using any suitable technique, such as by implementing a counter.

If processor 50 determines that too many trigger events have not occurred within the predetermined interval of time ("NO" branch of block 134), IMD 16 delivers the second stimulation therapy stimulation to patient 14 (104) and repeats the technique shown in FIG. 8 as necessary.

Figure 9:
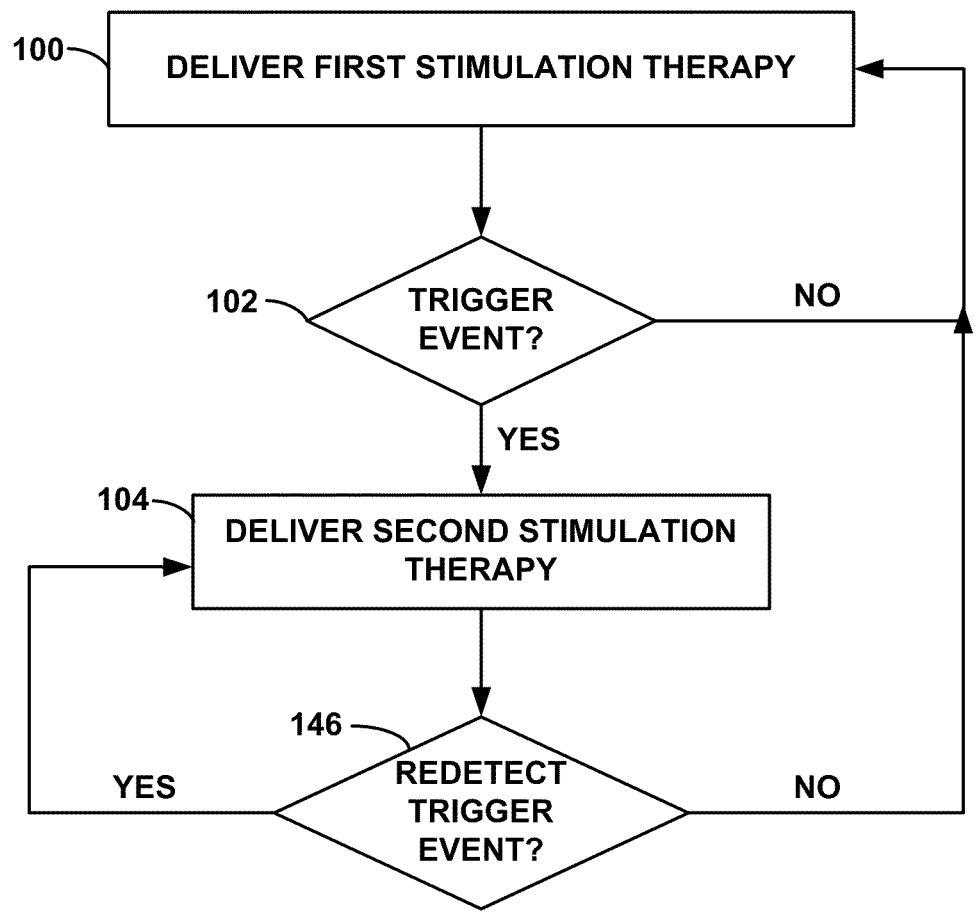

FIG. 9 is a flow diagram illustrating another example technique for delivering first stimulation therapy to manage incontinence and, when triggered by sensor or patient input, delivering a second stimulation therapy to boost the effectiveness of the first stimulation therapy. In the example technique illustrated in FIG. 9, the second stimulation therapy is delivered for another therapy period if a trigger event is still detected after the stimulation therapy was delivered for a therapy period. Each therapy period may include the delivery of stimulation signals for a predetermined duration of time. In the technique shown in FIG. 9, IMD 16 delivers the second stimulation therapy until the trigger event is no longer detected or the therapy interval is over.

IMD 16 first delivers the first stimulation therapy to patient 14 (100) and monitors patient 14 to detect a trigger event (102). If IMD 16 does not detect a trigger event ("NO" branch of block 102), IMD 16 continues deliver the first stimulation therapy (100) until a trigger event is detected. Upon detecting the trigger event ("YES" branch of block 102), IMD 16 delivers the second stimulation therapy stimulation to patient 14 (104). In the example shown in FIG. 9, IMD 16 delivers the second stimulation therapy to patient 14 by delivering a plurality of stimulation signals during a predetermined range of time, which may be referred to as a therapy period.

After delivering the second stimulation therapy for the therapy period, IMD 16 determines whether the trigger event is detected again or is still occurring (146). In an example in which the trigger event is contraction of bladder 12 of patient 14, IMD 16 determines whether the contraction of bladder 12 is greater than or equal to a threshold level. If the bladder contraction subsided during the first therapy period ("NO" branch of block 146), IMD 16 deactivates delivery of the second stimulation therapy and reverts back to delivering the first stimulation therapy (100) and monitoring the patient for another trigger event (102). On the hand, if processor 50 of IMD 16 redetects the trigger event ("YES" branch of block 146), IMD 16 continues to deliver the second stimulation therapy for a second therapy period (104).

After the second therapy period, processor 50 determines whether the trigger event is still present (146), and continues to control therapy delivery module 52 (FIG. 3) deliver the second stimulation therapy until the trigger event is no longer present. In other examples, processor 50 controls therapy delivery module 52 to deliver the second stimulation therapy until the trigger event is no longer present or until a maximum number of therapy periods have been delivered within a certain amount of time. The maximum number of therapy periods within certain amount of time may be stored in memory 56 of IMD 16 or another device, and may be selected by a clinician.

Figure 10:
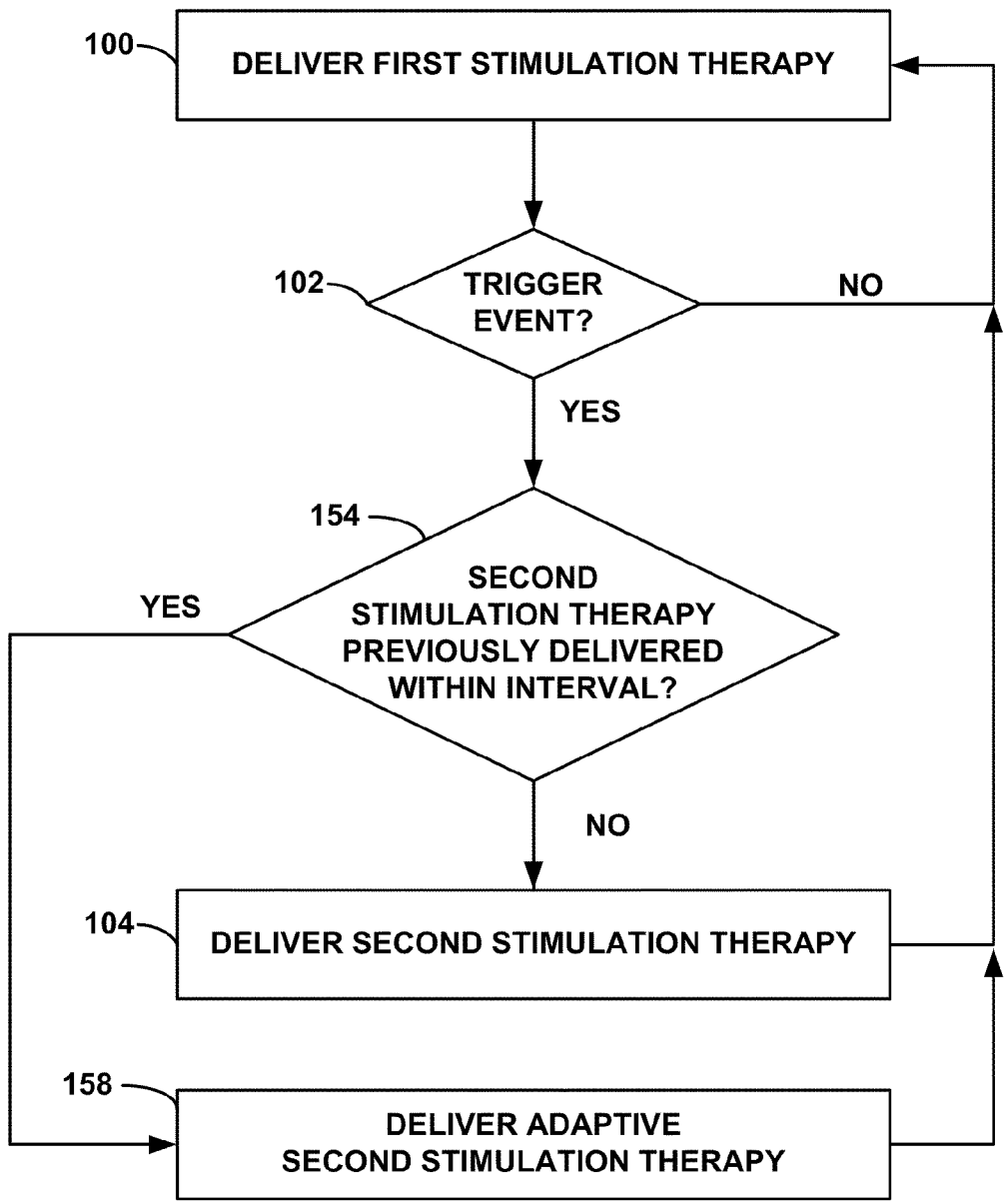

FIG. 10 is a flow diagram illustrating an example technique for delivering first stimulation therapy and, when triggered by sensor input or patient input, delivering adaptive second stimulation therapy to a patient. Adaptive second stimulation therapy includes second stimulation therapy that generates a different physiological response than the first stimulation therapy, whereby the stimulation parameters of the second stimulation therapy changes over time. Adaptive second stimulation therapy may be configured to maximize closure of the urinary or anal sphincter and minimize muscle fatigue.

IMD 16 delivers first stimulation therapy to patient 14 (100) and monitors signals from one or more sensors and/or patient input to detect trigger events (102). If processor 50 of IMD 16 does not detect a trigger event ("NO" branch of block 102), IMD 16 continues to deliver the first stimulation therapy. However, if processor 50 detects a trigger event ("YES" branch of block 102), IMD 16 determines whether the second stimulation therapy, which is a temporary "dose" of stimulation therapy, was previously delivered within a predetermined interval of time (154). The predetermined interval of time may be referred to as an inter-therapy interval and may be, for example, approximately 30 seconds, although other intervals of time are contemplated.

If IMD 16 has not previously delivered the second stimulation therapy within the interval of time ("NO" branch of block 154), IMD 16 delivers the second stimulation therapy to patient 14 without modifying the therapy parameters of the second stimulation therapy (104). On the other hand, if processor 50 of IMD 16 determines that IMD 16 has previously delivered the second stimulation therapy within the interval of time ("YES" branch of block 154), processor 50 controls therapy delivery module 52 (FIG. 3) to generate and deliver adaptive second stimulation therapy to patient 14 (158). Processor 50 adjusts one or more parameters of the second stimulation therapy if IMD 16 has previously delivered the second stimulation therapy within the interval of time, thereby providing "adaptive" second stimulation therapy. Adjusting one or more parameters of the second stimulation therapy help minimize patient adaptation to the second stimulation therapy, as well as any muscle fatigue that may result from the second stimulation therapy.

In general, changing one or more aspects of the second stimulation therapy if IMD 16 has previously delivered the second stimulation therapy within the predetermined interval of time may help prevent the same stimulation signal from being delivered to patient 14 for a relatively long period of time. This helps prevent patient 14 from growing accustomed to the stimulation signal, e.g., adaptation, which may result in a decrease in the effectiveness of the second stimulation therapy over time. In addition, changing one or more aspects of the second stimulation therapy may help reduce muscle fatigue by changing the way in which the muscles of patient 14 are stimulated by the second stimulation therapy.

IMD 16 delivers the adaptive second stimulation therapy (158) by delivering the second stimulation therapy according to different parameters than then previously delivered the second stimulation therapy. As an example, IMD 16 may deliver adaptive second stimulation therapy by delivering second stimulation therapy that stimulates fast-twitch muscles during a first therapy period, and the second stimulation therapy that stimulates slow-twitch muscles during a second therapy period subsequent to the first therapy period, and varying the duration of the first and second intervals over time each time that adaptive second stimulation therapy is delivered within the predetermined interval. Example stimulation signals that illustrate adaptive second stimulation therapy is described with respect to FIGS. 13A-14C.

While the techniques described with reference to FIGS. 6-10 are primarily described as being performed by processor 50 of IMD 16, in other examples, processor 70 of programmer 24 or a processor of another computing device may perform any part of the techniques in FIGS. 5-10 or any other technique described herein. In addition, any of the techniques shown in FIGS. 5-10 for controlling the delivery of stimulation therapy to patient 14 to manage incontinence may be used in combination with each other.

Figure 11:
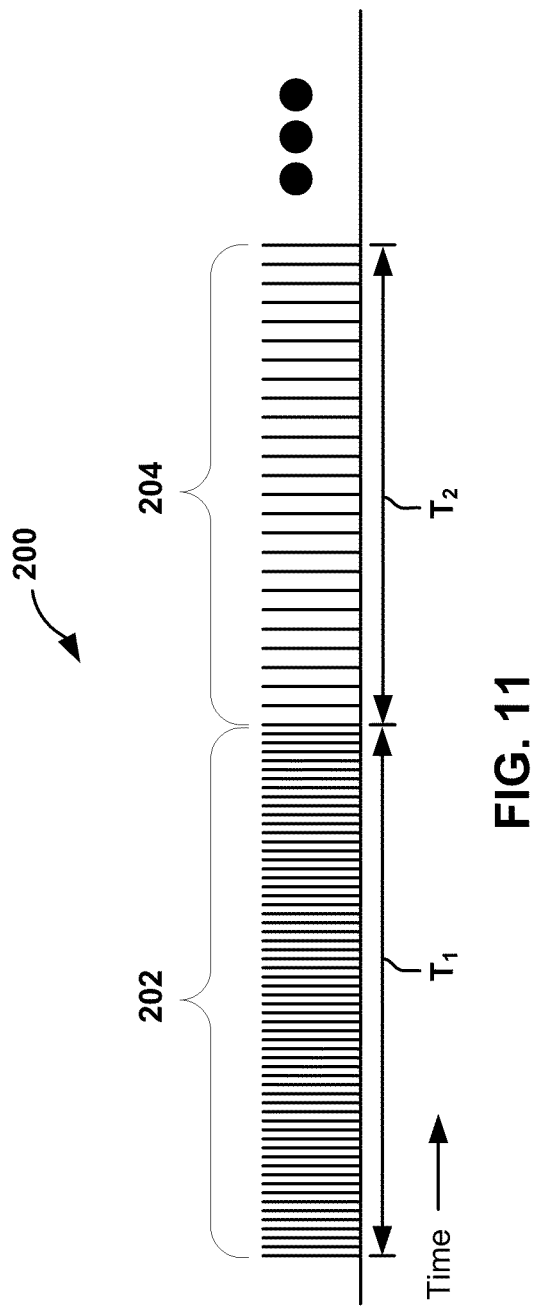
FIGS. 11, 12, 13A-13C, and 14A-14C illustrate example stimulation signals that may be delivered as part of a second stimulation therapy.

FIG. 11 illustrates an example stimulation signal 200 that therapy delivery module 52 of IMD 16 may generate and deliver as part of the second stimulation therapy. Stimulation signal 200 includes stimulation pulses 202 and stimulation pulses 204. In the example shown in FIG. 11, stimulation pulses 202 are delivered over an interval that has duration $T_1$ and stimulation pulses 204 are delivered over an interval that has duration $T_2$. Stimulation pulses 202 are delivered at a higher frequency than stimulation pulses 204. The high frequency stimulation pulses 202 may be designed to maximize closure of the urinary sphincter or bladder outlet while the low frequency stimulation pulses 204 may be designed to minimize muscle fatigue. By alternating the delivery of the high and low frequency stimulation pulses 202, 204, respectively, the second stimulation therapy may be configured to reduce muscle fatigue while minimizing the possibility of an occurrence of an involuntary voiding event.

As previously indicated, IMD 16 may deliver the second stimulation therapy for a predetermined therapy period. In some examples, during the therapy period, IMD 16 may provide the first stimulation therapy to patient 14 by delivering stimulation pulses 202 at a frequency of approximately 40 Hz to approximately 66 Hz for a duration of approximately 10 seconds to 20 seconds, and subsequently deliver stimulation pulses 204 at a frequency of approximately 30 Hz for a duration of approximately 10 seconds to approximately 20 seconds. Other stimulation parameters are contemplated.

Additionally, although the stimulation pulses of stimulation signal 200, i.e., relatively high frequency stimulation pulses 202 and relatively low stimulation pulses 204, are shown in FIG. 11 as a continuous train of pulses, stimulation pulses may also be delivered in other configurations, such as bursts of pulses. For example, one or both of stimulation pulses 202 and 204 may be delivered as bursts of pulses. The bursts of pulses may be controlled, for example, by selecting duty cycle values, e.g., approximately 50% ON/50% OFF, approximately 30% ON/70% OFF, or approximately 20% ON/80% OFF.

Figure 12:
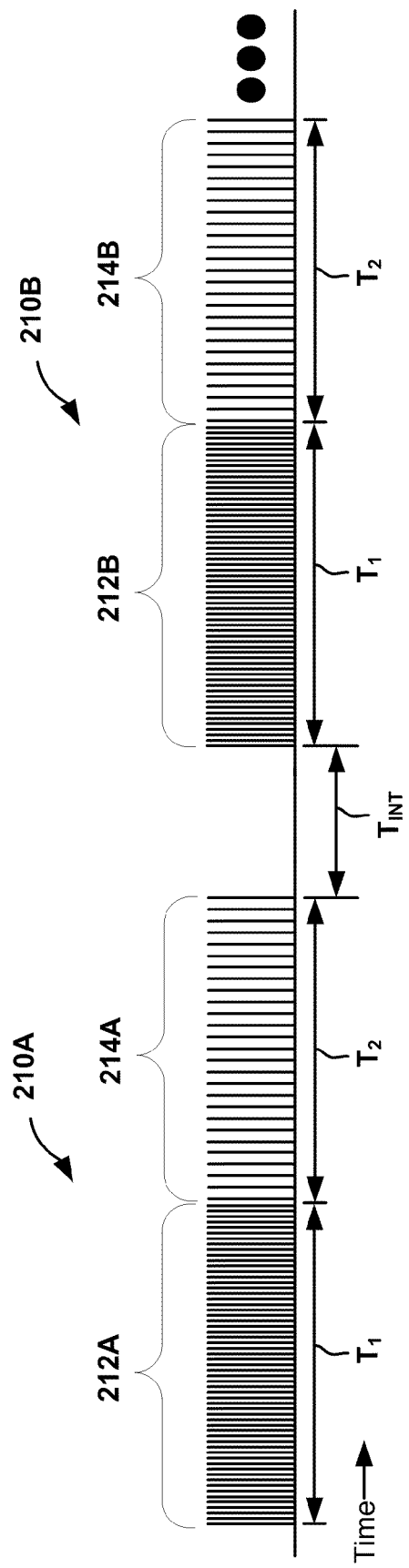

FIG. 12 illustrates example stimulation signals 210A and 210B that therapy delivery module 52 of IMD 16 may generate and deliver as part of the second stimulation therapy. Stimulation signal 210A includes bursts of relatively high frequency stimulation pulses 212A and relatively low frequency stimulation pulses 214A. Stimulation signal 210B includes bursts of relatively high frequency stimulation pulses 212B and relatively low frequency stimulation pulses 214B. In the example shown in FIG. 12, stimulation signals 210A and 210B are similar to stimulation signal 200 shown in FIG. 11 and, thus, are also similar to each other.

As shown in FIG. 12, IMD 16 does not deliver stimulation during the inter-therapy interval, $T_{INT}$, following the delivery of stimulation signal 210A. IMD 16 delivers stimulation signal 210B at the expiration of the inter-therapy interval $T_{INT}$. By not delivering stimulation during $T_{INT}$, muscle fatigue may be minimized in comparison to delivering stimulation substantially continuously during a therapy interval. An inter-therapy interval, such as $T_{INT}$, may be approximately 10 seconds in some examples. In other examples, an inter-therapy interval may be more or less than 10 seconds. In any case, the purpose of an inter-therapy interval is to deliver no or minimal stimulation so as to minimize muscle fatigue.

Figure 13A:
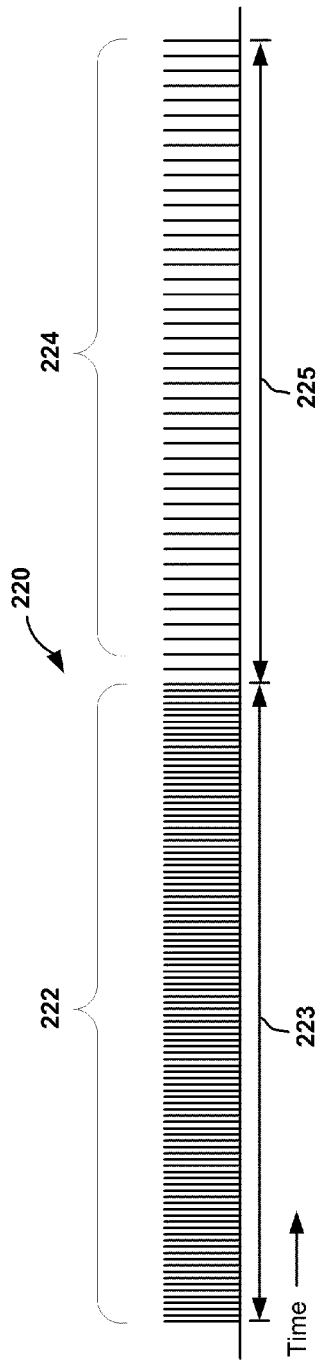
Figure 13B:
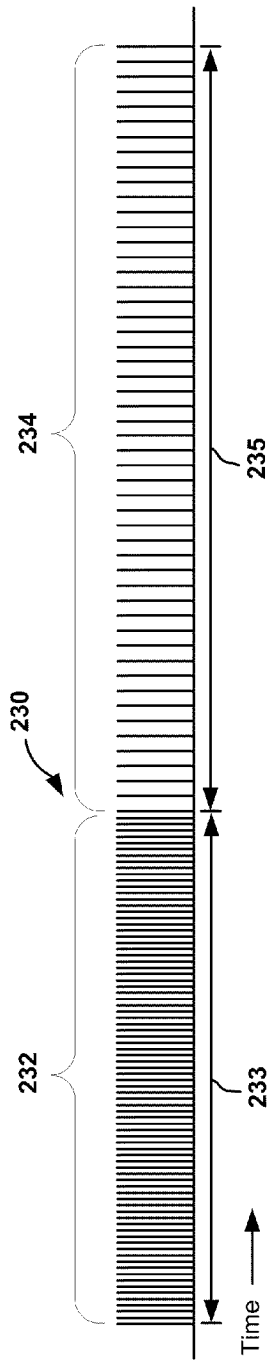
Figure 13C:
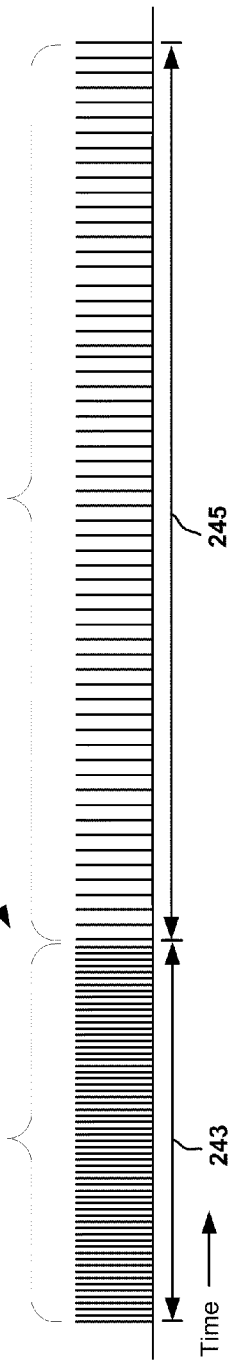

FIGS. 13A-13C illustrate example stimulation signals that IMD 16 may deliver as part of the second stimulation therapy in an adaptive fashion so as to minimize muscle fatigue. In particular, FIGS. 13A-13C illustrate example stimulation signals 220, 230, and 240, respectively. Stimulation signals 220, 230, and 240 may be delivered sequentially. In particular, stimulation signals 230 and 240 may be delivered within an inter-therapy interval (e.g., about 30 seconds) of the previous stimulation signal that was delivered as part of the second stimulation therapy. That is stimulation signal 230 may be delivered after expiration of the inter-therapy interval that began after delivery of stimulation signal 220 and stimulation signal 240 may be delivered after expiration of the inter-therapy interval that began after delivery of stimulation signal 230.

As discussed with respect to FIG. 10, in some examples, processor 50 adjusts one or more parameters of the second stimulation therapy if IMD 16 has previously delivered the second stimulation therapy within the interval of time. Adjusting one or more parameters of the second stimulation therapy help minimize patient adaptation to the second stimulation therapy, as well as any muscle fatigue that may result from the second stimulation therapy. FIGS. 13A-1C provide an example of adaptive second stimulation therapy in which, for each subsequent stimulation signal triggered within an inter-therapy interval of the previous second stimulation therapy delivery period, the duration of fast-twitch muscle stimulation decreases by a predetermined amount, e.g., five seconds.

In FIGS. 13A-13C the stimulation pulses that stimulate fast-twitch muscles are the stimulation pulses of relatively high frequency, i.e., bursts 222, 232, and 242. As shown in FIGS. 13B and 13C, the time interval 233 for stimulation pulses 232 has decreased in comparison to the time interval 223 for stimulation pulses 222, and the time interval 243 for stimulation pulses 242 has decreased in comparison to timer interval 233 for stimulation pulses 232. Accordingly, the time interval 235 for relatively low frequency stimulation pulses 234 has increased in comparison to the time interval 225 for relatively low frequency stimulation pulses 224, and the time interval 245 for relatively low frequency stimulation pulses 244 has increased in comparison to timer interval 235 for stimulation pulses 234.

Because the time interval for the high frequency stimulation pulses decreases and the time interval for the low frequency stimulation pulses increases for each subsequent stimulation signal, the duration of time that the fast twitch muscles are activated is minimized, which may help minimize muscle fatigue.

Figure 14A:
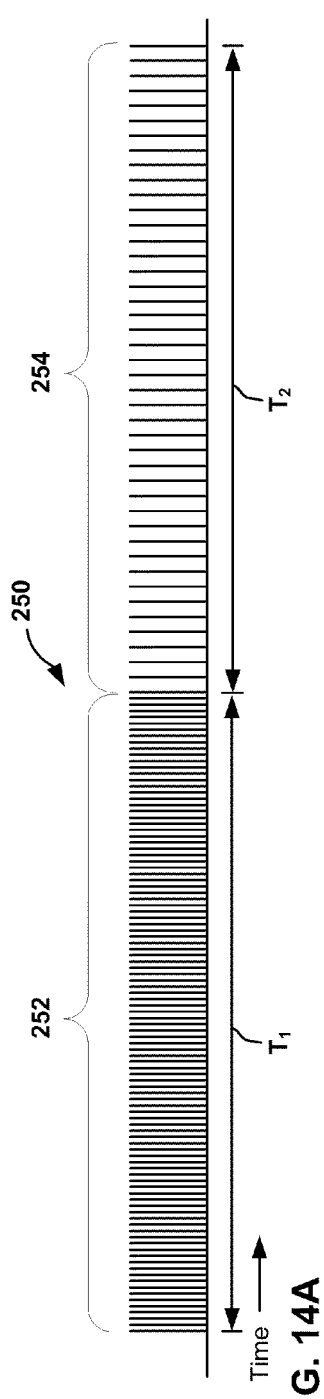
Figure 14B:
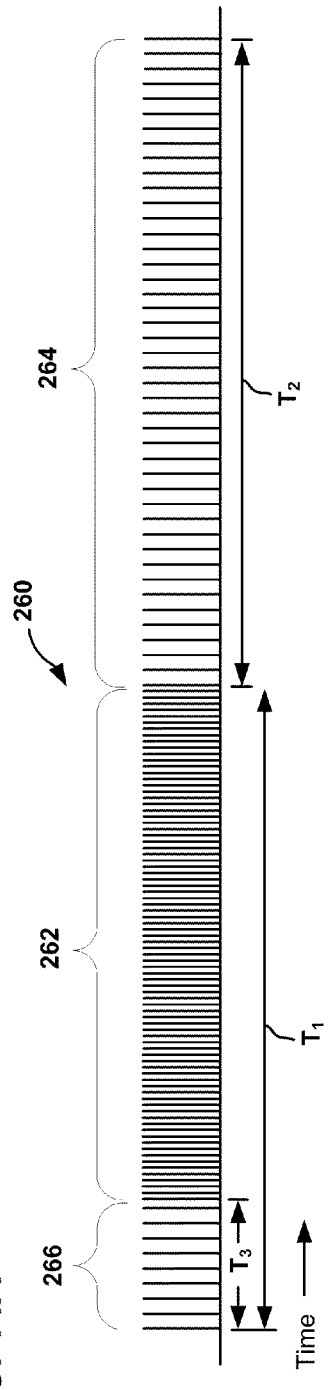
Figure 14C:
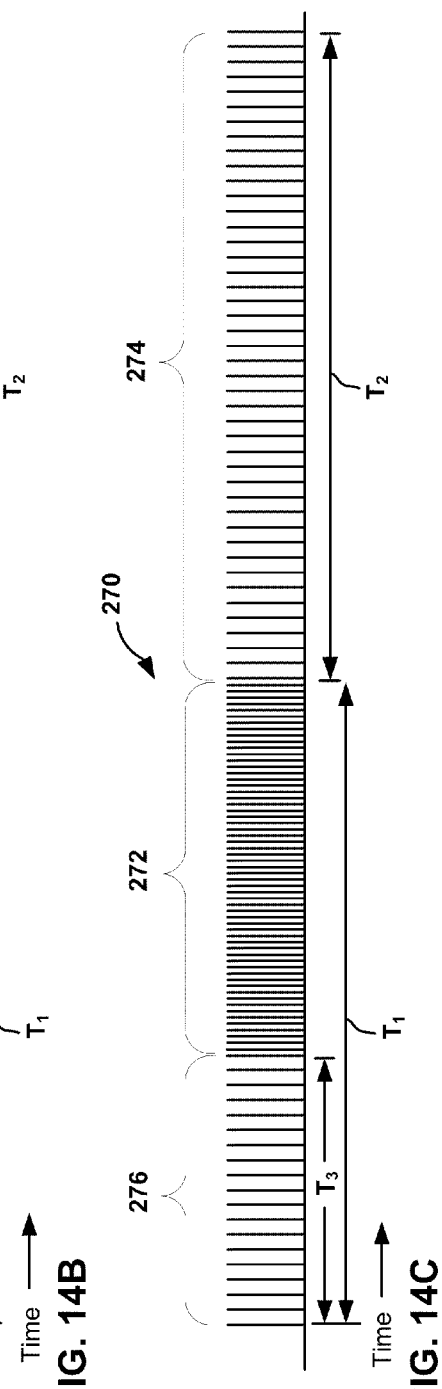

FIGS. 14A-14C illustrate another set of example of stimulation signals IMD 16 may generate and deliver as part of adaptive stimulation therapy to help minimize muscle fatigue. In particular, FIGS. 14A-14C illustrate example stimulation signals 250, 260, and 270, respectively. As with the example stimulation signals shown in FIGS. 13A-13C, stimulation signals 250, 260, and 270 may be delivered sequentially, e.g., such that signal 260 is delivered subsequent to signal 250, and signal 270 is delivered subsequent to signal 260.

Signals 250, 260, and 270 in FIGS. 14A-14C are also similar to the signals in FIGS. 13A-C in the sense that, for each subsequent signal, the number of high frequency stimulation pulses decreases and the number of low frequency stimulation pulses increases. However, the manner in which processor 50 of IMD 16 adjusts the signals 250, 260, and 270 over time is different than that for signals 220, 230, and 240. Specifically, for each subsequently delivered signal, a first portion of the relatively high frequency stimulation pulses is replaced with relatively low frequency stimulation pulses compared to the previous signal.

In FIGS. 14A-14C, $T_1$ defines an interval during which bursts of relatively high frequency stimulation pulses are delivered during delivery of standard second stimulation therapy, i.e., non-adaptive second stimulation therapy. Interval $T_2$ defines an interval during which relatively low frequency stimulation pluses are delivered for both non-adaptive and adaptive second stimulation therapy. When processor 50 modifies the stimulation signals to provide adaptive second stimulation therapy, processor 50 replaces, for each subsequent signal, a first portion of the high frequency stimulation pulses with low frequency stimulation pulses. The time interval within $T_1$ during which processor 50 delivers low frequency stimulation pulses is labeled $T_3$.

Accordingly, stimulation signal 250 in FIG. 14A includes relatively high frequency stimulation pulses 252 during interval $T_1$, and relatively low frequency stimulation pulses during interval $T_2$. Example stimulation signal 260 in FIG. 14B represents an adapted stimulation signal delivered subsequent to signal 250. Signal 260 includes relatively low frequency stimulation pulses 266 that precede the relatively high frequency stimulation pulses 262 during interval $T_1$. Relatively low frequency stimulation pulses 266 are delivered over interval $T_3$ within interval $T_1$. If processor 50 determines that another therapy period of the second stimulation therapy is desirable after signal 260 is delivered to patient 14, processor 50 may further adapt stimulation signal 260.

In the example shown in FIG. 14C, processor 50 modifies stimulation signal 260 such that relatively low frequency stimulation pulses 276, which precede relatively high frequency stimulation pulses 272 during interval $T_1$, are delivered for approximately twice as long as the relatively low frequency stimulation pulses 266 that precede the relatively high frequency stimulation pulses 262 in stimulation signal 260. That is, the duration of interval $T_3$ for stimulation signal 270 is approximately twice the duration of interval $T_3$ for stimulation signal 260. Interval $T_3$ may generally be selected to have an initial value and to increase for each subsequent adaptive stimulation signal by that initial value. In this way, $T_3$ increases in a way that may allow effective therapy to be delivered while minimizing muscle fatigue. The initial value of interval $T_3$ may be a fraction of interval $T_1$ and, more particularly, may be selected to allow a number of adaptive stimulation signal to be delivered before the value of $T_3$ approaches the value of $T_1$. Other values for $T_3$ and algorithms for modifying the value of $T_3$ for delivering adaptive stimulation are contemplated.

Although not shown in FIGS. 14A-14C, in some examples, this adaptive pattern may continue for subsequently delivered stimulation pulses until low frequency stimulation pulses have replaced all relatively high frequency stimulation pulses during interval $T_1$, or, in other words, until the interval $T_3$ equals interval $T_1$. In such examples, any subsequently delivered stimulation pulses may include only low frequency stimulation pulses. In other examples, however, processor 50 may continue to adjust the stimulation signal, but maintain at least some relatively high frequency stimulation signals to activate the fast twitch muscle fibers. Processor 50 may reset the adaptive pattern of stimulation signals after a certain period of time of not triggering the second stimulation therapy. That is, processor 50 may deliver the second stimulation in an adaptive fashion when the second stimulation is triggered within a therapy interval, and continue to deliver second stimulation in an adaptive fashion as long as the second stimulation is triggered within consecutive therapy intervals. However, when second stimulation therapy is not triggered during a therapy interval, processor 50 may reset the adaptive pattern so that the next time second stimulation therapy is delivered in accordance with a non-adapted signal, e.g., signal 250.

The example stimulation signals shown in FIGS. 13A-13C and 14A-14C are merely examples. The purpose of these signals is to provide working examples to demonstrate the described techniques for providing two different types of stimulation therapy to manage patient incontinence.

In some cases, patient 14 may perceive the delivery of the second stimulation therapy or the transition from the delivery of the first stimulation therapy to the delivery of the second stimulation therapy, e.g., when the first and second stimulation therapies are delivered at different times (e.g., in a non-overlapping manner). Because the stimulation signals associated with the second stimulation therapy may have a higher intensity (e.g., a higher amplitude or frequency) than the stimulation signals associated with the first stimulation therapy, the initiation of the second stimulation therapy may cause discomfort to patient 14. The discomfort may or may not exceed a pain threshold of patient 14.

In order to help minimize the discomfort to patient 14 from the delivery of the second stimulation therapy or the transition from the first stimulation therapy to the second stimulation therapy, processor 50 of IMD 16 (FIG. 3) or a processor of another device (e.g., programmer 24) may control therapy module 52 (FIG. 3) of IMD 16 to gradually modify one or more stimulation parameter values (e.g., amplitude or frequency) over time, rather than abruptly (e.g., instantaneously) increase the parameter values relative to the one or more stimulation parameter values defined by the first stimulation therapy. That is, upon determining that delivery of the second stimulation therapy is desirable, e.g., in response to a sensed physiological condition or patient input, processor 50 of IMD 16 (or another device) may control therapy delivery module 52 to deliver therapy to patient 14 by gradually transitioning between the one or more stimulation parameter values of the first stimulation therapy to the one or more stimulation parameter values of the second stimulation therapy. In some examples, the transition from the first stimulation therapy delivery to the second stimulation therapy includes a ramping up of the amplitude and frequency of the stimulation signals. The amplitude, frequency or other stimulation parameter value (e.g., pulse width in the case of stimulation pulses) may be modified in a linear, nonlinear, exponential or step-wise manner.

Similarly, upon determining termination of the second stimulation therapy delivery is desirable (e.g., because of the termination of the therapy period or because of patient input indicating abortion of the second stimulation therapy is desirable), processor 50 (or another processor) may control therapy delivery module 52 to gradually transition from therapy delivery according to the one or more stimulation parameter values of the second stimulation therapy to the one or more stimulation parameter values of the first stimulation therapy. In some examples, the transition from the second stimulation therapy delivery to the first stimulation therapy includes a ramping down of the amplitude and frequency of the stimulation signals.

The gradual ramping upward or downward of the one or more stimulation parameter values is contrary to an instantaneous modification to the one or more stimulation parameter values. An immediate change in a stimulation parameter value may be characterized by, for example, a jump from therapy delivery according to a first stimulation parameter value to therapy delivery according to a second stimulation parameter value. In contrast, a gradual change in the stimulation parameter value may be accomplished by, for example, shifting from a stimulation parameter value defined by the first stimulation therapy to therapy delivery according to a second stimulation parameter value defined by the second stimulation therapy over time. The shift from the first stimulation parameter value to the second stimulation parameter value may involve, for example, therapy delivery according to intermediate stimulation parameter values between the first and second stimulation parameter values.

Various techniques may be used to transition between stimulation parameter values of the first and second stimulation therapies. In some examples, processor 50 of IMD 16 (or another device) utilizes a predetermined constant or variable rate of change to gradually ramp up or down between the stimulation parameter values (e.g., the amplitude and/or frequency) of the first and second stimulation therapies. In other examples, processor 50 may gradually increase or decrease a stimulation parameter value over a predetermined range of time (referred to as a transition time). By gradually adjusting a stimulation parameter value to a desired level over time rather than making an adjustment to a desired value substantially immediately, IMD 16 may effectively adjust the stimulation parameter value without patient 14 experiencing undesirable side effects that may result from making abrupt changes to a stimulation parameter, such as stimulation amplitude, too quickly.

In some cases, the first and second stimulation therapies define different stimulation signal amplitudes. Processor 50 of IMD 16 (or a processor of another device, such as programmer 24) may control therapy module 52 to shift from the first stimulation therapy to the second stimulation therapy by gradually shifting from a baseline amplitude (defined by the first stimulation therapy) to a second amplitude (defined by the second stimulation therapy) according to a predetermined pattern. Example patterns include, but are not limited to, a linear, non-linear or exponential rate of change. That is, processor 50 (or another processor) may gradually ramp the amplitude up or down using a linear, non-linear or exponential rate of change.

Similarly, in some cases, the first and second stimulation therapies define different stimulation signal frequencies in addition to or instead of the different amplitudes. Processor 50 of IMD 16 (or a processor of another device, such as programmer 24) may control therapy module 52 to shift from the first stimulation therapy to the second stimulation therapy by gradually shifting from a baseline frequency (defined by the first stimulation therapy) to a second frequency (defined by the second stimulation therapy) according to a predetermined pattern. Example patterns include, but are not limited to, a linear pattern, a nonlinear pattern or an exponential pattern. In addition, in some examples, patterns such as a step-wise pattern may be used to transition between stimulation parameter values.

In examples in which the first and second stimulation therapies define different stimulation signal frequencies and different amplitudes, processor 50 of IMD 16 (or another processor) may modify one or both the frequency and/or amplitude values at a time. For example, if the second stimulation therapy defines greater amplitude and frequency values than the first stimulation therapy, processor 50 may control therapy module 52 to gradually increase the stimulation amplitude over time (e.g., using a predetermined rate of change, as defined by a predetermined pattern, or over a predetermined duration of time) while maintaining the frequency defined by the first stimulation therapy. After the stimulation amplitude has reached a second amplitude value defined by the second stimulation therapy, processor 50 may deliver stimulation therapy according to the second amplitude value while controlling therapy module 52 to gradually increase the frequency over time until the frequency value of the second stimulation therapy is achieved.

In other examples, processor 50 may control therapy module 52 to gradually increase the stimulation signal frequency over time while maintaining a first amplitude value defined by the first stimulation therapy. After the frequency has reached a second frequency value defined by the second stimulation therapy, processor 50 may deliver stimulation therapy to patient 14 according to the second frequency while controlling therapy module 52 to gradually increase the amplitude over time until the amplitude value of the second stimulation therapy is achieved.

In other examples in which the first and second stimulation therapies define different stimulation parameter values, processor 50 of IMD 16 (or another processor) may modify all of the stimulation parameter values at the same time. In some cases, one of the stimulation parameter values is gradually changed over time while another is instantaneously changed. For example, upon determining the delivery of the second stimulation therapy is desirable, processor 50 of IMD 16 (or another processor) may gradually increase the stimulation amplitude (e.g., using a predetermined rate of change or over a predetermined duration of time) while applying the frequency of the second stimulation therapy at the onset of the second stimulation therapy delivery. That is, processor 50 controls therapy module 52 to shift to the frequency of the second stimulation therapy immediately upon determining delivery of the second stimulation therapy is desirable.

In other examples, upon determining the delivery of the second stimulation therapy is desirable, processor 50 of IMD 16 (or another processor) may gradually increase the stimulation frequency (e.g., using a predetermined rate of change, as defined by a predetermined pattern, or over a predetermined duration of time) while applying the amplitude of the second stimulation therapy at the onset of the second stimulation therapy delivery. In this way, processor 50 controls therapy module 52 to shift to the amplitude value of the second stimulation therapy immediately upon determining delivery of the second stimulation therapy is desirable.

While techniques for transitioning from the first stimulation therapy to the second stimulation therapy are described above, similar techniques may also be applied to transitioning from the second stimulation therapy to the first stimulation therapy upon determining the termination of the second stimulation therapy is desirable. As previously indicated, the first stimulation therapy periodically over an extended period of time, e.g., chronic stimulation and the second stimulation therapy is periodically delivered to patient 14 to provide a short-term boost to the effectiveness of the first stimulation therapy. Thus, termination of the second stimulation therapy may be desirable after a predetermined therapy period in which the second stimulation therapy is delivered (in an overlapping or non-overlapping manner with the first stimulation therapy) or in response to patient input indicating the termination of the second stimulation therapy is desirable.

Other techniques may be used to minimize patient comfort resulting from the onset of the second stimulation therapy instead or in addition to gradually ramping up or down of one or stimulation parameter values when transitioning between the first and second stimulation therapies. In some examples, IMD 16 may implement prepulse inhibition in order to minimize the perception of the shift between the stimulation parameter values of the first stimulation therapy to the increased stimulation parameter values of the second stimulation therapy. Prepulse inhibition is a neurological phenomenon in which a weaker prestimulus (also referred to as a prepulse) inhibits the reaction of an organism to a subsequent stronger stimulus (e.g., a stimulation signal of the second stimulation therapy).

FIG. 15 is a conceptual illustration of example stimulation signals that therapy delivery module 52 of IMD 16 may generate and deliver as part of the second stimulation therapy. In the example shown in FIG. 15, the IMD 16 delivers prestimulus 280 prior to delivering stimulation signal 200, which generates the second physiological effect (e.g., promotion of internal urinary sphincter contraction) associated with the second stimulation therapy. As described with respect to FIG. 11, in some examples, stimulation signal 200 includes stimulation pulses 202 and stimulation pulses 204, which have a lower frequency than stimulation pulses. Other stimulation signals may be used instead of or in addition to stimulation signal 200 to provide the second stimulation therapy.

Prestimulus 280 includes one or more stimulation signals (e.g., pulses) that are delivered before each therapy period of the second stimulation therapy in order to substantiate the central perception inhibition effect. In the example shown in FIG. 15, prestimulus 280 includes a single stimulation pulse that is delivered about 1 ms to about 25 ms prior to the delivery of stimulation signal 200. If the second stimulation therapy is delivered for more than one consecutive therapy period, e.g., as described with respect to FIG. 12, processor 50 of IMD 16 (or another device) may control therapy module 52 to deliver prestimulus 280 prior to each therapy period.

In general, prestimulus 280 includes one or more stimulation signals having a smaller intensity than stimulation signal 200 delivered as part of the second stimulation therapy. Stimulation intensity may be a function of, e.g., defined by, for example, the amplitude and/or frequency of a stimulation signal. In the example shown in FIG. 15, prestimulus 280 includes a single stimulation pulse that has an amplitude that is about 0.10 to 0.50 of the amplitude of the stimulation signals 200. In other examples, IMD 16 can deliver a single prepulse (e.g., as shown in FIG. 15) or a prestimulus train of pulses similar to pulse 280 shown in FIG. 15 (e.g., about two to about 100 pulses) to patient 14 before the first stimulation therapy period of a plurality of consecutive second stimulation therapy periods, or during a second stimulation therapy period, rather than before each therapy period as described with respect to FIG. 15.

In addition to or instead of the gradual modification of stimulation parameter values and the prepulse inhibition, electrical nerve block may be used to minimize discomfort to patient 14 that may result from the delivery of the second stimulation therapy. For example, IMD 16 may deliver a relatively high frequency stimulation via one or more electrodes 29 (FIG. 3) or a separate set of electrodes to a tissue site proximal to the target stimulation site for the second stimulation therapy (e.g., a tissue site closer to the spinal cord than the target stimulation site) and along the same nerve targeted by the second stimulation therapy. Electrical nerve block may help block conduction along the nerve to minimize perception of the delivery of the second stimulation therapy by patient 14.

The nerve block may be achieved via a high frequency stimulation signal having a frequency of about 200 Hz to about 20 kHz, although other frequency ranges are contemplated and may be specific to patient 14. Delivery of high frequency nerve block may be useful to initiate a relatively rapid onset of nerve conduction that is temporally correlated with the delivery of the second stimulation therapy, thereby providing relevant nerve conduction block. In some examples, processor 50 of IMD 16 (or another device) may control therapy module 52 to initiate the delivery of the high frequency stimulation to achieve the nerve block before or at the onset of the second stimulation therapy. In some examples, the high frequency nerve block may be maintained throughout the delivery of the second stimulation therapy period. In other examples, a device separate from IMD 16 may deliver the stimulation to block nerve conduction. In addition, nerve block stimulation other than high frequency stimulation, such as anodal block stimulation, may also be used.

Other techniques may also be used to minimize discomfort to patient 14 that may result from the delivery of the second stimulation therapy in addition to or instead of the techniques described above. In some examples, other innocuous stimulation is delivered before or at the onset of the second stimulation therapy. For example, in some examples, an outer housing of IMD 16 vibrates during the second stimulation therapy period in order to help minimize the discomfort to patient 14. The vibration of outer housing of IMD 16 may produce paresthesia near the target tissue site for the second stimulation therapy in examples in which IMD 16 is implanted near the target tissue site. IMD 16 may vibrate at a frequency of about 1 Hz to about 200 Hz, although other frequency ranges are contemplated.

In yet other examples, IMD 16 or another device delivers stimulation to tissue sites within patient 14 other than the target tissue site for the second stimulation therapy in order to minimize the discomfort to patient 14 from the delivery of the second stimulation therapy. Different stimulation frequencies for the delivery of stimulation to the relevant tissue site (which may be internal or external) may elicit different patient responses. For example, a relatively low frequency stimulation may activate muscle tissue and/or reduce pain resulting from the second stimulation therapy by stimulating the production of endogenous endorphins, and a relatively high frequency stimulation may produce paresthesia.

In some examples, IMD 16 or another device (e.g., a separate microstimulator or external medical device coupled to external or subcutaneous electrodes) delivers stimulation to a dermatome associated with the target nerve for the second stimulation therapy (e.g., a hypogastric nerve, a pudendal nerve, a dorsal penile nerve in a male patient, a dorsal clitoral nerve in a female patient). A dermatome can be an area of skin that is supplied by the target nerve. Delivery of stimulation to the dermatome may, for example, produce paresthesia or produce endogenous endorphins that help reduce pain perceived by patient 14. In examples in which IMD 16 delivers the stimulation to the dermatome, IMD 16 can deliver the stimulation to the dermatome using select electrodes of a lead that is separate from the lead (e.g., lead 28 in FIG. 1) that delivers the second stimulation therapy to patient 14.

As another example, for female patients, a vaginal plug can be used to deliver stimulation during the second stimulation therapy period in order to help minimize the discomfort to patient 14, e.g., by producing paresthesia. If a device separate from IMD 16 is used to deliver the stimulation to patient 14 that is used to minimize discomfort to patient 14, the separate device may be external or implanted within patient 14, and may communicate with IMD 16 via a wired connection or a wireless communication technique (e.g., RF communication techniques).

Figure 16:
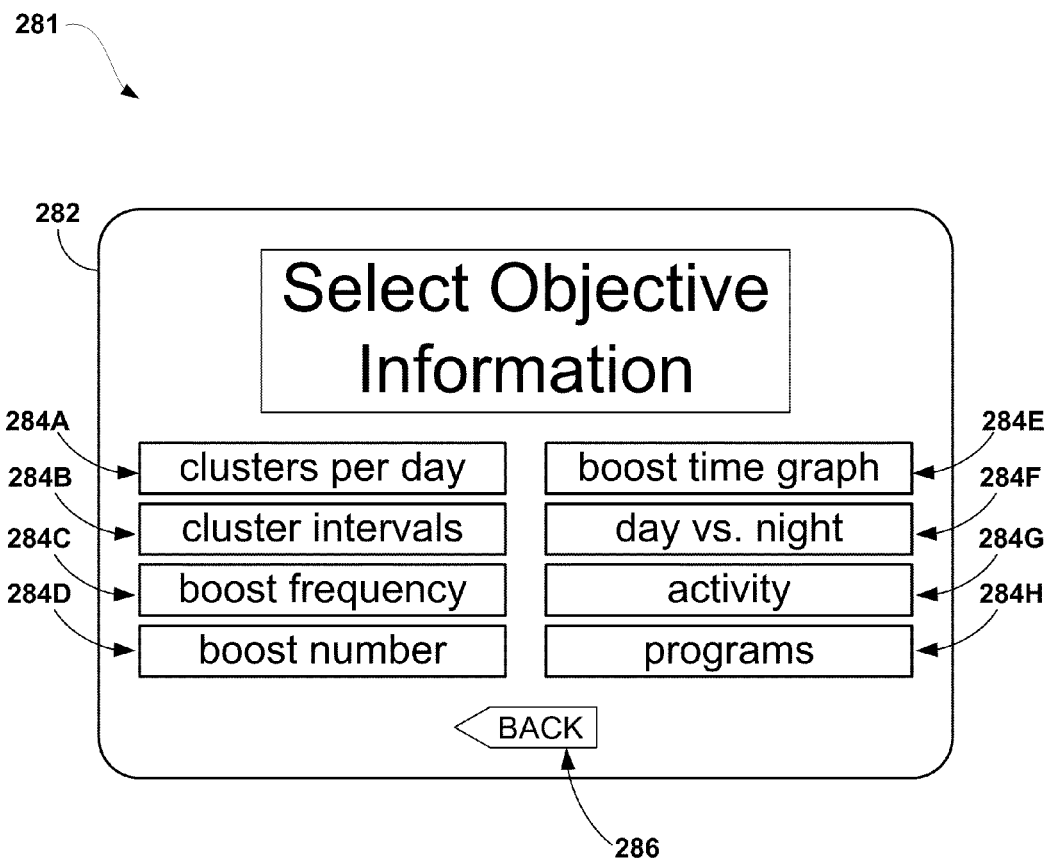
FIG. 16 illustrates an example user interface that allows a user to select a format for objective incontinence information generated based on trigger event data.

FIG. 16 illustrates example user interface 281 that allows a user to select a format for displaying objective incontinence information. As shown in FIG. 16, user interface 281 includes screen 282 that presents a menu for selecting the format of objective incontinence information to be presented. User interface 281 is an example of user interface 74 of FIG. 4 and may be presented on programmer 24 or any other computing device configured to present objective incontinence information to a user. For example, user interface 281 may used by a patient programmer, a clinician programmer, or another computing device. While certain functions are described as being performed by objectification module 75 (FIG. 4), in other examples, processor 70 or a processor of another computing device may perform these functions.

In the example of FIG. 15, the user may select from eight different formats in which the objective incontinence information may be presented. These eight formats may be chosen by selecting one of format inputs 284A-284H (collectively "format inputs 284"). Format inputs 284 may be arranged in any spatial manner on screen 282 in other embodiments. Other examples of screen 282 may include greater or fewer number of formats selection by a user. In some examples, the user may configure screen 282 to include only the formats generally used during treatment of patient 14.

Upon receiving user input selecting format input 284A, objectification module 75 generates and presents objective incontinence information via user interface 74 in the form of the number of clusters per day. As described above, a cluster includes the trigger events that occurred within a specific cluster window or cluster interval that occurs before a voiding event in patient 14. Upon receiving user input selecting format input 284B, objectification module 75 generates and presents objective incontinence information in the form of the cluster intervals, e.g., the median, average or exact duration between each cluster in a certain period of time (e.g., a day, week, or month). Upon receiving user input selecting format input 284C, objectification module 75 generates and presents objective incontinence information in the form of the average boost frequency, e.g., trigger event frequency, for each individual trigger event or cluster of trigger events.

Upon receiving user input selecting format input 284D, objectification module 75 generates and presents objective incontinence information in the form of the number of boosts, e.g., trigger events, per cluster. Upon receiving user input selecting format input 284E, objectification module 75 generates and presents objective incontinence information in the form of a boost time graph that illustrates the number of trigger events over time, e.g., the past day, the past week, the past month, or other selected time period. Upon receiving user input selecting format input 284F, objectification module 75 generates and presents objective incontinence information in the form of clusters of trigger events during the day versus clusters of trigger events during the night. Day and night may be specified as to particular hours or when patient 14 is sleeping. In other examples, format input 284F may be associated with the generation of objective incontinence information that organizes the trigger events (individual or clusters in different examples) by times of day other than "day" and "night." Examples times of day can include, for example, a breakdown of hours of the day, or a more meaningful grouping of hours. Upon receiving user input selecting format input 284G, objectification module 75 generates and presents objective incontinence information in the form of clusters for each type of activity detected by system 10. In addition, upon receiving user input selecting format input 284H, objectification module 75 generates and presents objective incontinence information in the form of trigger events or clusters associated with each stimulation therapy program used or evaluated by patient 14.

In other examples, screen 282 may include graphical objects that can be selected to provide objective incontinence information in different forms than those listed by format inputs 284. For example, screen 282 may provide a graphical object associated with a format of clusters ranked by severity, frequency, or trigger events. In some examples, other trigger event data in addition to the trigger event occurrences can also be displayed, such as sensed bladder condition, sensed physiological condition, sensed patient activity, sensed patient posture, or other objective data is contemplated as part of objective incontinence information that may be presented by user interface 281. This objective incontinence information may be displayed in any graphical, numerical, or textual format desired by a manufacturer, clinician, healthcare technician, or user.

Screen 282 also includes back input 286 that, when selected, returns the user to the previous screen of user interface 281. The previous screen may be, for example, a menu or sub-menu that provides the option to select the format of objective incontinence information in screen 282. In other examples, screen 282 may provide additional navigation options for the user. For example, screen 282 may provide an option for selecting the formats listed in screen 282 or even to skip directly to suggested therapy programs or automatic selection of an effective therapy program without first viewing the objective incontinence information. In addition, user interface 281 may provide additional operational information on screen 282, such as a battery indicator for IMD 16 and or programmer 24, an stimulation indicator, a link indicator that indicates an active link between IMD 16 and programmer 24, or any other indicator related to objective incontinence information or operation of programmer 24.

Although any type of trigger event may be used to generate the objective incontinence information, trigger events initiated by patient input may be of interest to clinicians in some examples. Therefore, in some examples in which therapy system 10 is configured to activate the second stimulation therapy (e.g., provide a "boost") based on trigger events from patient input and sensor input, external programmer 24 may be configured to generate objective incontinence information with trigger events only from patient input requesting the second incontinence stimulation therapy. Patient 14 may initiate the delivery of the second stimulation therapy for many reasons. In some cases, patient 14 may be afflicted with urge incontinence, and upon perceiving an urge to void, patient 14 may provide input that causes IMD 16 to deliver the second stimulation therapy. The second stimulation therapy may provide an additional "boost" of stimulation that helps prevent the leakage of urine from bladder 12, e.g., by contracting internal urinary sphincter 13 and the external urinary sphincter 11. In this way, therapy system 10 provides patient 14 with direct control of the incontinence therapy. Therefore, a patient input requesting the second stimulation therapy may be a useful indication of the patient's perception of the first stimulation therapy efficacy. In some cases, patient 14 may be able to detect physiological conditions not easily detected by a sensor or the patient perception of a particular physiological condition detected based on a sensed physiological parameter may differ between patients. That is, while a physiological parameter sensed by a sensor can be useful for controlling therapy delivery in some examples, the patient condition determined based on the sensed physiological parameter may not be calibrated to the patient's perception, such that for one patient, a particular physiological parameter value may indicate a more severe incontinence event than for another patient. Because the therapy may be designed to improve the quality of life of patient 14, objective incontinence information generated from patient input alone may be useful for evaluating the efficacy of therapy system 10 in mitigating the effects of urinary (or fecal) incontinence.

FIGS. 17-22 illustrate various examples of user interfaces that present objective incontinence information in some format. Each of these user interfaces are only examples of possible formats for presenting objective incontinence information derived from trigger events and, in some examples, other sensed or obtained data. In addition, objective incontinence information may include therapy programs, groups of therapy programs, or even individual therapy parameters associated with the trigger events or other sensed data. While FIGS. 17-22 are described as illustrate objective incontinence information related to clusters of trigger events, in other examples, programmer 24 or another computing device can display objective incontinence information that relates to individual trigger events that are not clustered together in addition to or instead of the information relating to the clusters.

Figure 17A:
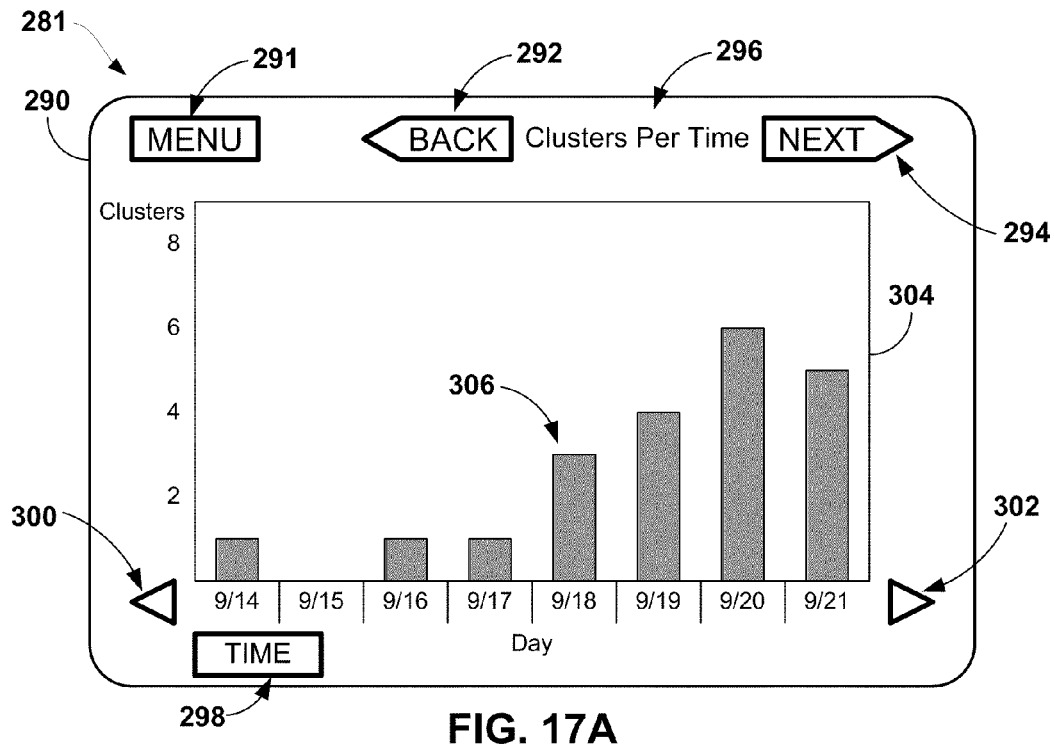
FIGS. 17A and 17B illustrate example user interfaces that display objective incontinence information as clusters and frequencies of trigger events over time.

FIG. 17A illustrates example user interface 281 presenting screen 290 that displays objective incontinence information in the form of the number of trigger event clusters per day over a specific time period. In some examples, the specific time period can be selected by a user by interacting with user interface 74. In the example shown in FIG. 17A, screen title 296 indicates that "Clusters Per Time" is the objective incontinence information presented in screen 290. Clusters of trigger events may indicate situations in which the first stimulation therapy may not be sufficient to prevent an occurrence of involuntary voiding event.

In the example of FIG. 17A, objective data field 304 includes cluster bars 306 that graphically, e.g., via a bar graph, indicate the number of clusters recorded for each day. For example, cluster bars 306 indicate that there were four clusters of trigger events on September 19 (9/19). An increasing number of clusters on each subsequent day may suggest that the first stimulation therapy is no longer effective or is decreasing in efficacy over time. In other examples, objective data field 304 may include grid lines that intersect cluster bars 306 and/or numerical indications of the number of clusters above or within each of cluster bars 306. Instead of cluster bars 306, objective data field 304 may utilize a scatter plot, line graph or other format to indicate the number of clusters per time period.

Scroll arrows 300 and 302 allow the user to view objective incontinence information from different time periods. For example, the user may select scroll arrow 300 to move backward in time and view cluster data from other days during therapy. In other examples, user interface 281 may provide a scroll bar, allow swiping on a touch screen, or some other mechanism for moving through the time periods of objective data field 304. The time periods may also be changed by selecting time input 298. Time input 298 may provide a menu, e.g., a new screen or a pop-up window, that allows the selection of other time periods for display within objective data field 304. Time input 298 may allow the user to change the time period between hours, days, weeks, months, quarters, years, time between clinician visits, or time between changes in the therapy program used to deliver the first stimulation therapy. The user may even define specific time periods. In other examples, time input 298 may be used to define the number of time periods viewable on objective data field 304.

User interface 281 also allows the user to navigate away from screen 290. Screen 290 includes menu input 291 that, when selected, either brings the user back to a main menu or presents the user with a list of optional screens to which the user may navigate. The user may also navigate between objective incontinence information screens of user interface 281 with back button 292 and next button 294. Selection of back button 292 may navigate back to a previous screen and next button 294 may navigate to the next screen of objective incontinence information. The order of objective incontinence information screens within user interface 281 may be preset by the manufacturer, clinician, or patient, or the order and availability of certain screens may depend upon the type of objective incontinence information available to the user.

Figure 17B:
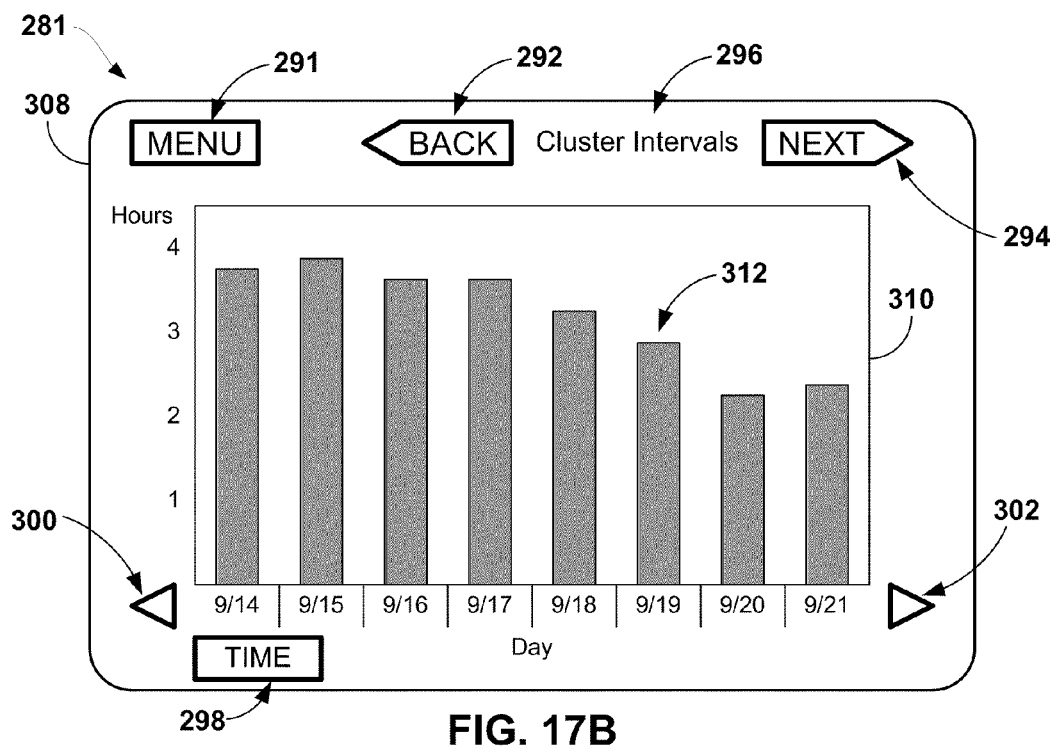

FIG. 17B illustrates example user interface 281 presenting screen 308 that provides the average interval between clusters during each day. Screen 308 of FIG. 17B is similar to screen 290 of FIG. 17A, and screen 308 also includes menu input 291, back button 292, next button 294, time input 298, and scroll arrows 300 and 302. Screen 308 of user interface 281 generally presents objective incontinence information in the form of an average cluster interval for each time period. Screen title 296 reflects this information as indicated in "Cluster Intervals."

The interval of time between clusters may be representative of the bladder capacity, and, therefore, maybe used to monitor changes in cluster intervals to identify problems with a patient condition. In addition, the interval of time between a voluntary voiding event and a subsequent cluster of trigger events (e.g., the next trigger event in time and prior to another voluntary voiding event) may be representative of the bladder capacity of patient 14 because the trigger event may be generated when bladder 12 of patient 14 is full or nearly full or when patient 14 perceives bladder 12 to be full or nearly full. Thus, shortly after emptying bladder 12 (e.g., after a voluntary voiding event, which can be detected based on patient input via IMD 16 or via programmer 24 or another external device), there may be an absence of trigger events until bladder is full or nearly full or patient 14 perceives bladder 12 to be full or nearly full. As a result, the time interval a voluntary voiding event and a subsequent cluster of trigger events may be indicative of the bladder fill cycle of patient 14. In this way, the objective incontinence information in the form of an interval of time between a voluntary voiding event and a subsequent cluster of trigger events or an average interval of time for a plurality of voiding events and respective subsequent cluster of trigger events may be useful for monitoring parameters of bladder filling (e.g., frequency of filling, time to filling, and the like), which can be useful for monitoring changes in a patient condition.

In the example of FIG. 17B, objective data field 310 includes interval bars 312 that graphically, e.g., via a bar graph, indicate the average duration of the interval, in hours, between clusters recorded for each day within objective data field 310. For example, interval bars 312 indicate that the average interval between clusters on September 19 (9/19) was approximately three hours. The decreasing cluster interval may indicate that bladder capacity is decreasing over time and therapy may need to be adjusted. In other examples, objective data field 310 may include grid lines and/or numerical indications of the interval length above or within each of interval bars 312. Instead of interval bars 312, objective data field 310 may utilize a scatter plot, line graph or other format of data display to indicate the number of clusters per time period.

In addition, in other examples, the time intervals displayed by objective data field 310 can be representative of other types of time intervals, such as the median time interval between clusters of trigger events.

Figure 18A:
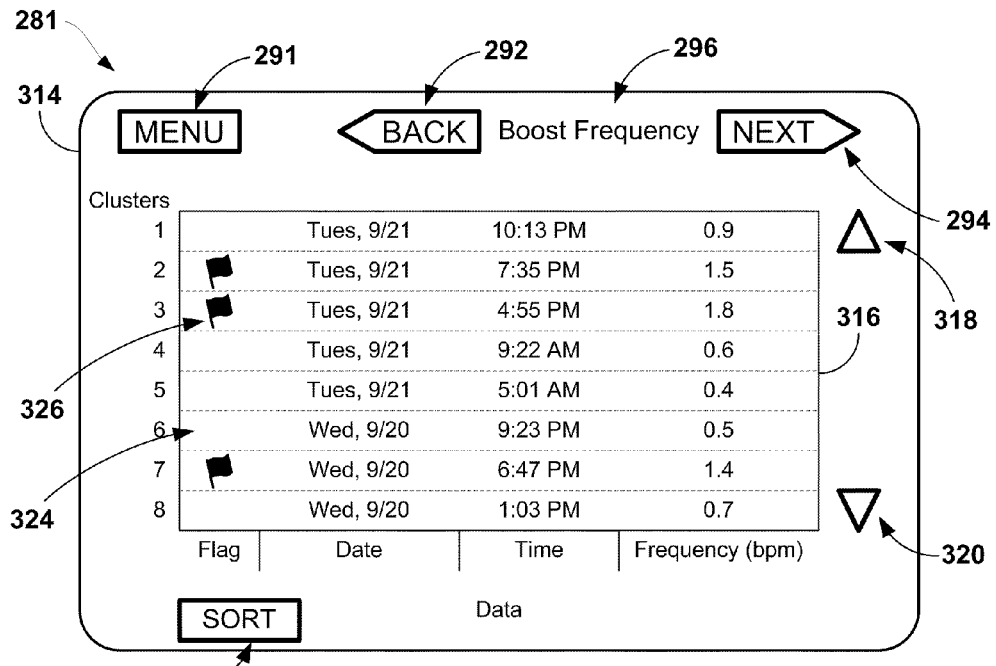
FIGS. 18A and 18B illustrate example user interfaces that display objective incontinence information as the frequency of trigger events and trigger events per cluster.

FIG. 18A illustrates example user interface 281 presenting screen 314 that provides objective incontinence information as frequencies of trigger events within each cluster. Screen 314 of FIG. 18A is similar to screen 290 of FIG. 17A, as screen 314 also includes menu input 291, back button 292, and next button 294. However, screen 314 presents textual and numerical information instead of the graphical information of screen 290. In general, screen 314 of user interface 281 presents objective incontinence information in the form of date, time, and trigger event ("boost") frequencies for each cluster. Screen title 296 reflects this information as indicated by "Boost Frequency." The frequency of trigger events within each cluster may indicate the frequency of bladder contractions for urinary incontinence. Therefore, trigger event frequency displayed by screen 314 may be indicative of changes in bladder contraction frequency. In some examples, bladder contraction frequency information gleaned from the objective incontinence information displayed by screen 314 can be useful for evaluating the patient condition (e.g., changes and progressions in the incontinence) or for adjusting therapy delivered by IMD 16 to be more efficacious.

In the example of FIG. 18A, objective data field 316 displayed within screen 314 includes text entries 324 that textually and numerically indicate the trigger event frequency for each recorded cluster. Objective data field 316 includes information for a plurality of recorded clusters (e.g., for a particular time range, which can be selected by a user, or for all clusters detected by objectification module 75 or processor 70) and presents additional data that identifies each cluster of text entries 324. Each text entry 324 of a single cluster includes data fields such as the date of the cluster, the time at which the cluster began, and the frequency of trigger events within the cluster. The frequency of trigger events is shown in boosts per minute (bpm), but any frequency may used to indicate the frequency with which trigger events occurred in the cluster.

Objective data field 316 can also include more robust information in addition into the more basic cluster identification information that helps a user more quickly identify clusters that meet a particular standard. In the example shown in FIG. 18A, objective data field 316 displays a flag 326 in the text entry 324 for clusters with a trigger event frequency above a predetermined threshold. For example, in the example shown in FIG. 18A, cluster 2 occurred on Tuesday, September 21, at 7:35 P.M., and cluster 2 is associated with flag 326 because the boost frequency is above the threshold frequency at 1.5 boosts per minute. In the example of FIG. 18A, the threshold frequency is set to 1.0 trigger events per minute so that flags 326 are presented in text entries 324 for each of clusters 2, 3, and 7. However, in other examples, the threshold frequency may be set to any desired frequency by a user. Alternatively, the threshold frequency may vary depending upon the detected frequencies of the trigger events. For example, the threshold frequency may be set so that 10 percent of clusters having the highest frequencies are flagged or the one or more clusters having the highest frequencies can be flagged.

In the example shown in FIG. 18A, objective data field 316 initially presents clusters in reverse chronological order. However, text entries 324 for the clusters may be sorted according to any of the different data fields within text entries 324. A user may select sort button 322 to specify the order in which each cluster is presented in objective field 316. For example, sort button 322 may, when selected, present a pop-up menu that allows the user to sort text entries 324 by date, time, or frequency. After the sort selection is made, user interface 281 may update objective data field 316 accordingly. Scroll arrows 318 and 320 may also allow a user to move through the complete list of all text entries 324, since all of them may not be visible at once within objective data field 316. In some examples, screen 314 may provide a scroll bar, scroll wheel, or even direct swiping on a touch screen to navigate within all of text entries 324 of objective data field 316. In some alternative examples, sort button 322 or another input may allow the user to select which types of data fields to display within each text entry 324. For example, the user remove flags 326, remove the time data field, and add a patient note data field that identifies a patient included note regarding specific clusters.

Figure 18B:
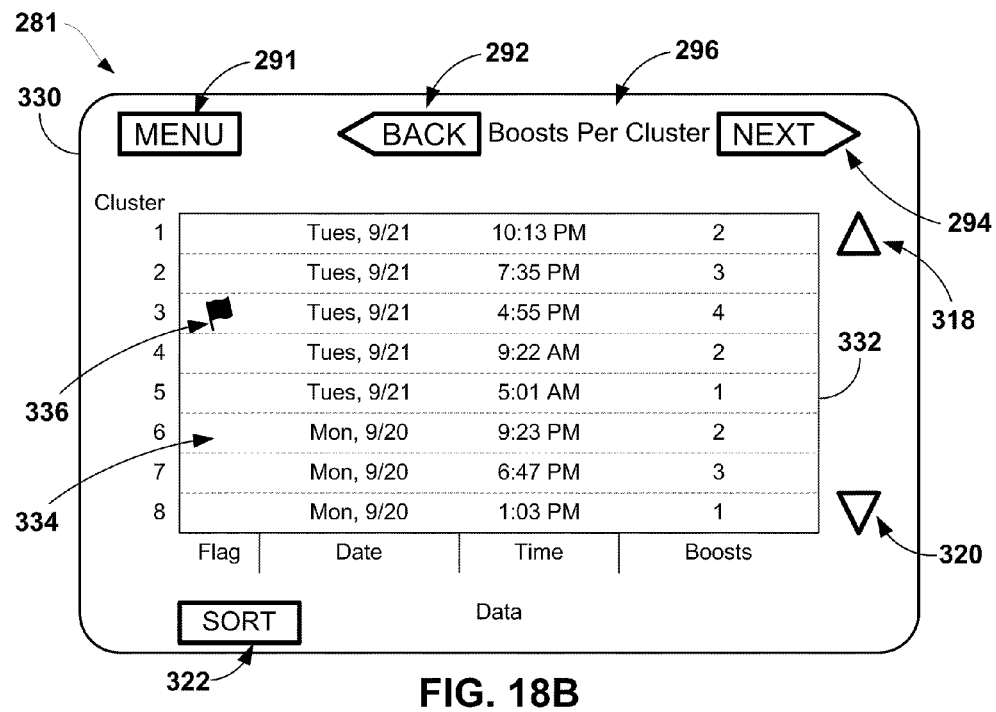

FIG. 18B illustrates example user interface 281 that presents screen 330 providing objective incontinence information as the number of trigger events per cluster. Screen 330 is similar to screen 314 of FIG. 18A, as screen 330 also includes menu input 291, back button 292, next button 294, sort button 322, and scroll arrows 318 and 320. However, screen 330 presents clusters and the actual number of trigger events, or "boosts," per cluster. Screen title 296 accordingly labels screen 330 for the user as "Boosts Per Cluster." The number of trigger events that makes up each cluster may indicate, for example, how many bladder contractions occurred before the imminent event terminated, or before patient 14 voluntarily voided. In some cases, more trigger events per cluster may indicate an insufficiency in the current therapy program to treat incontinence of patient 14.

Screen 330 also includes objective data field 332. Objective data field 332 is similar to objective data field 316 of FIG. 18A, but objective data field 332 displays the number of trigger events instead of the frequency of such trigger events for each cluster. Therefore, text entries 334 for each cluster includes the date and time of each cluster, the number of trigger events in the cluster, and a flag 336 if the number of trigger events is greater than a predetermined threshold. In the example of FIG. 18B, flag 336 is presented for cluster 3 because that cluster includes the threshold number of four trigger events. As discussed above with respect to FIG. 18A, objectification module 75 can generate flags 336 for cluster events based on different criteria in different examples. For example, the user may set the threshold number of trigger events to a desired threshold or the user may allow user interface 281 to automatically set the threshold number of trigger events so that a certain percentage or number of clusters are flagged for the user with flags 336.

In other examples of FIGS. 18A and 18B, each cluster (or even each trigger event of each cluster) may be presented as associated being with other sensed physiological data collected from patient 14. For example, IMD 16 may sense and store bladder pressure data, bladder fullness or volume data, electromyogram information, or patient 14 activity (e.g. movement activities and/or posture states). This sensed physiological parameter data may be presented in another column of objective data fields 316 or 332 for each cluster, in one example.

This sensed physiological parameter data may provide additional information regarding the physiological bladder state when the trigger events occurred. For example, if a trigger event or cluster of trigger events occur at the same time of a sensed bladder contraction, this association may indicate that the urge perceived by patient 14 was real as opposed to a phantom sensation disconnected from any bladder activity. In another example, sensed data indicating that bladder 12 included a large volume of urine when a trigger event occurred may suggest that the trigger event was initiated due to an urge incontinence situation instead of just an urgency situation for patient 14. The user may thus review all of the trigger events and clusters associated with sensed physiological data to reconstruct, understand, and evaluate condition of patient 14. Adjustments to therapy may then be customized to according to more detailed information.

In other examples, this sensed data may be used to calibrate the perceptions of patient 14 to actual physiological conditions. If the sensed data indicates that bladder 12 is relatively empty when patient 14 perceives that incontinence is imminent, a clinician may adjust therapy appropriately. If the sensed data indicates that bladder 12 is full when patient 14 perceives that incontinence is imminent, then the clinician or system 10 may confirm that patient initiated trigger events generally correlate to actual imminent voiding episode.

Figure 19A:
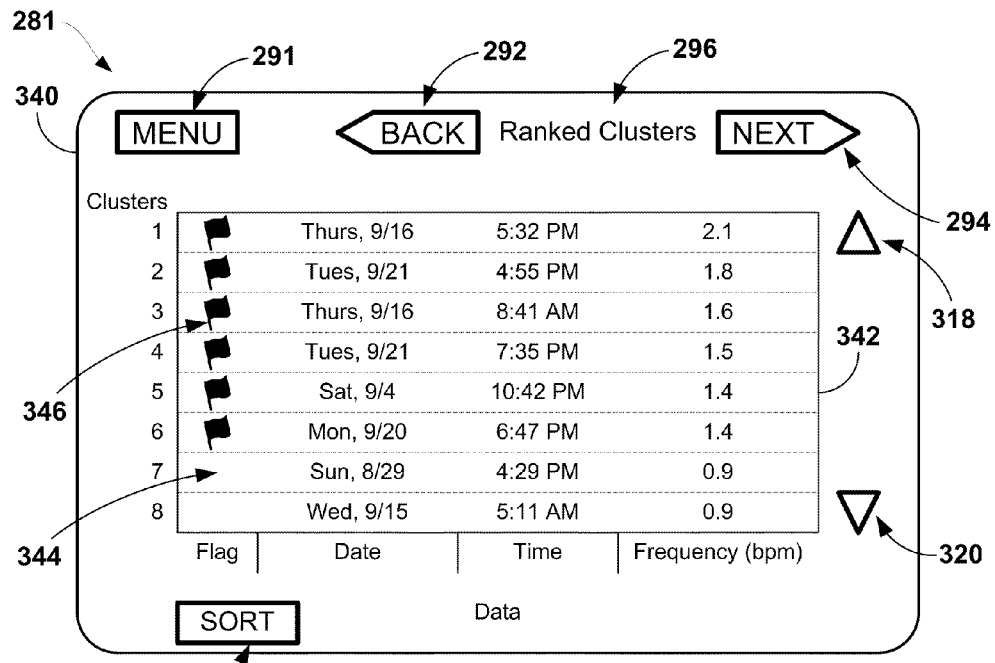
FIGS. 19A and 19B illustrate example user interfaces that display objective incontinence information ranked according to trigger event frequency or number of trigger event clusters.
Figure 19B:
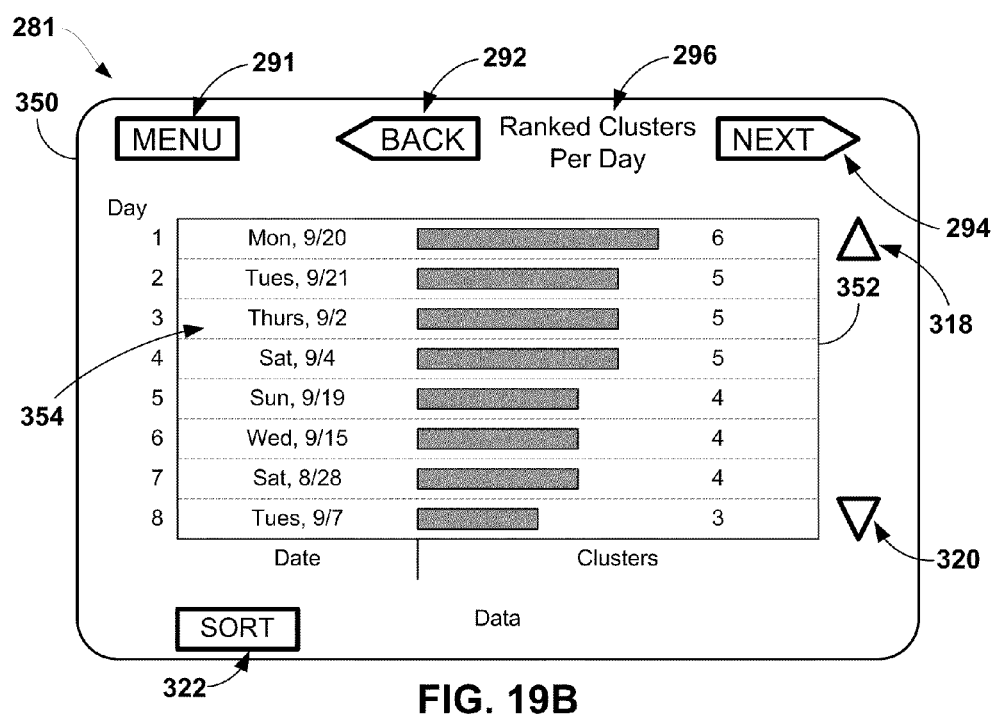

FIGS. 19A and 19B illustrate example user interface 281 presenting ranked clusters as the objective incontinence information. In the example of FIG. 19A, user interface 281 that presents screen 340 with objective incontinence information as clusters of trigger events ranked according to the frequency of trigger events within each cluster. Screen 330 is similar to screen 314 of FIG. 18A, as screen 340 also includes menu input 291, back button 292, next button 294, sort button 322, and scroll arrows 318 and 320. However, screen 340 differs from screen 314 of FIG. 18A in that screen 340 ranks the clusters of trigger events according to the frequency of trigger events (i.e., boosts) occurring within each cluster. Screen title 296 accordingly labels screen 340 for the user as "Ranked Clusters." Frequency of trigger events for a particular cluster may be indicative of the efficacy of the first stimulation therapy. Thus, the objective incontinence information shown in FIG. 19A may be useful for determining when the relatively severe clusters occurred and the therapy program implemented by IMD 16 to generate and deliver the first therapy program when the relatively severe clusters occurred.

Screen 340 includes objective data field 342. Objective data field 342 is similar to objective data field 316 of FIG. 18A, but objective data field 342 displays the clusters as ranked according to frequency of trigger events. Therefore, text entries 344 for each cluster includes the date and time of each cluster, the frequency of trigger events in each cluster, and a flag 346 if the number of trigger events is greater than a predetermined threshold. In the data arrangement shown in FIG. 19A, the clusters with greater frequencies of trigger events are presented at the top of the ranked list with flags 346 indicating the frequency severity.

Screen 340 may rank clusters from any time period. For example, screen 340 may present clusters from a time period of approximately one week. In this manner the time duration may be set to any time period, from as short as a few hours to as long as several months or even years. Although the time period may be set from the current time, the time period may be set with any beginning and end date desired by the user or appropriate for therapy. In other examples, screen 340 may present a predetermined number of clusters, from only a few clusters to several hundred or even thousands. Screen 340 may therefore only present the top 20 ranked clusters, for example. Alternatively, screen 340 may present clusters from a certain therapy period. The therapy period may include, for example, any clusters stored between two clinician visits or two different IMD 16 programming sessions. When viewed by the clinician or patient, screen 340 may therefore present all clusters stored since the last clinician visit or since new therapy programs were provided for use by patient 14. A user may select sort button 322, for example, to modify how the clusters are presented in screen 340.

As shown in the example of FIG. 19B, user interface 281 presents screen 350 with objective incontinence information as each day of therapy ranked based upon how many clusters of trigger events occurred in each day. Screen 350 is similar to screen 314 of FIG. 18A, as screen 350 also includes menu input 291, back button 292, next button 294, sort button 322, and scroll arrows 318 and 320. However, screen 350 differs from screen 314 of FIG. 18A in that screen 350 ranks each day of therapy by the number of clusters of trigger events that occurred during each day. Screen title 296 accordingly labels screen 350 for the user as "Ranked Clusters Per Day." Since each cluster may be indicative of an imminent voiding event in which the first stimulation therapy was not effective at preventing the occurrence of the imminent voiding event or at least the perception of an imminent voiding event by patient 14, identifying days with higher number of clusters may indicate days on which the first stimulation therapy was ineffective or at least less effective for patient 14. Although a day may be generally defined as a calendar day 24-hour period, a day may also be defined as an awake period or other time period by the user.

Screen 350 includes objective data field 352. Objective data field 352 is similar to objective data field 316 of FIG. 18A, but objective data field 352 displays an entry 354 for each day of the displayed time period with the number of clusters for each day. As shown in the example of FIG. 19B, the clusters for each day is displayed graphically and numerically, with a bar graph providing a visual indicator of the number of clusters and a number specifying the exact number of recorded clusters for each day. The bar graph helps the user compare, in a relatively quick manner, the days displayed in screen 350 based on the number of clusters associated with each day. Each entry 354 is ranked by the number of clusters, and in the example shown in FIG. 19B, the day of Monday, September 20 is listed at the top with six clusters during this day, which is the most number of clusters per day for the days shown in FIG. 19B. In FIG. 19B, screen 350 provides days ranked according to the number of clusters, the user may select sort button 322 to sort entries 354 according to criteria other than clusters, e.g., chronologically by days.

Screen 350 may rank days from any time period selected by a user or preprogrammed into objectification module 75 (e.g., prior to generation of any cluster data). For example, screen 350 may present each day from a time period of approximately one week. In this manner the time duration may be set to any time period, from as short as a few days to as long as several months or even years. Although the time period may be set from the current time to older days, the time period may be set with any beginning and end date desired by the user or appropriate for review/therapy. In other examples, screen 350 may present a predetermined number of days, from only a few days to several hundred days. Screen 350 may therefore only present the 20 days with the most number of clusters, for example. Alternatively, screen 350 may present the days occurring within a certain therapy period. The therapy period may include any days between two clinician visits or two different programming sessions. When viewed by the clinician or patient, screen 350 may therefore present all days stored since the last clinician visit or since new therapy programs were provided for use by patient 14.

Figure 20A:
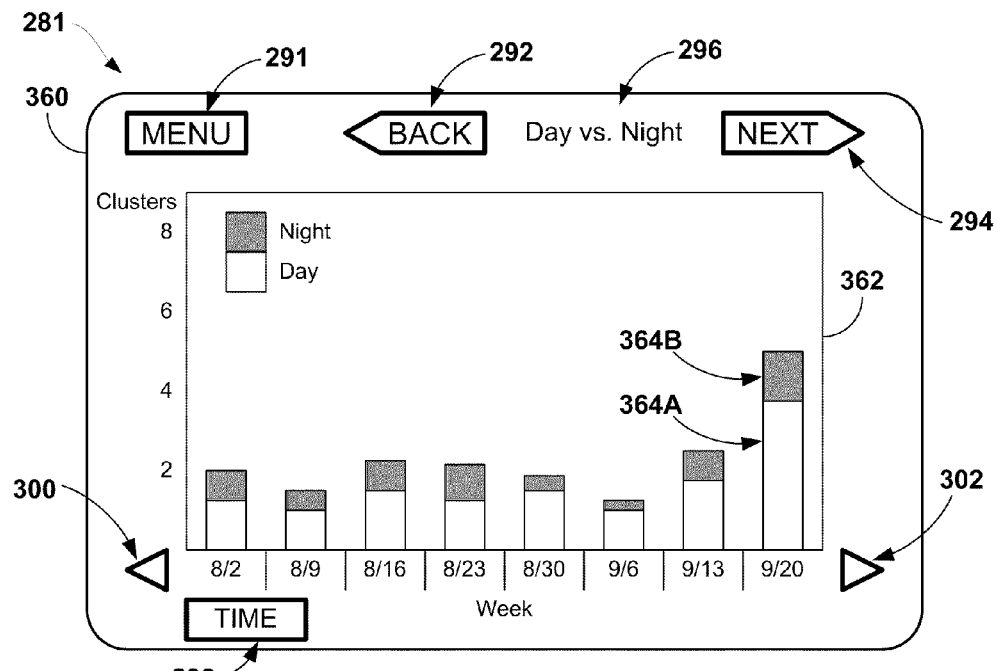
FIGS. 20A and 20B illustrate example user interfaces that display objective incontinence information associated with time of day and type of activity, respectively.
Figure 20B:
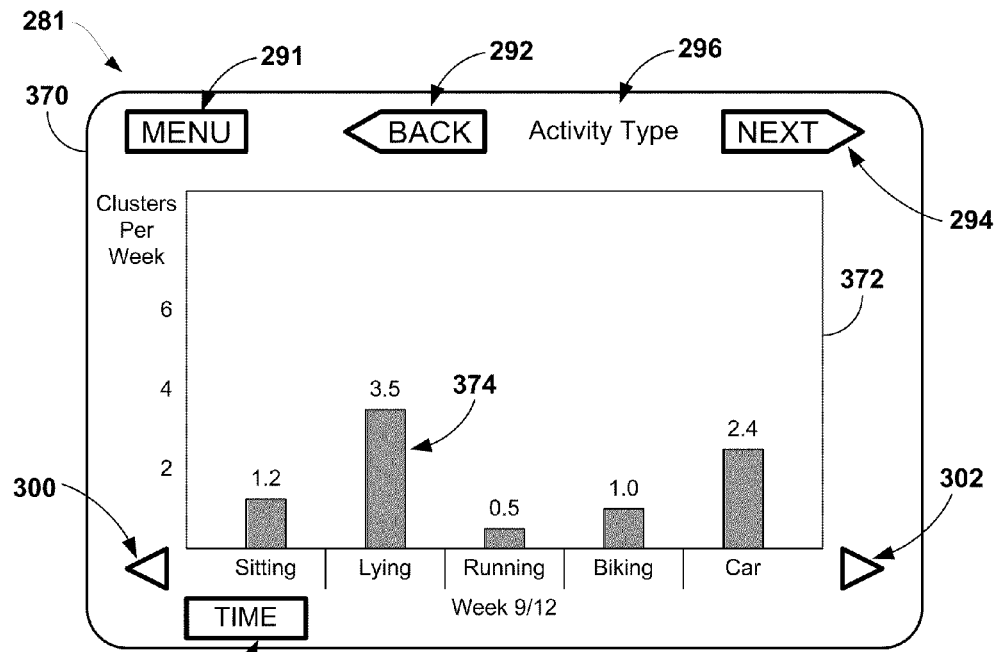

FIGS. 20A and 20B illustrate example user interface 281 that displays objective incontinence information associated with a certain time of day or type of activity. The example of FIG. 20A illustrates example user interface 281 presenting screen 360 that provides the average number of clusters each week separated by day and night. Screen 360 of FIG. 20A is similar to screen 290 of FIG. 17A, as screen 360 also includes menu input 291, back button 292, next button 294, time input 298, and scroll arrows 300 and 302. Screen 360 of user interface 281 generally presents objective incontinence information in the form of an average cluster interval for each time period. Screen title 296 reflects this information as indicated in "Day vs. Night."

A classification of a cluster event as occurring during the day or at night may be useful for, for example, evaluating the patient condition (e.g., whether the severity of the patient incontinence increases or improves at night) and/or efficacy of therapy system (e.g., whether the therapy remains effective during the day or at night, or changes). One symptom of urinary incontinence is nocturia, which includes a need or urge to void during a sleep event. Nocturia may also be a symptom of other problems, such as interstitial cystitis, diabetes, benign prostatic hyperplasia or prostate cancer, and, therefore, may be revealing of an underlying patient condition or a co-morbidity. Detecting when patient 14 has nocturia, e.g., based on the number of clusters of trigger events occurring at night, may be useful for diagnosing patient 14 and configuring therapy system 10 to better address the nocturia.

In the example of FIG. 20A, objective data field 362 includes day bars 364A and night bars 364B that graphically indicate the average number of clusters per day within each specified week within objective data field 362. When shown together, bars 364A and 364B indicate the total average number of clusters per day for each week. In other examples, a numerical value for each of day bars 364A and 364B may also be provided within or above each of day bars 364A and 364B. Alternatively, the average of the total number of clusters per day in each week may be provided above bars 364A and 364B. In this manner, objective data field 362 may provide trend information about the efficacy of stimulation therapy at night and during the day.

In other examples, objective data field 362 may provide day and night objective incontinence information in other forms. For example, screen 360 may present clusters per day separated between day and night, clusters per month between day and night, or the total number of day and night clusters over one or more time periods (days, weeks, or months). The user may also select the change the time period used to present the average number of clusters using time input 298. The user may also select how day and night clusters are determined. For example, system 10 may differentiate between day and night clusters by time of day, where the time ranges characterized as "day" and "night" can be predetermined and selected by a user or by the distributor of therapy system 10 or programmer 24. Additionally or alternatively, system 10 may use one or more sensors or input from patient 14 to indicate if the cluster should be classified as a night or day cluster. For example, system 10 may consider "night" to coincide when a sleep state of patient 14 (e.g., when patient is sleeping or attempting to sleep) and "day" to be when patient 14 is not in a sleep state.

Processor 70 of programmer 24 may identify when patient 14 is attempting to sleep in a variety of ways. For example, processor 70 may identify the time that patient begins attempting to fall asleep based on an indication received from a patient 14 via user interface 74 (FIG. 4) of programmer 24. As another example, processor 70 detects the sleep state of patient 14 by identifying the time that a patient 14 begins attempting to fall asleep based on the activity level of patient 14, which can be monitored sensor 22. A relatively low level of activity indicates that patient 14 has likely entered a sleep state. The low level of activity may be cross-checked with the time of day (e.g., if IMD 16 or programmer 24 includes a clock) or the posture of patient 14 in order to confirm that patient 14 is entering a sleep state and not merely inactive. Other techniques may also be used to detect a sleep state of patient 14.

In the example of FIG. 20B user interface 281 presents screen 370 that provides the average number of clusters of trigger events each week categorized by the type of activity when each cluster occurred. Screen 370 of FIG. 20B is similar to screen 290 of FIG. 17A, as screen 370 also includes menu input 291, back button 292, next button 294, time input 298, and scroll arrows 300 and 302. Screen 370 of user interface 281 generally presents objective incontinence information in the form of an average number of trigger event clusters for each activity type over a given time period. Screen title 296 reflects this information as indicated in "Activity Type." Clusters of trigger events may generally indicate an imminent voiding event or at least the perception of an imminent voiding event by patient 14. Thus, viewing clusters associated with the type of activity patient 14 is engaged at the time may indicate the type of incontinence patient 14 that may be the cause of the imminent voiding event.

One form of urinary incontinence, referred to as "stress incontinence," is at least partially attributable to a failure of muscles around the bladder neck and urethra to maintain closure of the urinary outlet. Patients with stress incontinence may experience minor leakage from physical activities that apply pressure to the bladder, such as coughing, sneezing, laughing, exercising or other movements that increase intraabdominal pressure. Thus, cluster events associated with a relatively high activity level (e.g., running or biking) may be indicative of stress incontinence. Another form of urinary incontinence, referred to as "urge incontinence," (also called hyperactive or overactive bladder) involves the involuntary leakage of urine while suddenly feeling the need or urge to urinate. Urge incontinence may be attributable to abnormally heightened commands from the spinal cord to the bladder that produce unanticipated bladder contractions, or from damage to the nerves of the bladder, nervous system or the muscles. Patients with urge incontinence may need to urinate frequently. When the bladder reaches capacity, the nerves appropriately signal the brain that the bladder is full, but the urge to void, cannot be voluntarily suppressed. Cluster events associated with a relatively low activity level (e.g., sitting or lying) may be indicative of urge incontinence.

In addition, viewing the patient activity associated with cluster can also indicate which, if any, patient posture states are associated with higher incidences of urge (or other types of imminent voiding events). For example, a higher number of clusters in the lying position may indicate that the lying position is problematic for patient 14. A clinician may then tailor therapy to treat that specific condition. For example, if IMD 16 is configured to select a therapy program for the first stimulation therapy based on the posture state of patient 14, e.g., determined based on an output from sensor 22, the clinician can select a therapy program with a higher intensity stimulation (e.g., a function of the stimulation parameters, such as amplitude, pulse width, and frequency) for the lying down posture state.

In the example of FIG. 20B, objective data field 372 includes activity bars 374 for each activity type that graphically indicates the average number of clusters per time period. In the example of FIG. 20B, the time period is the specific week of September 12. The user may select time input 298 to change the time period, e.g., day, week, month, therapy period, etc., for which the average number of clusters is calculated in objective data field 372. The user may select scroll button 300 to move backward in time or scroll button 302 to more forward in time. Although the average number of clusters for each activity is shown numerically in addition to graphically for each of activity bars 374, the average number of clusters may only be shown in one format in some examples.

FIG. 20B illustrates an example in which five different types of activities are tracked by system 10. When IMD 16 detects the type of activity within a sensor, e.g., sensor 22 of FIG. 3, processor 50 may associate any trigger events and clusters with that detected activity and store the association in memory 56. Alternatively, user interface 74 of programmer 24 may receive an activity input from patient 14 indicating the type of activity of patient 14 undertakes at a particular time, and processor 50 or 70 may associate any trigger events with the indicated type of activity. The types of activities detected and presented in FIG. 20B include sitting, lying, running, biking, and riding in a car. However, other examples may include fewer or more activities. In addition, certain types of activities may be further segmented according to the intensity of the activity or position during the activity. For example, the lying activity may be segmented into lying on the left side, lying on the right side, lying face down, and lying face up. In some examples, the user may select the type of activities to view in screen 370 or even view the clusters per activity types for multiple time periods at once.

Figure 21A:
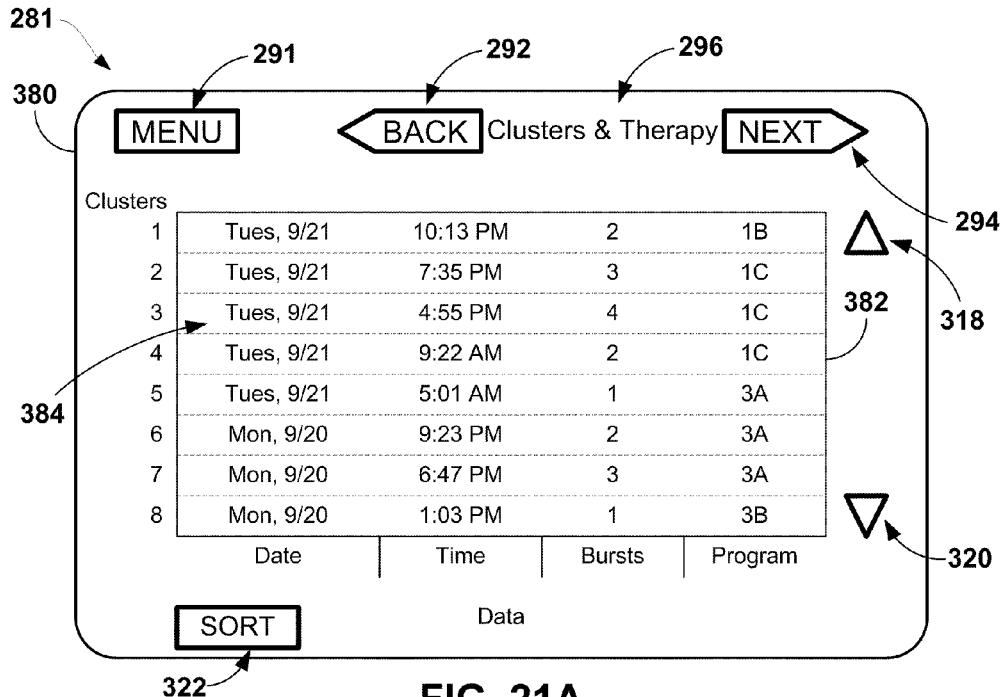
FIGS. 21A and 21B illustrate example user interfaces that display objective incontinence information as therapy programs associated with trigger events.
Figure 21B:
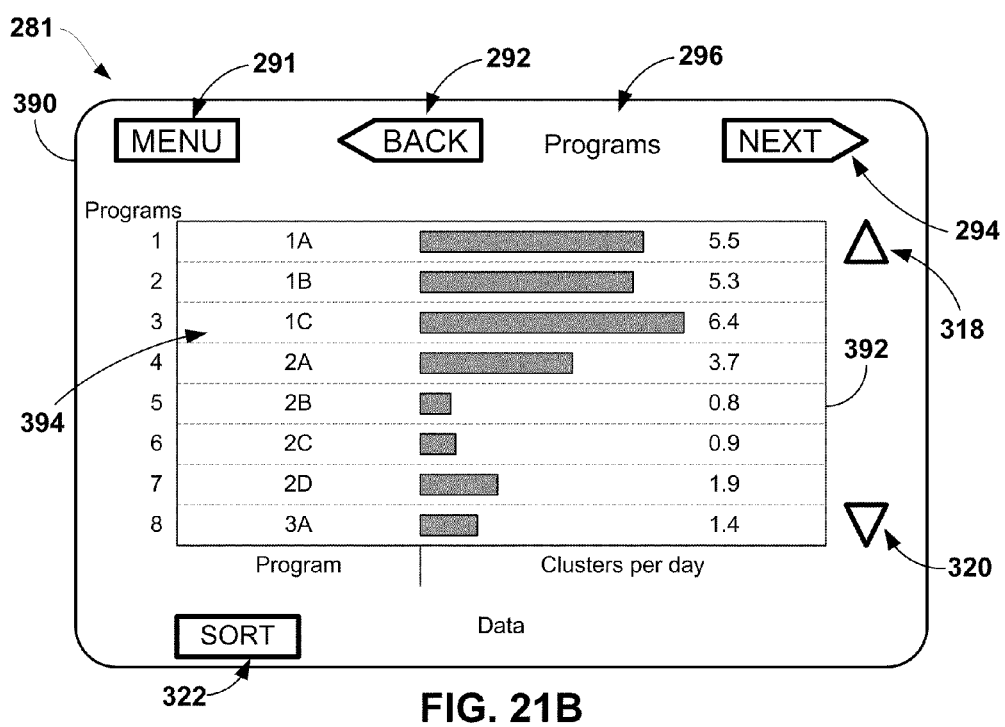

FIGS. 21A and 21B illustrate example user interface 281 that displays objective incontinence information with therapy programs defining stimulation therapy when trigger events occur. In the example of FIG. 21A, user interface 281 presents screen 380 with objective incontinence information as clusters of trigger events associated with the therapy program defining the first stimulation therapy when the trigger events were received. Screen 380 is similar to screen 314 of FIG. 18A, as screen 380 also includes menu input 291, back button 292, next button 294, sort button 322, and scroll arrows 318 and 320. However, screen 380 differs from screen 314 of FIG. 18A in that screen 380 presents the objective incontinence information of trigger event clusters associated with therapy programs. Screen title 296 accordingly labels screen 380 for the user as "Clusters & Therapy." Screen 380 provides information with which a user may view the therapy programs that were implemented by IMD 16 to generate and deliver the first stimulation therapy and the associated number of clusters, which are indicative of imminent voiding events that occurred despite the delivery of the first stimulation therapy. In this way, screen 380 provides information with which a user may relatively quickly compare the efficacy of a plurality of therapy programs based on data specific to patient 14.

Screen 380 includes objective data field 382. Objective data field 382 displays data for each cluster of trigger events. Each text entry 384 of each cluster includes the date and time of each cluster, the number of trigger events ("bursts") in the cluster, and an identification (e.g., a name or other alphanumeric identifier) of the therapy program used to deliver the base stimulation therapy at that time. This associated therapy program defines the parameters for stimulation therapy and may be chosen by the clinician or patient 14. By selecting sort button 322, the user may sort the text entries 384 by date, time, number of bursts (i.e., trigger events), or even program. The user may also user scroll arrows 318 and 320 to move through all of the clusters being presented.

Screen 380 may rank present clusters from any time period appropriate for therapy. For example, screen 380 may present clusters from a time period of approximately one week. In this manner the time duration may be set to any time period, from as short as a few hours to as long as several months or even years. Although the time period may be set from the current time, the time period may be set with any beginning and end date desired by the user or appropriate for therapy. In other examples, screen 380 may present a predetermined number of clusters, from only a few clusters to several hundred or even thousands. Alternatively, screen 380 may present clusters from a certain therapy period. The therapy period may include any clusters stored between two clinician visits or two different programming sessions. When viewed by the clinician or patient, screen 380 may therefore present all clusters stored since the last clinician visit or since new therapy programs were provided for use by patient 14. A user may select sort button 322, for example, to modify how the clusters are presented in screen 380.

As shown in the example of FIG. 21B, user interface 281 presents screen 390 with objective incontinence information as the average number of clusters per day for each therapy program delivering the first stimulation therapy. Screen 390 is similar to screen 380 of FIG. 21A, as screen 390 also includes menu input 291, back button 292, next button 294, sort button 322, and scroll arrows 318 and 320. However, screen 390 differs from screen 380 of FIG. 21A in that screen 390 organizes the objective incontinence information by therapy program instead of by cluster. Screen title 296 accordingly labels screen 390 for the user as "Programs." Identifying therapy programs associated with more clusters (and the second stimulation therapy for boost) based on screen 390 may help the clinician evaluate the efficacy of the first stimulation therapy delivered by IMD 16, and, if desired, adjust one or more parameter values of the stimulation therapy.

Screen 390 includes objective data field 392. Objective data field 392 is similar to objective data field 380 of FIG. 21A, but objective data field 392 displays an entry 394 for each therapy program used by patient 14. As shown in the example of FIG. 21B, the entry 394 for each program includes the average number of clusters per day displayed graphically and numerically, with a bar graph providing a visual indicator of the average number of clusters and a number specifying the number of average clusters for each day. The user may use sort button 322 to sort entries 394 by therapy program or by the average number of clusters per day. In this way, the user may relatively quickly ascertain the therapy programs associated with the highest number of clusters of trigger events. Although screen 390 provides the average number of clusters per day, the user may select the number of clusters averaged over any time period, e.g., hours, days, weeks, months, or even one or more therapy period. Screen 390 may present objective incontinence information for any suitable therapy programs, such as all therapy programs in memory, only those therapy programs currently authorized for use by patient 14 or therapy programs implemented by IMD 16 in a particular range of time.

Figure 22:
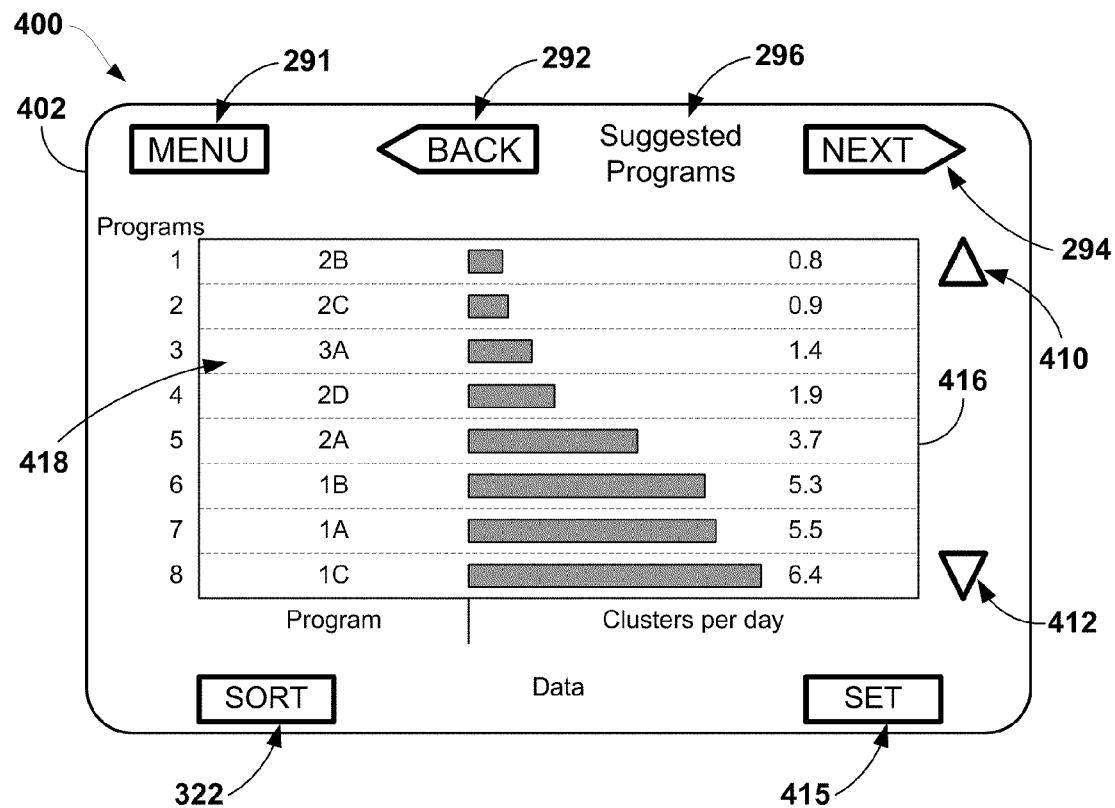
FIG. 22 illustrates an example user interface that provides suggested therapy programs based upon the number of associated trigger events.

FIG. 22 illustrates example user interface 400 that displays screen 402, which provides suggested therapy programs based upon the number of associated trigger events, or clusters, for each therapy program. As shown in the example of FIG. 22, the objective incontinence information displayed within screen 402 includes the average number of clusters per day for each therapy program delivering the base stimulation therapy, i.e., the first stimulation therapy. Therapy programs are ranked in screen 402. In addition, screen 402 displays a suggestion for one or more future therapy programs for patient 14 based upon the least amount of clusters per program. In some examples, processor 70 of programmer 70, objectification module 75, or another processor generates the therapy program suggestion by selecting the therapy programs associated with the lowest number of clusters. Other factors can also be considered, such as power usage and/or stimulation-induced side effects associated with the therapy program.

Screen 402 is similar to screen 390 of FIG. 21B, as screen 402 also includes menu input 291, back button 292, next button 294, sort button 322, and scroll arrows 318 and 320 However, screen 402 differs from screen 390 of FIG. 21B in that screen 402 ranks each therapy program according to the minimal number of clusters observed per day. In other words, fewer associated clusters put a therapy program at the top of the ranking Screen title 296 accordingly labels screen 402 for the user as "Suggested Programs." The number of clusters of trigger events associated with a therapy program indicate the number of boosts needed to supplement the first stimulation therapy. User interface 400 suggests therapy programs with fewest cluster associations for use defining parameters of future first stimulation therapy.

Screen 402 includes objective data field 416. Objective data field 416 is similar to objective data field 390 of FIG. 21B in that objective data field 416 displays an entry 418 for each therapy program used by patient 14. The entry 418 for each therapy program includes the average number of clusters per day displayed graphically and numerically, with a bar graph providing a visual indicator of the average number of clusters associated with the respective therapy program each day and a number specifying the number of average clusters associated with the respective therapy program for each day the therapy program was used, for each day in a time range specified by a user or for another time range. The user may use sort button 322 to sort entries 418 by program instead of clusters per day in other examples. Although screen 402 provides the average number of clusters per day as an indication of therapy efficacy, the user may select the number of clusters averaged over any time period, e.g., hours, days, weeks, months, or even one or more therapy period. Screen 402 may present all therapy programs in memory or only those therapy programs currently authorized for use by patient 14.

Based upon viewing the therapy programs presented in screen 402, the user may select one of the therapy programs by highlighting the desired entry 418 and selecting set button 415. If no entry 418 is highlighted, processor 70 of programmer 24 (or another device in other examples) may automatically set the current therapy program for the first stimulation therapy to the program with the fewest clusters when set button 415 is selected, which is program "2B" in the example shown in FIG. 22. In other examples, screen 402 may only present only those therapy programs with a cluster per day average below a therapeutic threshold, which can be selected by a user or predetermined by a distributor of programmer 24. Alternatively, screen 402 may only present the therapy program with the least number of clusters per day unless the user requests other therapy programs. Therefore, any use of objective incontinence information associated to therapy program use may be used to aid the user, e.g., clinician or patient 14, in selecting an efficacious program for therapy.

In other examples, screen 402 may provide additional information to aid in the selection of a therapy program for future stimulation therapy. For example, screen 402 may provide a list of known side effects to the use of each therapy program, the power required to deliver each therapy, the amount of time each therapy program has been used to deliver the first stimulation therapy, or any other metric of program use. In this manner, the user may review several pieces of information in addition to the number of clusters when choosing a therapy program for further treatment.

Figure 23:
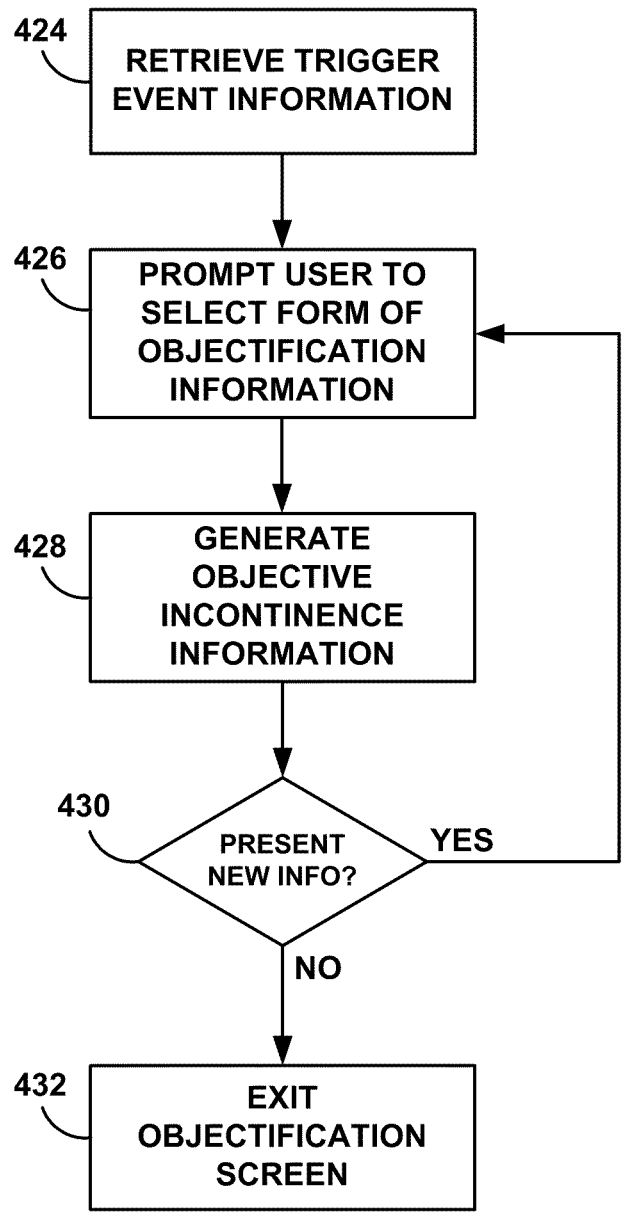
FIG. 23 is a flow diagram illustrating an example technique of presenting objective incontinence information to a user.

FIG. 23 is a flow diagram illustrating an example technique of presenting objective incontinence information to a user. The technique shown in FIG. 23, as well as the other figures herein, can be implemented by objectification module 75 and/or processor 70 of programmer 24 or any suitable computing device. Thus, while FIG. 23 is described with respect to objectification module 75, in other examples, the technique shown in FIG. 23 may be performed by processor 70 of programmer 24 or a processor another suitable device. The technique of FIG. 23 may be initiated during therapy delivery, during patient 14 monitoring, or during system idle (e.g., when IMD 16 is not delivering therapy to patient 14 or monitoring a patient parameter). For example, this technique may be initiated after user interface 74 of programmer 24 receives an objective data input requesting objective incontinence information. Processor 70 of programmer 24 may then retrieve trigger event information from memory 56 of IMD 16 and/or memory 72 of programmer 24 (424). Processor 70 can, for example, communicate with IMD 16 via the respective telemetry modules 76, 58 and interrogate IMD 16 to retrieve trigger event information (or "data"), such as information that indicates the occurrence of trigger events (e.g., patient input or based on sensed physiological parameters). In other examples, IMD 16 may periodically transmit the trigger event information to processor 70 of programmer 24.

Objectification module 75 controls user interface 74 to prompt the user to select the form (or format) of the objective incontinence information to be presented (426). An example prompt for user selection is screen 282 of FIG. 15. Based upon the form of the objective incontinence information selected by the user, objectification module 75 generates the objective incontinence information to be presented to the user via a display of user interface 74 of programmer (428). This generated information may result in screens such as those examples of FIGS. 17-22. If objectification module 75 receives, via user interface 74, a request to present new objective incontinence information or a new form of the information ("YES" branch of block 430), then objectification module 75 may control user interface 74 to prompt the user to indicate the format in which the user would like to view the new information (426). If the user does not wish to view other objective incontinence information by requesting to exit the objectification screens ("NO" branch of block 430), objectification module 75 may control user interface 74 to exit the objectification screens (432). If no request for a new form of objective incontinence information or to exit the screen is received, user interface 74 may continue to present the information to the user. Of course, IMD 16 may continue to deliver therapy to patient 14 while a user is reviewing objective incontinence information.

Figure 24:
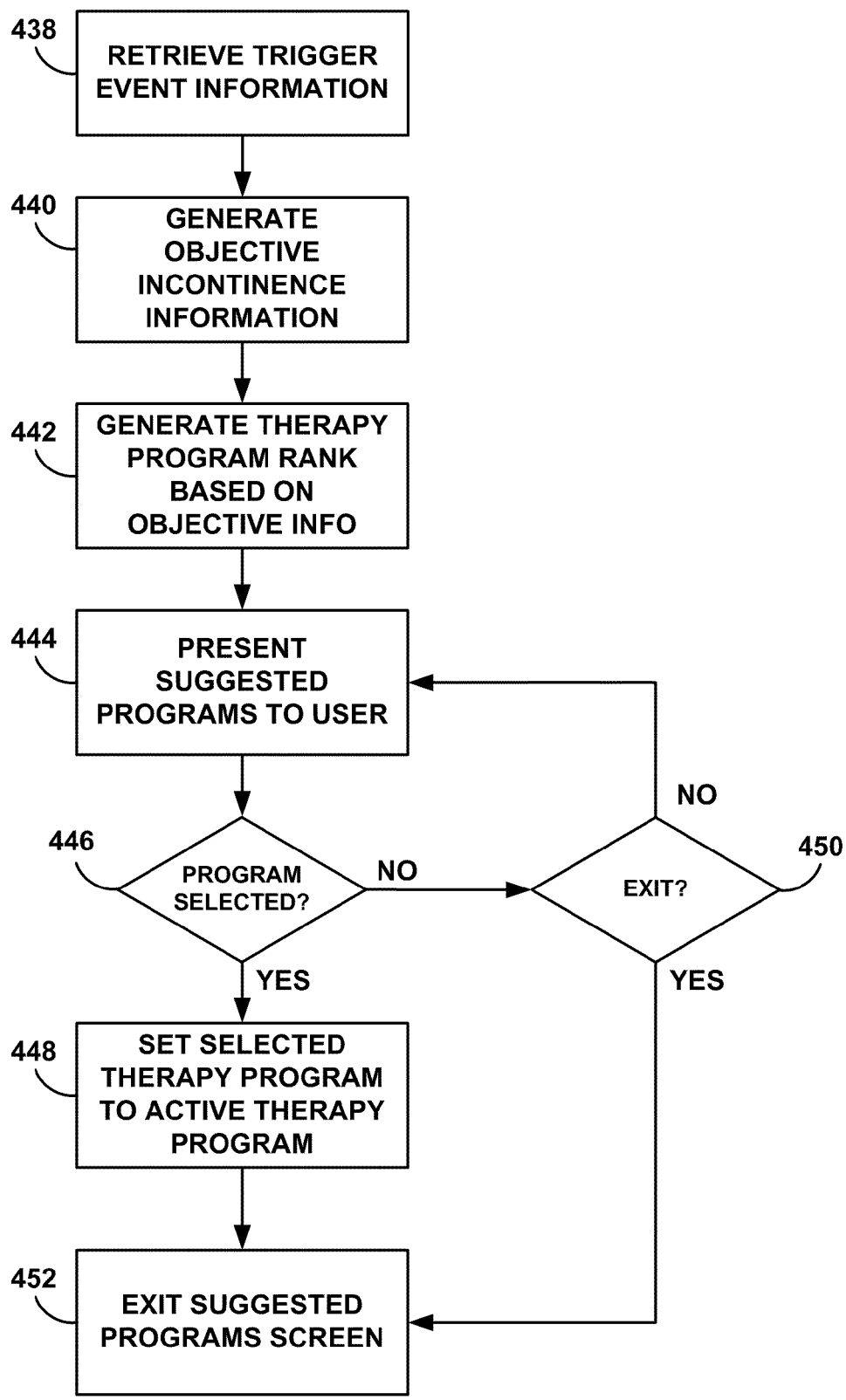
FIG. 24 is a flow diagram illustrating an example technique of presenting suggested therapy programs to a user based upon objective incontinence information.

FIG. 24 is a flow diagram illustrating an example technique of presenting suggested therapy programs to a user based upon objective incontinence information. As with FIG. 23, the technique shown in FIG. 24 can be implemented by objectification module 75 and/or processor 70 of programmer 24 or any suitable computing device. Thus, while FIG. 24 is described with respect to processor 70, in other examples, the technique shown in FIG. 24 may be performed by objectification module 75 of programmer 24 or a processor another suitable device. In addition, the technique shown in FIG. 24 may be executed during therapy delivery by IMD 16 using the first stimulation therapy and second stimulation therapy, or boost, when needed, although the technique shown in FIG. 24 may also be implement at other times, e.g., after trial stimulation therapy to generate the trigger event data and before implementation of chronic therapy delivery.

Processor 70 of programmer 24 retrieves trigger event information from memory 56 of IMD 16 and/or memory 72 of programmer 24 to begin the technique of presenting suggested therapy programs to the user (438). Processor 70 then generates the objective incontinence information, which is used to generate a suggestion (or recommendation) of one or more therapy programs to the user for use in subsequent therapy (440). Processor 70 then generates a therapy program rank based upon the generated objective incontinence information (442). For example, processor 70 may rank the therapy programs based on the lowest frequency of clusters or the lowest number of clusters associated with each therapy program. In other words, the highest ranked therapy program may be the program requiring minimal trigger events during use. Processor 70 may generate a program suggestion that indicates that the most highly ranked one or more therapy programs (but less than the entire list of therapy programs) be used for subsequent delivery of the first stimulation therapy to patient 14. Processor 70 may control user interface 74 to presents, e.g., via a display, the one or more suggested therapy programs to the user for selection by the user (444). This presented information may be similar to that described in screen 402 of FIG. 22. User interface 74 may also adjust the presented suggested therapy programs upon receiving user input requesting such information.

If processor 70 does not receive user input selecting a suggested program ("NO" branch of block 446), processor 70 may check to see if the user has requested to exit the suggested program screen (450). If the user has not requested to exit the suggested program screen ("NO" branch of block 450), then processor 70 continues to display, via user interface 74, the suggested programs to the user (444). If processor 70 receives user input requesting to exit ("YES" branch of block 450), processor 70 controls user interface 74 to exit to a previous menu or otherwise leave the currently displayed screen (452). If processor 70 receives user input selecting one of the suggested therapy programs presented via user interface 74 ("YES" branch of block 446), processor 70 may set the selected therapy program as the active therapy program that defines the first stimulation therapy, i.e., the base therapy (448). User interface 74 then exits the suggested programs screen (452). In some examples, processor 70 transmits the selected therapy program or an indication of the selected therapy program (if IMD 16 stores therapy program settings) to IMD 16 via the respective telemetry modules 76 and 58. IMD 16 may then generate and deliver the first stimulation therapy in accordance with the selected therapy program.

In some examples, user interface 74 may present only one suggest program to the user for confirmation. Upon confirmation of the suggested therapy program, processor 70 may set the new program as the active therapy program. In addition or in other examples, user interface 74 may present another therapy program, e.g., the next highest ranked therapy program, if the user does not select the suggested therapy program or actively declines the suggested therapy program. Although programmer 24 may present suggested therapy programs when requested by the user, programmer 24 may also prompt patient 14 to select a new therapy program after a predetermined period of time. For example, a clinician may require patient 14 to review used therapy programs on a periodic basis in order for patient 14 to update the active therapy program and use the most efficacious program.

In some examples, the technique of FIG. 24, e.g., the new programming of therapy using suggested programs, may be initiated by a request from a user using programmer 24. For example, this new program request may be provided by a clinician during a clinic visit. Alternatively, processor 50 may determine that new programming should occur based on one or more of several techniques. In one example, processor 50 may follow a schedule stored within memory 52 to periodically search for the relatively most effective stimulation parameters and programs. In another example, processor 50 may monitor the number or frequency of boost usage to prompt reprogramming when boost usage indicates ineffective therapy by the first stimulation therapy program. Processor 50 may apply a predetermined boost number or frequency threshold to identify when programming should be initiated.

Figure 25:
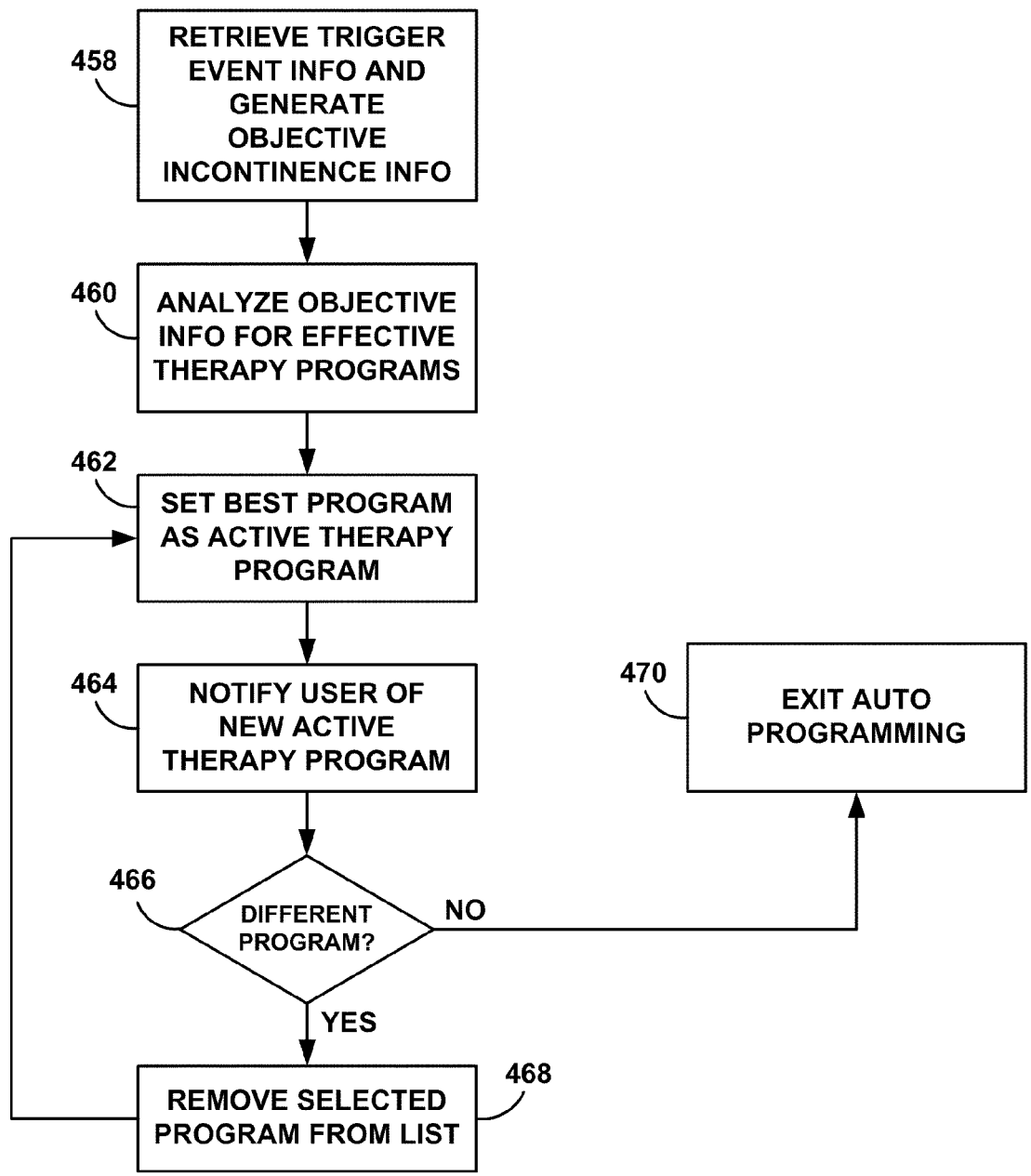
FIG. 25 is a flow diagram illustrating an example technique of automatically selecting a therapy program based upon objective incontinence information.

FIG. 25 is a flow diagram illustrating an example technique of automatically selecting a therapy program based upon objective incontinence information. The technique of FIG. 25 is similar to that of FIG. 24, but processor 70 of programmer 24 automatically selects a new therapy program based upon objective incontinence information. As shown in FIG. 25, processor 50 of IMD 16 retrieves trigger event information from memory 56 of IMD 16 and/or memory 72 of programmer 24 and generates objective incontinence information needed to suggest a therapy program (458). Although processor 50 is described as performing this technique, processor 70 of programmer 24 or another external computing device may perform all or part of the technique shown in FIG. 25.

Processor 50 then analyzes the objective incontinence information to determine the relatively most effective therapy programs based upon the information (460). For example, the programs with the fewest associated clusters per day may be identified as effective. Processor 50 sets the most effective therapy program, e.g., the therapy program associated with the fewest number of trigger events (i.e., boosts) or clusters of trigger events, as the active therapy program for subsequent therapy delivery according to the first stimulation therapy (462). In some examples, user interface 74 of programmer 24 may notify the user of the newly selected active therapy program (464). In some examples, processor 70 of programmer 24 provides the user with the option to select a therapy program other than the one automatically selected by processor 50 to control the delivery of the first stimulation therapy. For example, processor 70 may control user interface 74 to display a user interface screen with which the user may interact to indicate whether the selected therapy program is accepted or declined. If the user accepts the selected therapy program or otherwise does not desire a different program ("NO" branch of block 466), then user interface 74 may exit, e.g., to a previous menu (470), and IMD 16 delivers the first stimulation therapy with the new active therapy program (454).

If the user indicates a different program is desirable, e.g., by requesting a new program from user interface 74 ("YES" branch of block 466), then processor 50 may remove the previously selected therapy program from the list of suggested therapy programs (468). Processor 50 may continue setting the next best therapy program of the suggested therapy programs as the active therapy program (462) until the user is satisfied, e.g., accepts the therapy program selected by processor 50. In other examples, processor 50 may transmit control signals that cause user interface 74 of programmer 24 to present the list of suggested therapy programs for selection by the user upon the first program rejection by the user. In any case, system 10 may user objective incontinence information collected from the trigger events to automatically select new effective therapy programs.

In some examples, processor 50 may also monitor the number or frequency of trigger events, e.g., boost usage, after processor 50 selects and implements the new active therapy program. If processor 50 identifies fewer trigger events, then processor 50 may confirm the new therapy program. If the number or frequency of trigger events does not decrease, then processor 50 may again prompt the technique of FIG. 14 to find a new program that may be more effective for patient 14.

As described herein, automatic programming by processor 50 may be initiated by a request from the user using programmer 24 or another computing device. Alternatively, processor 50 may determine that new programming should occur based on several techniques. In one example, processor 50 may follow a schedule stored within memory 52 to periodically search for the relatively most effective stimulation parameters and programs. In another example, processor 50 may monitor the number or frequency of boost usage to prompt autoprogramming when boost usage indicates ineffective therapy by the first stimulation therapy program. Processor 50 may apply a predetermined boost number or frequency threshold to identify when programming should be initiated.

Figure 26:
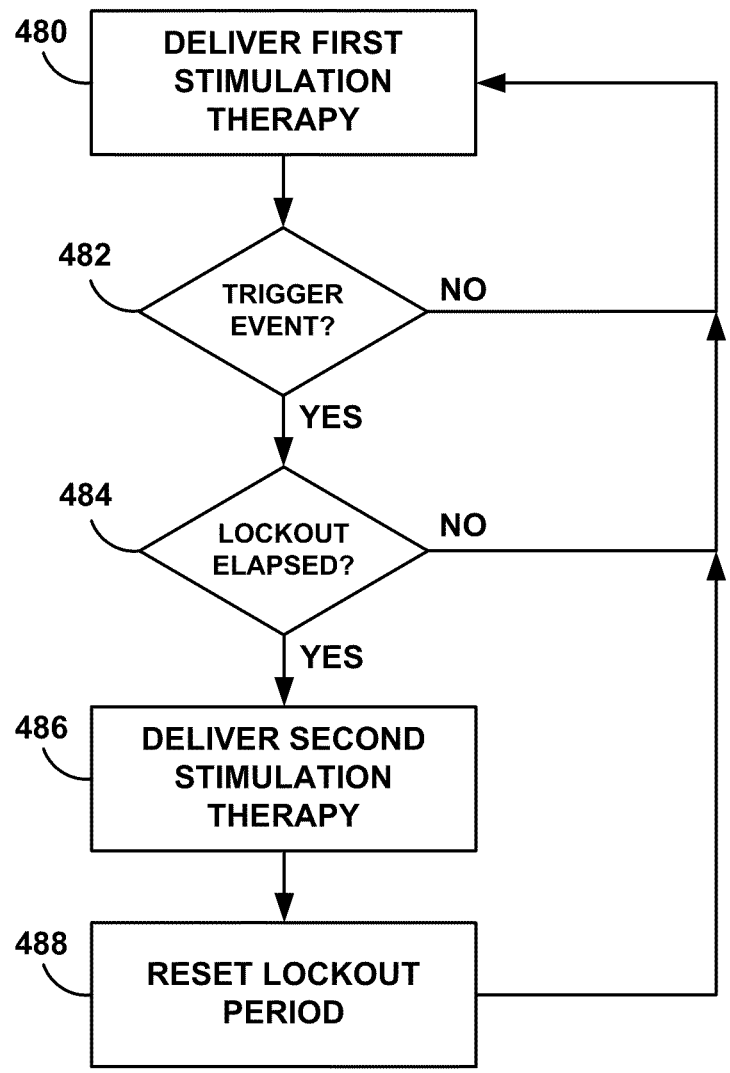
FIG. 26 is a flow diagram illustrating an example technique of withholding the second stimulation therapy until a lockout period has elapsed.

FIG. 26 is a flow diagram illustrating an example technique of withholding the second stimulation therapy until a lockout period has elapsed. The technique shown in FIG. 26 may be implemented by processor 50 of IMD 16, processor 70 of programmer 24, or any other suitable computing device used to implement the trigger event detection and/or initiation of the second stimulation therapy. Thus, while FIG. 26 is described with respect to processor 50, in other examples, the technique shown in FIG. 26 may be performed by processor 70 of programmer 24 or a processor another suitable device.

As shown in FIG. 26, processor 50 controls therapy delivery module 52 of IMD 16 to deliver the first stimulation therapy to patient 14 (480). In some examples, IMD 16 initiates the delivery of the first stimulation therapy upon activation of chronic therapy delivery by the clinician. IMD 16 delivers the first stimulation therapy chronically, e.g., periodically for an extended period of time, such as hours, days, weeks, or, in examples in which the first and second stimulation therapies are not delivered simultaneously, until an event occurs that triggers delivery of the second stimulation therapy.

IMD 16 also monitors a patient condition via a sensor or receives a patient input to determine whether a trigger event is detected (482). Example trigger events may be detected include, but are not limited to, bladder contraction exceeding (e.g., greater than or equal to) a threshold level, abnormal detrusor muscle activities (e.g., as indicated by an EMG) patient activity level exceeding a threshold level, patient posture state, and patient input requesting a boost in therapy to avoid voiding. As previously described, IMD 16 may monitor bladder impedance, bladder pressure, pudendal or sacral afferent nerve signals, a urinary sphincter EMG, or any combination thereof to detect changes in bladder contraction.

The steps of delivering the first stimulation therapy and monitoring the patient to detect a trigger event are illustrated in FIG. 26 as being sequential, but it should be understood that these steps may be performed simultaneously. As an example, IMD 16 may deliver the first stimulation therapy to patient 14 for an extended period of time. During the extended period of time, IMD 16 may periodically monitor patient 14 to detect a trigger event. In some examples, IMD 16 may monitor patient 14 following delivery of a train of first stimulation therapy, e.g., in examples in which the first stimulation therapy is defined by a plurality of consecutive trains of stimulation separated by intervals of time. In other examples, IMD 16 may monitor patient 14 more frequently or less frequently. In yet other examples, IMD 16 may monitor patient 14 substantially continuously.

If IMD 16 does not detect a trigger event ("NO" branch of block 482), IMD 16 continues to deliver the first stimulation therapy (480). On the other hand, if IMD 16 detects a trigger event ("YES" branch of block 482), processor 50 determines if the lockout period has elapsed (484). The lockout period may be any time period that limits the delivery of the second stimulation therapy. Over time, patient 14 may become desensitized (or "adapt") to the second stimulation therapy so that the second stimulation therapy is no longer efficacious. Thus, in some cases, it may be beneficial to limit the frequency with which the second stimulation therapy may be delivered in order to conserve the available energy stored by power source 60 of IMD 16 (FIG. 3) to deliver the first stimulation therapy. Therefore, the lockout period may be implemented to only allow delivery of the second stimulation therapy when the lockout period has elapsed.

The lockout period may be initiated or reset after delivery of the second stimulation therapy (e.g., the start of the second stimulation therapy, upon termination of the second stimulation therapy, upon the occurrence of a trigger event or a certain time period following the trigger event), but the lockout period may also be used in response to other delivered therapies or patient conditions. The lockout period may generally be set to a period between approximately 1 minute and 60 minutes. However, lockout periods of shorter or longer durations are also contemplated. In one example, the lockout period may be set to 3 minutes. The lockout period may be set by a clinician or automatically determined based upon the parameters of the second stimulation therapy or the patient 14 condition in other examples.

If the lockout period has not elapsed, e.g., the second stimulation therapy was delivered more recently than the duration of the lockout period ("NO" branch of block 484), then processor 50 may not act on the trigger event (e.g., may not deliver the second stimulation therapy in response to detecting the trigger event) and continue delivering the first stimulation therapy (480). In the example shown in FIG. 26, processor 50 waits until the lockout period has elapsed to then deliver the second stimulation therapy. If the lockout period has elapsed ("YES" branch of block 484), then processor 50 instructs therapy delivery module 52 to deliver the second stimulation therapy to patient 14 (486). The first and second stimulation therapies may be delivered substantially simultaneously or in an alternating manner (e.g., one type of stimulation is delivered at a time). In some examples, however, processor 50 does not deliver the second stimulation therapy automatically upon the elapsing of the lock period. Instead, processor 50 may wait for the next trigger event, at which time processor 50 may determine whether the lockout period has elapsed (484) and deliver the second stimulation therapy to patient 14 if the lockout period has elapsed (486).

After delivering the second stimulation therapy to patient 14, processor 50 resets the lockout period to prevent subsequent delivery of the second stimulation therapy until after the lockout period elapses (488). Processor 50 then continues to deliver the first stimulation therapy (480). The lockout period may be reset immediately upon delivering the second stimulation therapy to patient 14 or after the termination of the delivery of the second stimulation therapy following the trigger event that initiated the delivery of the second stimulation therapy. Other techniques for resetting the lockout period may be used.

In some examples, IMD 16 delivers the second stimulation therapy for a predetermined period of time, e.g., about 10 seconds to about 50 seconds. The duration of the predetermined period of time may be selected such that an imminent involuntary voiding event is suppressed. In other examples, IMD 16 delivers the second stimulation therapy for a period of time controlled by patient 14. For example, patient 14 may control the duration of the second stimulation therapy by interacting with programmer 24, e.g., by pressing a "boost" button on a keypad or a touch screen, or by interacting directly with IMD 16 (e.g., by tapping skin superior to the implanted IMD 16). A maximum therapy period for patient controlled stimulation may be approximately 3 minutes, although other time ranges are contemplated. In some examples, patient 14 may prolong the delivery of the second stimulation therapy as long as patient 14 continues to hold down the "boost" button. However, the duration that the therapy may be prolonged may be limited to avoid overuse of the second stimulation therapy.

In this way, IMD 16 provides responsive stimulation to control urinary incontinence while avoiding overuse of the second stimulation therapy. Delivering the second stimulation therapy upon detection of a trigger event, rather than on a substantially regular basis, may help reduce muscle fatigue by limiting the amount of the second stimulation therapy provided to patient 14. In addition, implementing the second stimulation therapy only when needed and the lockout has elapsed may help conserve power of power source 60 of IMD 16. Therefore, the lockout period may conserve patient 14 response to the second stimulation therapy and conserve power to help increase the useful life of IMD 16.

The techniques described in this disclosure may reduce or substantially eliminate leaking episodes caused by urinary incontinence. That is, by delivering first stimulation therapy to modulate nerve afferent activities to inhibit bladder contraction, or to maintain internal urinary sphincter closure or urethral closure and, when triggered, second stimulation therapy configured to maximize closure of the internal urinary sphincter, external urinary sphincter, and/or the periurethral muscles, improved management of urinary incontinence may be achieved. The techniques described above may also provide advantageous features that allow a patient to control the delivery of the second stimulation therapy. For example, the patient may actively trigger delivery of the second stimulation therapy or may manually abort the second stimulation therapy. The patient may also temporarily inhibit or deactivate the second stimulation therapy when voiding voluntarily.

The techniques described in this disclosure may reduce or substantially eliminate leaking episodes caused by fecal incontinence. In fecal incontinence examples, the IMD may deliver first stimulation therapy to, for example, a sacral nerve to improve internal and/or external anal sphincter muscle tone, and deliver second stimulation therapy to, for example, a sacral nerve, an internal sphincter, or an external sphincter. The first stimulation therapy may help to close or maintain internal sphincter closure or improve internal and/or external anal sphincter muscle tone. The second stimulation therapy may promote contraction of the internal anal sphincter and/or the external anal sphincter.

Similar to the therapy techniques described with respect to urinary incontinence, the first stimulation therapy may be delivered on a regular basis, e.g., to improve muscle tone, and the second stimulation therapy may be viewed as a short term boost to the effectiveness of the first stimulation therapy or to close or promote closure of the internal and/or external anal sphincter. The second stimulation therapy may be delivered in response to detecting a trigger event, such as receiving patient input, detecting a patient parameter indicative of an imminent fecal incontinence event, or detecting a patient parameter indicative of an increased probability of a fecal incontinence event. Example patient parameters may include contraction of the anal sphincter, patient activity level, or patient posture state. The IMD may detect contraction of the anal sphincter using a pressure sensor, an EMG sensor, or any other suitable sensing mechanism.

The techniques described in this disclosure may also enhance continued stimulation therapy by quantifying the use of second stimulation therapy, or boosts, initiated by trigger events. Because trigger events may indicate that the base therapy, or first stimulation therapy, may not effective at controlling imminent voiding events, objective incontinence information generated from the trigger events may help the clinician or patient evaluate the patient condition and/or modify stimulation therapy. In some examples, the system presents the objective incontinence information to a user, and/or the system suggests therapy programs or automatically changes therapy programs based upon the objective incontinence information. In any case, the techniques described herein are generally directed to utilization of past trigger events to improve subsequent stimulation therapy for the patient.

In some examples, the disclosure is directed to a method comprising delivering, with a medical device, first electrical stimulation therapy to a patient to generate a first physiological effect, receiving input from the patient or a sensor while the medical device is delivering the first electrical stimulation therapy, and delivering, with the medical device, second electrical stimulation therapy to the patient based on the input from the patient or the sensor, wherein the delivery of the second electrical stimulation therapy generates a second physiological effect that is different than the first physiological effect, and wherein the first and second electrical stimulation therapies are configured to manage one of urinary incontinence or fecal incontinence.

In some examples of the method, the first physiological effect comprises inhibiting contraction of a bladder of the patient, and the second physiological effect comprises promoting contraction of one or more of a bladder outlet of the patient, an internal urinary sphincter of the patient, an external urinary sphincter of the patient, or periurethral muscles of the patient. In addition, in some examples of the method, the first electrical stimulation therapy is delivered to the patient on a regular basis and the second electrical stimulation therapy is delivered to the patient only when the input from the patient or the sensor is indicative of at least one of an imminent involuntary voiding event or an increased possibility of an occurrence of an involuntary voiding event.

In some examples of the method, delivering the second electrical stimulation therapy comprises delivering a plurality of electrical stimulation signals during a plurality of therapy periods that are separated by a minimum inter-therapy interval to minimize muscle fatigue.

In some examples of the method, delivering the first electrical stimulation therapy comprises delivering the first electrical stimulation therapy to at least one of a pudendal nerve or a sacral nerve, and delivering second electrical stimulation comprises delivering second electrical stimulation to at least one of a hypogastric nerve, the pudendal nerve, the sacral nerve, a dorsal penile nerve, a dorsal clitoral nerve, an external urinary sphincter, or periurethral muscles.

In some examples of the method, delivering the second electrical stimulation therapy comprises delivering the second electrical stimulation therapy for a therapy period of approximately 10 seconds to approximately 50 seconds.

In some examples of the method, the delivering the second electrical stimulation therapy comprises delivering a stimulation signal comprising an amplitude of approximately two to approximately four times rheobase of a target muscle or nerve, a frequency of approximately 15 Hertz to approximately 66 Hertz, and a pulse width of approximately 100 microseconds to approximately 1000 microseconds.

In some examples of the method, delivering the second electrical stimulation therapy comprises delivering the second electrical stimulation therapy according to a first set of stimulation parameters for a period of time and delivering the second electrical stimulation therapy according to a second set of stimulation parameters different that the first set of stimulation parameters for a subsequent period of time. In some examples of the method, the first set of stimulation parameters is configured to activate fast-twitch muscles of the patient, and the second set of stimulation parameters is configured to activate slow-twitch muscles of the patient.

In some examples of the method, delivering second electrical stimulation therapy to the patient based on the input from the patient or the sensor comprises delivering second electrical stimulation therapy for a predetermined period of time based on the patient input.

In some examples of the method, delivering second electrical stimulation therapy to the patient based on the input from the patient or the sensor comprises determining whether the input is indicative of a trigger event for the second stimulation therapy, determining whether a number of trigger events detected within a predetermined interval of time is greater than or equal to a threshold value, and delivering the second electrical stimulation therapy to the patient if the number of trigger events detected within the predetermined interval of time is not greater than or equal to the threshold value. In some examples, the method further comprises generating a patient notification if the number of trigger events detected within the predetermined interval of time is greater than or equal to the threshold value.

In some examples of the method, the input from the sensor is indicative of at least one of bladder contraction or detrusor muscle activity. In some examples, the input from the sensor comprises at least one of a bladder impedance value, a current or voltage amplitude value for a sacral or pudendal afferent nerve signal, or an electromyogram for a muscle in a pelvic region of the patient.

In some examples of the method, the input from the sensor is indicative of patient activity level or patient posture. In addition, in some examples of the method, the input includes sensor input, and the method further comprises determining whether the input is indicative of a trigger event for the second stimulation therapy, generating a patient notification that indicates prospective delivery of the second stimulation therapy if the input is indicative of the trigger event, receiving patient input after generating the patient notification, and suspending the delivery of the second electrical stimulation therapy based on the patient input.

In some examples of the method, delivering the second electrical stimulation therapy to the patient based on the input from the patient or the sensor comprises determining whether a first input is indicative of a trigger event for the second stimulation therapy, delivering the second electrical stimulation therapy to the patient for a first therapy period if the first input is indicative of the trigger event, after the first therapy period, receiving a second input from the patient or the sensor, after the first therapy period, determining whether the second input is indicative of the trigger event, delivering the second electrical stimulation therapy to the patient for a second therapy period if the second input is indicative of the trigger event, and deactivating the second electrical stimulation therapy if the second input is not indicative of the trigger event.

In some examples of the method, delivering the second electrical stimulation therapy to the patient based on the input from the patient or the sensor comprises determining whether the second stimulation therapy was delivered to the patient within an immediately preceding period of time, delivering the second electrical stimulation therapy to the patient if the second stimulation therapy was not delivered to the patient within the immediately preceding period of time, adjusting the second electrical stimulation therapy if the stimulation therapy was delivered to the patient within the immediately preceding period of time, and delivering the adjusted second electrical stimulation therapy to the patient. In some examples, delivering the second electrical stimulation therapy comprises delivering first stimulation pulses for a first period of time and delivering second stimulation signals having a lower frequency than the first stimulation signals for a second period of time, wherein adjusting the second stimulation therapy comprises adjusting the duration of one of the first period of time or the second period of time.

In some examples of the method, delivering the second electrical stimulation therapy to the patient comprises gradually increasing or decreasing a first stimulation parameter value defined by the first electrical stimulation therapy to a second stimulation parameter value defined by the second electrical stimulation therapy according to a predetermined rate of change or over a predetermined duration of time.

In some examples of the method, the first electrical stimulation therapy defines a first value of a first stimulation parameter and a second value of a second stimulation parameter and the second electrical stimulation therapy defines a third value of the first stimulation parameter and a fourth value of the second stimulation parameter, and delivering the second electrical stimulation therapy to the patient comprises instantaneously shifting stimulation delivery from the second value to the fourth value of the second stimulation parameter upon receiving the input and gradually shifting from the first value to the third value of the first stimulation parameter value according to a predetermined rate of change or over a predetermined duration of time.

In some examples of the method, the first electrical stimulation therapy defines a first value of a first stimulation parameter and a second value of a second stimulation parameter and the second electrical stimulation therapy defines a third value of the first stimulation parameter and a fourth value of the second stimulation parameter, and delivering the second electrical stimulation therapy to the patient comprises gradually shifting from the first value to the third value of the first stimulation parameter value according to a first predetermined rate of change or over a first predetermined duration of time and gradually shifting from the second value to the fourth value of the second stimulation parameter value according to a second predetermined rate of change or over a second predetermined duration of time, wherein the first and second predetermined rates of change are different and the first and second predetermined durations of time are different.

In some examples of the method, the first electrical stimulation therapy defines a first value of a first stimulation parameter and a second value of a second stimulation parameter and the second electrical stimulation therapy defines a third value of the first stimulation parameter and a fourth value of the second stimulation parameter, and delivering the second electrical stimulation therapy to the patient comprises gradually transitioning therapy delivery from the first value to the third value of the first stimulation parameter value and subsequently gradually transitioning therapy delivery from the second value to the fourth value of the second stimulation parameter value.

In some examples of the method, the method further comprises delivering a prestimulus before delivering the second stimulation therapy. In some examples, the prestimulus comprises at least one stimulation pulse comprising an amplitude of about 0.10 to about 0.50 of an amplitude of a stimulation signal defined by the second electrical stimulation therapy. In addition, in some examples, delivering the prestimulus comprises delivering the prestimulus about 1 millisecond to about 25 milliseconds before delivering the second electrical stimulation therapy.

In some examples of the method, the method further comprises delivering stimulation to block nerve conduction while delivering the second electrical stimulation therapy. In some examples, delivering the stimulation to block nerve conduction comprises delivering a stimulation signal having a frequency of about 200 Hertz to about 20 kilohertz. In addition, in some examples, delivering second electrical stimulation therapy to the patient comprises delivering the second electrical stimulation therapy to a target nerve, and wherein delivering stimulation to block nerve conduction comprises delivering stimulation to block conduction of the target nerve.

In some examples of the method, the method further comprises delivering a third electrical stimulation therapy to minimize discomfort to the patient while delivering the second electrical stimulation therapy. In some examples, delivering second electrical stimulation therapy to the patient comprises delivering the second electrical stimulation therapy to a target nerve and delivering the third electrical stimulation therapy comprises delivering the third electrical stimulation therapy to a dermatome associated with the target nerve.

In other examples, the disclosure is directed to a computer-readable comprising instructions that cause a programmable processor to control a therapy delivery module to deliver a first electrical stimulation therapy to a patient to generate a first physiological effect, receive input from the patient or a sensor while the therapy delivery module is delivering the first electrical stimulation therapy, and control the therapy delivery module to deliver a second electrical stimulation therapy to the patient based on the input from the patient or the sensor, wherein the delivery of the second electrical stimulation therapy generates a second physiological effect that is different than the first physiological effect, and wherein the first and second electrical stimulation therapies are configured to manage one of urinary incontinence or fecal incontinence.

The techniques described in this disclosure, including those attributed to programmer 24, IMD 16, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 50 of IMD 16 and/or processor 70 of programmer 24, any one or more parts of the techniques described herein may be implemented by a processor of one of IMD 16, programmer 24, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Many examples of the disclosure have been described. These and other examples are within the scope of the following claims. Various modifications may be made without departing from the scope of the claims.

The invention claimed is:

1. A method comprising:
generating, by a processor, incontinence information based upon a timing of a plurality of trigger events stored by a memory, wherein each trigger event of the plurality of trigger events occurred after initiation of delivery of a first stimulation therapy to a patient to generate a first physiological effect, and delivery of a second stimulation therapy to the patient to generate a second physiological effect different than the first physiological effect was initiated based upon each trigger event of the plurality of trigger events, wherein the first and second stimulation therapies are configured to manage at least one of urinary incontinence or fecal incontinence; and
presenting the incontinence information to a user.

2. The method of claim 1, wherein each trigger event of the plurality of trigger events initiated at least one of temporary delivery of the second stimulation therapy in addition to the first stimulation therapy or a temporary amplitude increase of the first stimulation therapy to deliver the second stimulation therapy.

3. The method of claim 1, wherein presenting the incontinence information comprises presenting the incontinence information on a display of an external programmer.

4. The method of claim 1, wherein presenting the incontinence information comprises presenting a graphical representation of the incontinence information.

5. The method of claim 1, wherein the incontinence information comprises at least one of a number of trigger events of the plurality of trigger events associated with a common cluster of trigger events, a ranking of a plurality of clusters of trigger events based upon a number or frequency of trigger events within each cluster, a number or frequency of clusters of trigger events associated with a therapy program, or a number or frequency of trigger events of clusters of trigger events associated with at least one type of patient activity.

6. The method of claim 1, further comprising receiving at least one of the trigger events as at least a patient input.

7. The method of claim 6, further comprising associating each trigger event of the plurality of trigger events with a therapy program that defines the first stimulation therapy delivered when each trigger event of the plurality of trigger events occurred.

8. The method of claim 1, further comprising:
presenting a plurality of incontinence therapy programs to the user; and
receiving a therapy program selection from the user that selects at least one therapy program from the plurality of incontinence therapy programs for subsequent delivery of the first stimulation therapy.

9. The method of claim 1, further comprising automatically selecting a therapy program to define subsequent first stimulation therapy for the patient, wherein the therapy program is selected from a group of evaluated therapy programs and is associated with a relatively fewest number of trigger events.

10. The method of claim 1, wherein the first physiological effect comprises inhibiting contraction of a bladder of the patient, and the second physiological effect comprises promoting contraction of one or more of a bladder outlet of the patient, an internal urinary sphincter of the patient, an external urinary sphincter of the patient, or periurethral muscles of the patient.

11. The method of claim 1, further comprising, after initiation of delivery of the first stimulation therapy, receiving an indication that the first stimulation therapy was delivered to the patient.

12. The method of claim 1, further comprising recognizing, by the processor, one or more trigger events of the plurality of trigger events as one cluster of a plurality of clusters of trigger events based upon the timing of the one or more trigger events.

13. The method of claim 12, wherein recognizing the one or more trigger events of the plurality of trigger events as one cluster of trigger events based upon the timing of the one or more trigger events comprises recognizing the one or more trigger events as one cluster of trigger events in response to determining the one or more trigger events occurred during a predetermined period of time.

14. The method of claim 1, wherein the incontinence information comprises at least one of a trend, a frequency, or a number of trigger events or clusters of trigger events over time, time durations between voluntary voiding events of the patient and a respective first subsequent trigger event or cluster of trigger events, time durations between individual trigger events within a cluster of trigger events, a number or frequency of trigger events or clusters of trigger events associated with different times of day, or a number or frequency of trigger events or clusters of trigger events associated with at least one physiological parameter of the patient.

15. The method of claim 1, wherein the incontinence information comprises a number of trigger events of the plurality of trigger events or clusters of trigger events associated with each time period of a plurality of time periods.

16. The method of claim 1, wherein the incontinence information comprises time durations between at least some of the trigger events of the plurality of trigger events or clusters of trigger events.

17. A system comprising:
a memory configured to store a plurality of trigger events;
a processor configured to generate incontinence information based upon a timing of a plurality of trigger events stored by the memory, wherein each trigger event of the plurality of trigger events occurred after initiation of delivery of a first stimulation therapy to a patient to generate a first physiological effect, delivery of a second stimulation therapy to the patient to generate a second physiological effect different than the first physiological effect was initiated based upon each trigger event of the plurality of trigger events, and the first and second stimulation therapies are configured to manage at least one of urinary incontinence or fecal incontinence; and
a user interface configured to present the incontinence information to a user.

18. The system of claim 17, further comprising a therapy delivery module configured to, based upon each trigger event of the plurality of trigger events, at least one of temporarily deliver the second stimulation therapy in addition to the first stimulation therapy or temporarily increase an amplitude of the first stimulation therapy to deliver the second stimulation therapy.

19. The system of claim 17, further comprising an external programmer comprising the user interface, the user interface comprising a display configured to present the incontinence information on the display of the external programmer.

20. The system of claim 17, wherein the processor is configured to generate a graphical representation of the incontinence information.

21. The system of claim 17, wherein the incontinence information comprises at least one of a number of trigger events of the plurality of trigger events associated with a common cluster of trigger events, a ranking of a plurality of clusters of trigger events based upon a number or frequency of trigger events within each cluster, a number or frequency of clusters of trigger events associated with a therapy program, or a number or frequency of trigger events of clusters of trigger events associated with at least one type of patient activity.

22. The system of claim 17, further comprising at least one of a bladder sensor configured to indicate a bladder condition or an activity sensor configured to indicate a patient activity level or posture, wherein the processor is configured to generate at least one trigger event of plurality of trigger events based upon signals received from the bladder sensor or the activity sensor.

23. The system of claim 17, wherein the user interface is configured to receive an incontinence therapy adjustment input from a patient, at least one trigger event of the plurality of trigger events comprising the incontinence therapy adjustment.

24. The system of claim 17, wherein the processor is configured to associate each trigger event of the plurality of trigger events with a therapy program that defines the first stimulation therapy delivered when each trigger event of the plurality of trigger events occurred.

25. The system of claim 17, wherein the processor is configured to present a group of evaluated incontinence therapy programs to the user via the user interface, and receive a therapy program selection from the user via the user interface, the therapy program selection indicating a therapy program from the group of evaluated incontinence therapy programs for subsequent delivery of first stimulation therapy.

26. The system of claim 17, wherein the processor is configured to automatically select a therapy program to define subsequent first stimulation therapy for the patient, wherein the processor is configured to select the therapy program from a plurality of incontinence therapy programs that is associated with a fewest number of trigger events of the plurality of trigger events.

27. The system of claim 17, wherein the first physiological effect comprises inhibiting contraction of a bladder of the patient, and the second physiological effect comprises promoting contraction of one or more of a bladder outlet of the patient, an internal urinary sphincter of the patient, an external urinary sphincter of the patient, or periurethral muscles of the patient.

28. The system of claim 17, wherein the processor comprises a first processor, the system further comprising:
a therapy delivery module configured to generate and deliver the first electrical stimulation therapy to the patient to generate the first physiological effect and the second electrical stimulation therapy to the patient to generate the second physiological effect that is different than the first physiological effect; and
a second processor configured to control the therapy delivery module to deliver the second stimulation therapy in response to detecting one of the plurality of trigger events.

29. The system of claim 17, wherein the processor is configured to, after initiation of delivery of the first stimulation therapy, receive an indication that the first stimulation therapy was delivered to the patient.

30. The system of claim 17, wherein the incontinence information comprises at least one of a trend, a frequency, or a number of trigger events or clusters of trigger events over time, time durations between voluntary voiding events of the patient and a respective first subsequent trigger event or cluster of trigger events, time durations between individual trigger events within a cluster of trigger events, a number or frequency of trigger events or clusters of trigger events associated with different times of day, a number or frequency of trigger events or clusters of trigger events associated with at least one physiological parameter of the patient, a number of trigger events or clusters of trigger events associated with each of a plurality of time periods, or time durations between at least some of a plurality of trigger events or clusters of trigger events.

31. A system comprising:
means for generating incontinence information based upon a timing of a plurality of trigger events stored by a memory, wherein each trigger event of the plurality of trigger events occurred after initiation of delivery of a first stimulation therapy to a patient to generate a first physiological effect, delivery of a second stimulation therapy to the patient to generate a second physiological effect different than the first physiological effect was initiated based upon each trigger event of the plurality of trigger events, and the first and second stimulation therapies are configured to manage at least one of urinary incontinence or fecal incontinence; and means for presenting the incontinence information to a user.

32. The system of claim 31, wherein each trigger event of the plurality of trigger events initiated at least one of temporary delivery of the second stimulation therapy in addition to the first stimulation therapy or a temporary amplitude increase of the first stimulation therapy to deliver the second stimulation therapy.

33. The system of claim 31, wherein the incontinence information comprises at least one of a trend, a frequency, or a number of trigger events or clusters of trigger events over time, time durations between clusters of trigger events, a time duration between a voluntary voiding event of the patient and a first subsequent trigger event or cluster of trigger events, a time duration between individual trigger events in a cluster, a number of trigger events associated with a common cluster, a ranking of clusters of trigger events based upon a number or frequency of trigger events within each cluster, a number or frequency of clusters of trigger events associated with a therapy program, a number or frequency of trigger events or clusters of trigger events associated with time of day, a number or frequency of trigger events of clusters of trigger events associated with at least one type of patient activity, or a number or frequency of trigger events of clusters of trigger events associated with at least one physiological parameter of the patient.

34. A non-transitory computer-readable storage medium comprising one or more instructions that cause a processor to:

generate incontinence information based upon a timing of a plurality of trigger events stored in a memory, wherein each trigger event of the plurality of trigger events occurred after initiation of delivery of a first stimulation therapy to a patient to generate a first physiological effect, delivery of a second stimulation therapy to the patient to generate a second physiological effect different than the first physiological effect was initiated based upon each trigger event of the plurality of trigger events, wherein the first and second stimulation therapies are configured to manage at least one of urinary incontinence or fecal incontinence; and present the incontinence information to a user.

35. The non-transitory computer-readable storage medium of claim 34, wherein the incontinence information comprises at least one of a trend, a frequency, or a number of trigger events or clusters of trigger events over time, time durations between clusters of trigger events, a time duration between a voluntary voiding event of the patient and a first subsequent trigger event or cluster of trigger events, a time duration between individual trigger events in a cluster, a number of trigger events associated with a common cluster, a ranking of clusters of trigger events based upon a number or frequency of trigger events within each cluster, a number or frequency of clusters of trigger events associated with a therapy program, a number or frequency of trigger events or clusters of trigger events associated with time of day, a number or frequency of trigger events of clusters of trigger events associated with at least one type of patient activity, or a number or frequency of trigger events of clusters of trigger events associated with at least one physiological parameter of the patient.

* * * * *